US010723988B2

(12) United States Patent
Lowe, Jr. et al.

(10) Patent No.: US 10,723,988 B2
(45) Date of Patent: *Jul. 28, 2020

(54) MICROFLUIDIC CELL CULTURE

(71) Applicant: Berkeley Lights, Inc., Emeryville, CA (US)

(72) Inventors: Randall D. Lowe, Jr., Emeryville, CA (US); Kristin Beaumont, Oakland, CA (US); Aathavan Karunakaran, Berkeley, CA (US); Natalie Marks, Albany, CA (US); Jason M. McEwen, El Cerrito, CA (US); Mark P. White, San Francisco, CA (US); J. Tanner Nevill, El Cerrito, CA (US); Gang F. Wang, Mountain View, CA (US); Andrew W. McFarland, Berkeley, CA (US); Daniele Malleo, San Jose, CA (US); Keith J. Breinlinger, San Rafael, CA (US); Xiao Guan, San Rafael, CA (US); Kevin T. Chapman, Santa Monica, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 120 days.

This patent is subject to a terminal disclaimer.

(21) Appl. No.: 15/135,707

(22) Filed: Apr. 22, 2016

(65) Prior Publication Data

US 2016/0312165 A1   Oct. 27, 2016

Related U.S. Application Data

(60) Provisional application No. 62/151,325, filed on Apr. 22, 2015.

(51) Int. Cl.
*C12M 1/00* (2006.01)
*C12M 3/00* (2006.01)
(Continued)

(52) U.S. Cl.
CPC ............ *C12M 23/16* (2013.01); *C12M 29/10* (2013.01)

(58) Field of Classification Search
CPC ............................ C12M 23/20; C12M 25/00
See application file for complete search history.

(56) References Cited

U.S. PATENT DOCUMENTS

| 6,294,063 B1 | 9/2001 | Becker et al. |
| 6,942,776 B2 | 9/2005 | Medoro |

(Continued)

FOREIGN PATENT DOCUMENTS

| EP | 1065378 A2 | 1/2001 |
| JP | 2008505630 A | 2/2008 |

(Continued)

OTHER PUBLICATIONS

International Searching Authority, International Search Report and Written Opinion for PCT/US16/28808, dated Sep. 1, 2016.

(Continued)

*Primary Examiner* — Nathan A Bowers
(74) *Attorney, Agent, or Firm* — Shay Glenn LLP

(57) ABSTRACT

Systems, methods and kits are described for culturing one or more biological cells in a microfluidic device, including provision of nutrients and gaseous components configured to enhance cell growth, viability, portability, or any combination thereof. In some embodiments, culturing a single cell may produce a clonal population in the microfluidic device.

42 Claims, 22 Drawing Sheets

(51) Int. Cl.
*B01L 3/00* (2006.01)
*C12M 3/06* (2006.01)

(56) References Cited

U.S. PATENT DOCUMENTS

| | | | |
|---|---|---|---|
| 7,090,759 | B1 | 8/2006 | Seul |
| 7,252,928 | B1 | 8/2007 | Hafeman et al. |
| 8,679,843 | B2 | 3/2014 | Faris et al. |
| 8,685,344 | B2 | 4/2014 | Sudarsan et al. |
| 9,744,533 | B2* | 8/2017 | Breinlinger ....... B01L 3/502715 |
| 2003/0008364 | A1 | 1/2003 | Wang et al. |
| 2003/0047456 | A1 | 3/2003 | Medoro |
| 2003/0175947 | A1 | 9/2003 | Liu et al. |
| 2003/0224528 | A1 | 12/2003 | Chiou et al. |
| 2004/0072278 | A1 | 4/2004 | Chou et al. |
| 2004/0191789 | A1 | 9/2004 | Manaresi et al. |
| 2004/0229349 | A1 | 11/2004 | Daridon |
| 2005/0089993 | A1 | 4/2005 | Boccazzi et al. |
| 2005/0112548 | A1 | 5/2005 | Segawa et al. |
| 2005/0129581 | A1 | 6/2005 | McBride et al. |
| 2005/0175981 | A1 | 8/2005 | Voldman et al. |
| 2005/0274612 | A1 | 12/2005 | Segawa et al. |
| 2006/0091015 | A1 | 5/2006 | Lau |
| 2006/0154361 | A1 | 7/2006 | Wiskwo et al. |
| 2006/0165565 | A1* | 7/2006 | Ermakov ............. B01J 19/0046 422/130 |
| 2006/0226012 | A1 | 10/2006 | Thirukumaran et al. |
| 2006/0263612 | A1 | 11/2006 | Chen et al. |
| 2007/0095669 | A1 | 5/2007 | Lau et al. |
| 2008/0013092 | A1 | 1/2008 | Maltezos et al. |
| 2008/0223721 | A1 | 9/2008 | Cohen et al. |
| 2008/0257735 | A1 | 10/2008 | Jeon et al. |
| 2008/0299539 | A1 | 12/2008 | Lee et al. |
| 2008/0302732 | A1 | 12/2008 | Soh et al. |
| 2009/0023608 | A1 | 1/2009 | Hung et al. |
| 2009/0170186 | A1 | 7/2009 | Wu et al. |
| 2010/0003666 | A1 | 1/2010 | Lee et al. |
| 2010/0101960 | A1 | 4/2010 | Ohta et al. |
| 2010/0273681 | A1 | 10/2010 | Cerrina et al. |
| 2011/0053151 | A1 | 3/2011 | Hansen et al. |
| 2011/0108422 | A1 | 5/2011 | Heller et al. |
| 2011/0117634 | A1 | 5/2011 | Halamish et al. |
| 2011/0143964 | A1 | 6/2011 | Zhou et al. |
| 2011/0262906 | A1 | 10/2011 | Dinnov et al. |
| 2012/0009671 | A1 | 1/2012 | Hansen et al. |
| 2012/0015347 | A1 | 1/2012 | Singhal et al. |
| 2012/0024708 | A1 | 2/2012 | Chiou et al. |
| 2012/0073740 | A1 | 3/2012 | Hsieh |
| 2012/0118740 | A1 | 5/2012 | Garcia et al. |
| 2012/0156675 | A1 | 6/2012 | Lueerssen et al. |
| 2012/0208266 | A1 | 8/2012 | Bookbinder et al. |
| 2012/0325665 | A1 | 12/2012 | Chiou et al. |
| 2013/0118905 | A1 | 5/2013 | Morimoto et al. |
| 2013/0171628 | A1 | 5/2013 | Di Carlo et al. |
| 2013/0146459 | A1 | 6/2013 | Bazant et al. |
| 2013/0171546 | A1 | 7/2013 | White et al. |
| 2013/0190212 | A1 | 7/2013 | Handique et al. |
| 2013/0204076 | A1 | 8/2013 | Han et al. |
| 2013/0261021 | A1 | 10/2013 | Bocchi et al. |
| 2013/0280485 | A1 | 10/2013 | Coclite et al. |
| 2013/0288065 | A1 | 10/2013 | Chen et al. |
| 2014/0057311 | A1 | 2/2014 | Kamm et al. |
| 2014/0116881 | A1 | 5/2014 | Chapman et al. |
| 2014/0124370 | A1 | 5/2014 | Short et al. |
| 2014/0153079 | A1 | 6/2014 | Hsieh |
| 2014/0154703 | A1 | 6/2014 | Skelley et al. |
| 2014/0154791 | A1 | 6/2014 | North et al. |
| 2014/0255976 | A1 | 9/2014 | Chang et al. |
| 2014/0299472 | A1 | 10/2014 | Chang et al. |
| 2014/0308688 | A1 | 10/2014 | Grego et al. |
| 2015/0018226 | A1 | 1/2015 | Hansen et al. |
| 2015/0151298 | A1 | 6/2015 | Hobbs et al. |
| 2015/0151307 | A1 | 6/2015 | Breinlinger et al. |
| 2015/0165436 | A1 | 6/2015 | Chapman et al. |
| 2015/0167043 | A1 | 6/2015 | Goluch et al. |
| 2015/0306598 | A1 | 10/2015 | Khandros et al. |
| 2015/0306599 | A1 | 10/2015 | Khandros et al. |
| 2015/0352547 | A1 | 12/2015 | Breinlinger et al. |
| 2016/0067711 | A1* | 3/2016 | Yoon ..................... C12M 47/04 506/2 |
| 2016/0184821 | A1 | 6/2016 | Hobbs et al. |
| 2016/0193604 | A1 | 7/2016 | McFarland et al. |
| 2016/0199837 | A1 | 7/2016 | Breinlinger et al. |
| 2016/0222224 | A1* | 8/2016 | Haag ..................... C12M 23/20 |
| 2016/0252495 | A1 | 9/2016 | Ricicova et al. |
| 2016/0257918 | A1 | 9/2016 | Chapman et al. |
| 2017/0021366 | A1 | 1/2017 | Chapman et al. |
| 2018/0099282 | A1* | 4/2018 | Breinlinger .......... G01N 1/4077 |

FOREIGN PATENT DOCUMENTS

| | | |
|---|---|---|
| JP | 2009538130 A | 11/2009 |
| KR | 10-2010-0008222 | 1/2010 |
| WO | 2008057366 | 5/2008 |
| WO | 2009146143 | 12/2009 |
| WO | 2010147078 | 12/2010 |
| WO | WO2012/024658 A2 | 2/2012 |
| WO | WO2013/130714 A1 | 9/2013 |
| WO | 2013148745 | 10/2013 |
| WO | 2013148745 A1 | 10/2013 |
| WO | 2014081840 | 5/2014 |
| WO | WO2014/070873 A1 | 5/2014 |
| WO | 2014167858 A1 | 10/2014 |
| WO | 2015036364 A1 | 3/2015 |
| WO | WO2015/164846 A1 | 10/2015 |
| WO | WO2015/164847 A1 | 10/2015 |
| WO | 2015188171 A1 | 12/2015 |
| WO | 2016090295 A1 | 6/2016 |

OTHER PUBLICATIONS

Chiou et al., Massively parallel manipulation of single cells and microparticles using optical images, Nature 436:370-73 (2005).
Yi, Analytica Chimica Acta 560:1-23 (2006).
Nevill et al., Integrated microfluidic cell culture and lysis on a chip, Lab on a Chip 7:1689-95 (2007).
Hsu et al., Sorting of Differentiated Neurons using Phototransistor-based Optoelectronic Tweezers for Cell Replacement Therapy of Neurodegenerative Diseases, IEEE Conference on Transducers (Jun. 21-25, 2009).
Valley et al., Optoelectronic Tweezers as a Tool for Parallel Single-Cell Manipulation and Stimulation, IEEE Transactions on Biomedical Circuits and Systems 3(6):424-30 (2009).
Xu, Guolin et al,. Recent Trends in Dielectrophoresis, Informacije MIDEM, 2010, vol. 40, Issue No. 4, pp. 253-262.
Young et al., Fundamentals of microfluidic cell culture in controlled microenvironments, Chem Soc Rev 39(3):1036-48 (2010).
Dalvi et al., Molecular Origins of Fluorocarbon Hydrophobicity, Proceedings of the National Academy of Sciences, 107(31):13603-7 (2010).
Valley et al., A unified platform for optoelectrowetting and optoelectronic tweezers, Lab on a Chip 11:1292-97 (2011).
Lee et al., Microfluidic chemostat and Turbidostat with flow rate, oxygen and temperature control for dynamic continuous culture, Lab on a Chip 11:1730-39 (2011).
Lowe,"Controlled Vapor Deposition of Azide-terminated Siloxane Monolayers: a Platform for Tailoring Oxide Surfaces", Stanford University, Aug. 2011.
Chung et al., Imaging single-cell signaling dynamics with a deterministic high-density single-cell trap array, Anal. Chem.83(18):7044-7052 (2011).
Banuls et al. Chemical surface modifications for the development of silicon-based label-free integrated optical (IO) biosensors: A review.
Somaweera et al., Generation of a Chemical Gradient Across an Array of 256 Cell Cultures in a Single Chip, Analyst., Oct. 7, 2013, vol. 138, No. 19, pp. 5566-5571.
Mehling et al., Microfluidic Cell Culture, Curr. Op. Biotech. 25:95-102 (2014).

(56) References Cited

OTHER PUBLICATIONS

Hung et al., Continuous Perfusion Microfluidic Cell Culture Array for High-Throughput Cell-Based Assays, Biotech and Bioengineering 89(1): 1-8 (2004).
Iliescu et al., Continuous field-flow separation of particle populations in a dielectrophoretic chip with three dimensional electrodes, Applied Physics Letters 90:234104 (2007).
Lagally et al., Parallel microfluidic arrays for SPRI detection, Proceedings of SPIE, vol. 7759, p. 77590J (2010).
Swain et al., Advances in embryo culture platforms: novel approaches to improve preimplantation embryo development through modifications of the microenvironment, Human Reproduction Update 17(4):541-57 (2011).
International Search Report and Written Opinion for PCT Application Serial No. PCT/US2016028808 (dated Sep. 1, 2016), 13 pages.
Bellis S.L., Advantages of RGD Peptides for Directing Cell Association with Biomaterials, Jun. 2011, vol. 32, No. 18, pp. 4205-4210.
Di Carlo et al.; Dynamic single-cell analysis for quantitative biology; Analytical Chemistry; pp. 7918-7925; Dec. 2006.
Ritchie et al.; Reconstitution of Membrane Proteins in Phospholipid Bilayer Nanodiscs; Methods Enzymol; 464; pp. 211-231; 23 pages; (Author Manuscript); Jan. 2009.
Zhang et al., "Azide Functional Monolayers Grafted to a Germanium Surface: Model Substrates for ATR-IR Studies of Interfacial Click Reactions," Langmuir, Vo. 28, No. 1, Nov. 14, 2011.
Papageorgiou, D. P., et al., Superior Performance of Multilayered Fluoropolymer Films in Low Voltage Electrowetting. Journal f Colloid Interface Science, Oct. 25, 2011, vol. 368, No. 1, pp. 592-598.

* cited by examiner

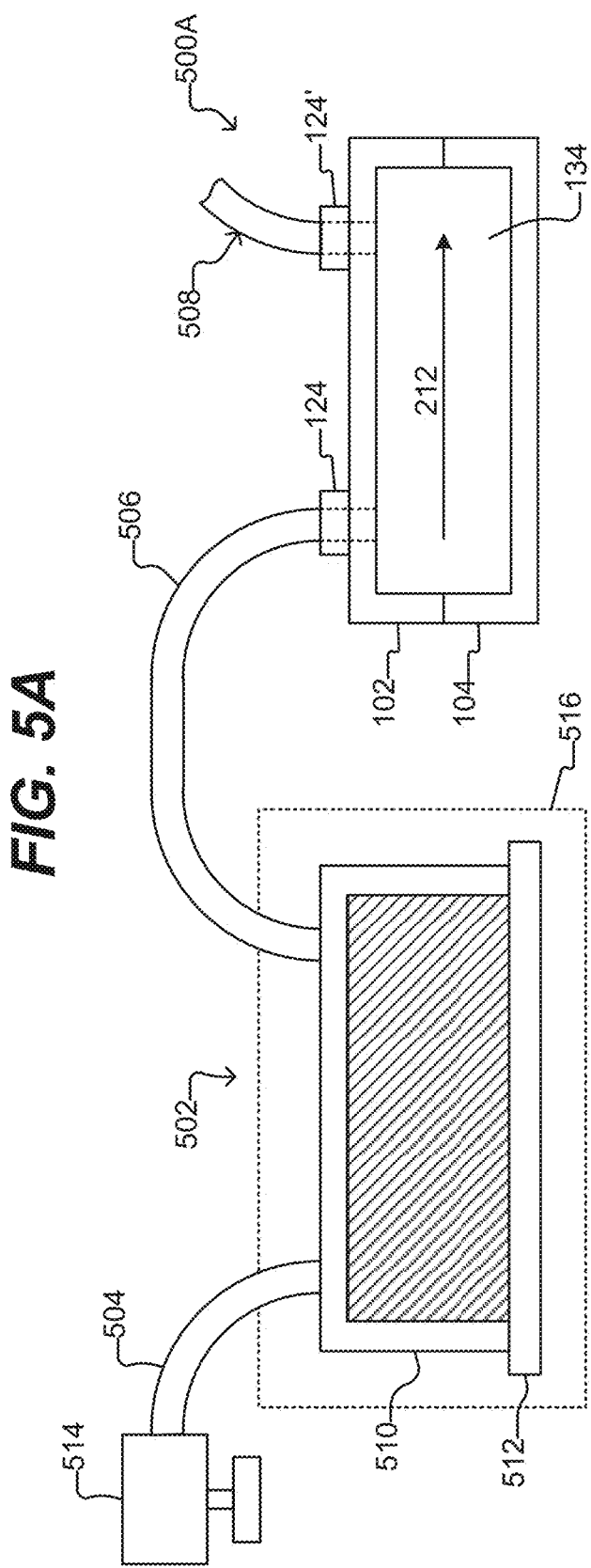

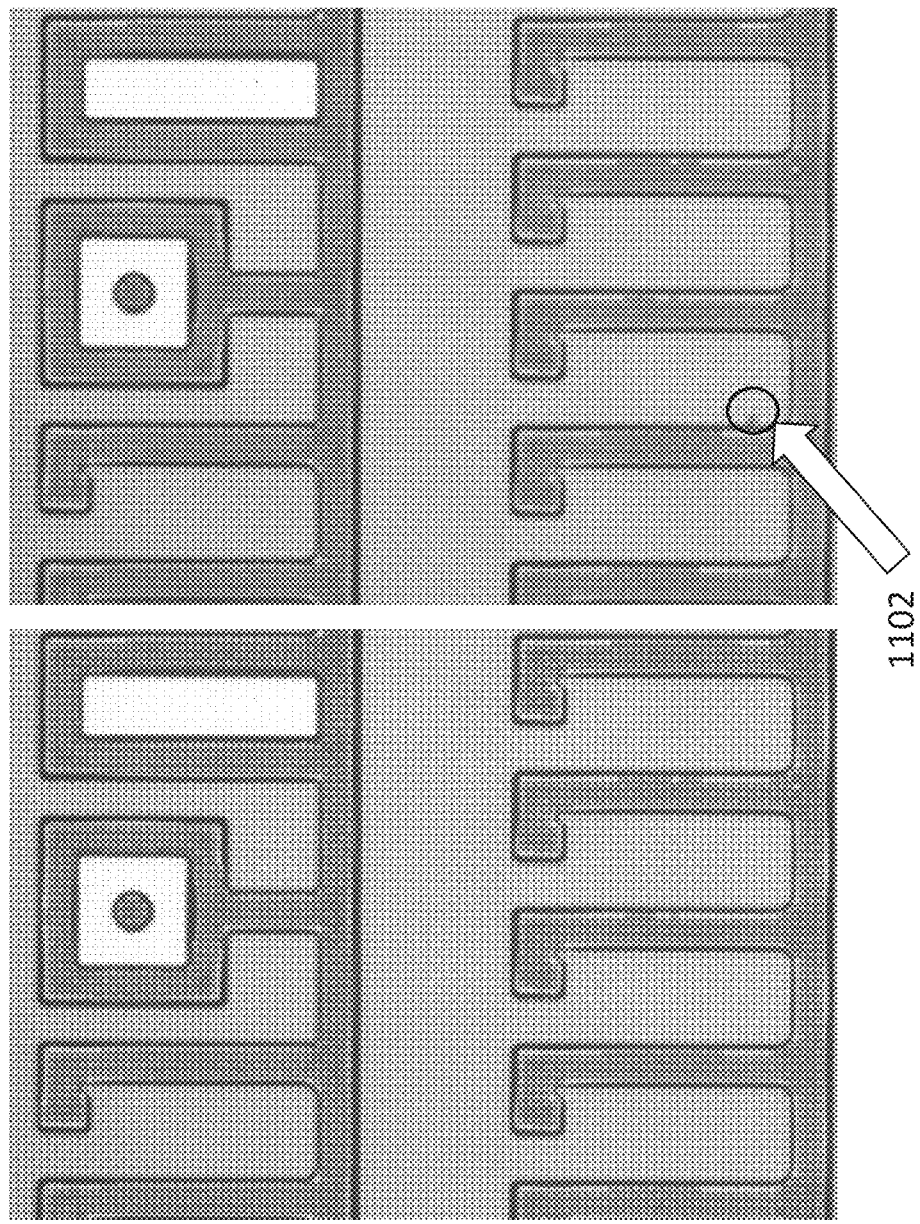

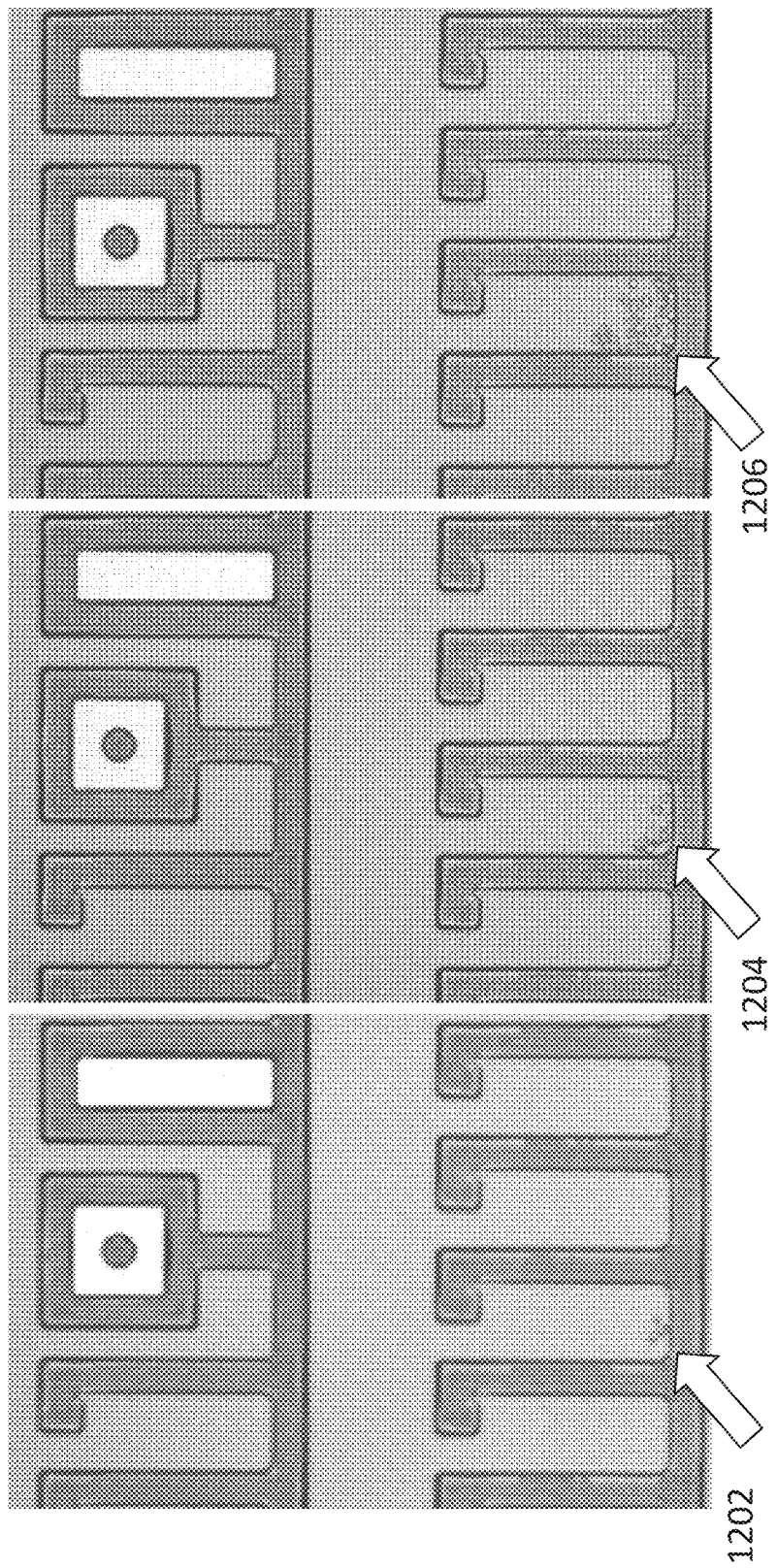

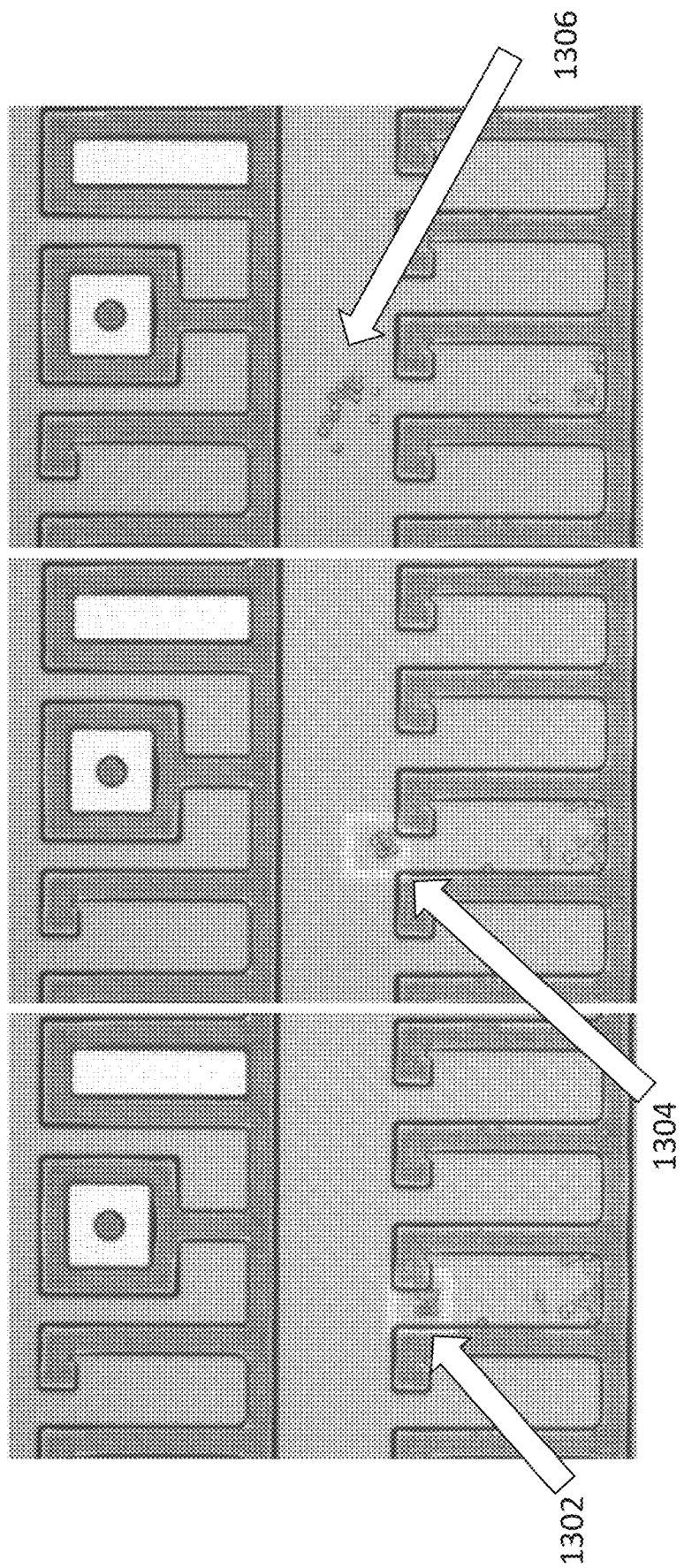

MICROFLUIDIC CELL CULTURE

This application is a non-provisional application claiming the benefit under 35 U.S.C. 119(e) of U.S. Provisional Application No. 62/151,325 filed on Apr. 22, 2015, which disclosure is herein incorporated by reference in its entirety.

BACKGROUND OF THE INVENTION

In biosciences and related fields, it can be useful to culture a cell or cells. Some embodiments of the present invention include apparatuses and processes for culturing a cell or groups of cells in a microfluidic device.

SUMMARY OF THE INVENTION

In one aspect, a microfluidic device for culturing one or more biological cells is provided, including a flow region configured to contain a flow of a first fluidic medium; and at least one growth chamber including an isolation region and a connection region, the isolation region being fluidically connected with the connection region and the connection region including a proximal opening to the flow region, where the at least one growth chamber further includes at least one surface conditioned to support cell growth, viability, portability, or any combination thereof within the microfluidic device. In some embodiments, the isolation region of the microfluidic device may be configured to contain a second fluidic medium, and where, when the flow region and the at least one growth chamber are substantially filled with the first and second fluidic media respectively, components of the second fluidic medium may diffuse into the first fluidic medium and/or components of the first fluidic medium may diffuse into the second fluidic medium, and the first medium may not substantially flow into the isolation region. In some embodiments, the microfluidic device may further include a microfluidic channel having at least a portion of the flow region, and wherein the connection region of the at least one growth chamber may open directly into the microfluidic channel.

In some embodiments, the at least one conditioned surface may be conditioned with one or more agents that support cell portability within the microfluidic device. In some embodiments, the at least one conditioned surface may be conditioned with a polymer including alkylene ether moieties. In other embodiments, the at least one conditioned surface may be conditioned with a polymer including saccharide moieties. In some embodiments, the polymer including saccharide moieties may include dextran. In other embodiments, the at least one conditioned surface may be conditioned with a polymer including amino acid moieties. In some embodiments, the polymer may be bovine serum albumin (BSA) or DNase 1. In yet other embodiments, the at least one conditioned surface of the microfluidic device may be conditioned with a polymer including carboxylic acid moieties, sulfonic acid moieties, nucleic acid moieties, or phosphonic acid moieties. In some embodiments, the at least one conditioned surface of the microfluidic device may be conditioned with a polymer including carboxylic acid moieties, sulfonic acid moieties, nucleic acid moieties, or phosphonic acid moieties.

In various embodiments of the microfluidic device, the at least one conditioned surface includes a linking group covalently linked to a surface of the microfluidic device, and the linking group may be linked to a moiety configured to support cell growth, viability, portability, or any combination thereof within the microfluidic device. In some embodiments, the linking group may be a siloxy linking group. In other embodiments, the linking group may be a phosphonate ester linking group. In various embodiments, the at least one conditioned surface may include alkyl or fluoroalkyl moieties. In some embodiments, the fluoroalkyl moieties may be perfluoroalkyl moieties. In some embodiments, the alkyl or fluoroalkyl moieties may have a backbone chain length of greater than 10 carbons. The alkyl or fluoroalkyl moieties may have a linear structure. In various embodiments of the microfluidic device, the linking group of the at least one conditioned surface may be directly linked to the moiety configured to support cell growth, viability, portability, or any combination thereof. In other embodiments, linking group may be indirectly linked to the moiety configured to support cell growth, viability, portability, or any combination thereof. In some embodiments, the linking group may be indirectly linked via a linker to the moiety configured to support cell growth, viability, portability, or any combination thereof. In some embodiments, the linker may include a triazolylene moiety. In other embodiments, the linker may include one or more arylene moieties. In some embodiments, the at least one conditioned surface may include saccharide moieties. In other embodiments, the at least one conditioned surface may include alkylene ether moieties. In yet other embodiments, the at least one conditioned surface may include amino acid moieties. Alternatively, the at least one conditioned surface may include zwitterions. In further embodiments, the at least one conditioned surface may include phosphonic acid moieties or carboxylic acid moieties. In other embodiments, the at least one conditioned surface includes amino or guanidine moieties. In some other embodiments, the at least one conditioned surface may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetain; sulfamic acid; or amino acids.

In various embodiments of the microfluidic device, the at least one conditioned surface of the microfluidic device may include at least one cell adhesion blocking molecule. In some embodiments, the at least one cell adhesion blocking molecule may disrupt actin filament formation, block integrin receptors, or reduce binding of cells to DNA fouled surfaces. In some embodiments, the at least one cell adhesion blocking molecule may be an RGD containing peptide. In other embodiments the at least one cell adhesion blocking molecule may be Cytochalasin B, an antibody to an integrin, inhibitor of fibronectin, which may include a small molecule or a DNase 1 protein. In other embodiments, the at least one cell adhesion blocking molecule may include a combination of more than one type of cell adhesion blocking molecules.

In various embodiments of the microfluidic device, the at least one conditioned surface of the microfluidic device may include a cleavable moiety. In some embodiments, the cleavable moiety may be configured to permit disruption of the conditioned surface thereby promoting portability of the one or more biological cells after culturing.

In various embodiments of the microfluidic device, the at least one conditioned surface of the microfluidic device may include one or more components of mammalian serum. The one or more components of mammalian serum may include B27® Supplement, Fetal Bovine Serum (FBS), or Fetal Calf Serum (FCS).

In various embodiments of the microfluidic device, the microfluidic device may further include a substrate having a dielectrophoresis (DEP) configuration. In some embodiments, the substrate having a DEP configuration may be configured to introduce one or more biological cells into or move the one or more biological cells out of the growth chamber. The DEP configuration may be optically actuated.

In various embodiments of the microfluidic device, the at least one conditioned surface of the microfluidic device may be configured to be stable at a temperature of at least about 30° C.

In various embodiments of the microfluidic device, the isolation region of the at least one growth chamber of the microfluidic device may have dimensions sufficient to support cell expansion to a range of about 100 cells. In some embodiments, no more than $1 \times 10^2$ biological cells may be maintained in the at least one growth chamber, and the volume of the at least one growth chamber may be less than or equal to about $2 \times 10^6$ cubic microns. In other embodiments, no more than $1 \times 10^2$ biological cells may be maintained in the at least one growth chamber, and the volume of the at least one growth chamber may be less than or equal to about $1 \times 10^7$ cubic microns.

In various embodiments of the microfluidic device, the device may further include at least one inlet port configured to input the first or second fluidic medium into the flow region and at least one outlet port configured to receive the first medium as it exits from the flow region. In various embodiments of the microfluidic device, the microfluidic device may further include a deformable lid region above the at least one growth chamber or the isolation region thereof, whereby depressing the deformable lid region exerts a force sufficient to export the biological cell from the isolation region to the flow region. In various embodiments of the microfluidic device, the microfluidic device may include a lid wherein at least a portion of the lid may be gas permeable, thereby providing a source of gaseous molecules to a fluidic medium located in the microfluidic device. The gas permeable portion of the lid may be located over the at least one growth chamber. In other embodiments, the gas permeable portion of the lid may be located over the flow region. In yet other embodiments, the at least one growth chamber may include a plurality of growth chambers.

In various embodiments, the one or more biological cells may include a plurality of biological cells. In various embodiments of the microfluidic device, the at least one growth chamber may include at least one surface conditioned to support cell growth, viability, portability, or any combination thereof of a mammalian cell. In other embodiments, the at least one growth chamber may include at least one surface conditioned to support cell growth, viability, portability, or any combination thereof of an immunological cell. In yet other embodiments, the immunological cell may be a lymphocyte or leukocyte. In some other embodiments, the immunological cell may be a B cell, a T cell, NK cell, a macrophage, or a dendritic cell.

In various embodiments of the microfluidic device, the at least one growth chamber may include at least one surface conditioned to support cell growth, viability, portability, or any combination thereof of an adherent cell.

In various embodiments of the microfluidic device, the at least one growth chamber may include at least one surface conditioned to support cell growth, viability, portability, or any combination thereof of a hybridoma cell.

In various embodiments of the microfluidic device, the at least one growth chamber may include at least one surface conditioned to support cell growth, viability, portability, or any combination thereof of a single cell and a corresponding clonal colony of biological cells.

In another aspect, a system for culturing one or more biological cells on a microfluidic device is provided, the system including a microfluidic device having a flow region configured to contain a flow of a first fluidic medium; and at least one growth chamber wherein the growth chamber has at least one surface conditioned to support cell growth, viability, portability, or any combination thereof in the microfluidic device. The at least one growth chamber may include an isolation region and a connection region, the isolation region being fluidically connected with the connection region and the connection region having a proximal opening to the flow region. In some embodiments, the isolation region of the microfluidic device may be configured to contain a second fluidic medium, and when the flow region and the at least one growth chamber are substantially filled with the first and second fluidic media respectively, components of the second fluidic medium may diffuse into the first fluidic medium and/or components of the first fluidic medium may diffuse into the second fluidic medium, and the first medium may not substantially flow into the isolation region. In some embodiments, the microfluidic device may further include a microfluidic channel which includes at least a portion of the flow region, and wherein the connection region of the at least one growth chamber may open directly into the microfluidic channel. The microfluidic device may be any microfluidic device as described herein, having any of the elements in any combination.

In various embodiments of the system, the system may further include a flow controller configured to perfuse at least the first fluidic medium. The controller is configured to perfuse the at least first fluidic medium non-continuously.

In various embodiments of the system, the microfluidic device of the system may further include a substrate having a dielectrophoresis (DEP) configuration configured to introduce one or more biological cells into or move the one or more biological cells out of the growth chamber. The DEP configuration may be optically actuated.

In various embodiments of the system, the system may further include a reservoir configured to contain the first fluidic medium, wherein the reservoir is fluidic ally connected to the microfluidic device. The reservoir may be configured to be contacted by a gaseous environment capable of saturating the first fluidic medium with dissolved gaseous molecules.

In various embodiments of the system, the system may further include a sensor connected to at least one inlet port of the microfluidic device, wherein the sensor may be configured to detect a pH of the first fluidic medium. In various embodiments of the system, the system may further include a sensor connected to at least one outlet, wherein the sensor is configured to detect a pH of the first fluidic medium as the first fluidic medium leaves the microfluidic device. In some embodiments, the sensor may be an optical sensor.

In various embodiments of the system, the system may further include a detector configured to capture an image of the at least one growth chamber and any biological cells contained therein. In some embodiments, the one or more biological cells may include one or more mammalian cells. In other embodiments, the one or more biological cells may include one or more hybridoma cells. In yet other embodiments, the one or more biological cells may include one or more lymphocyte or leukocyte cells. Alternatively, the one or more biological cells may include one or more adherent cells.

In various embodiments of the system, the one or more biological cells in the growth chamber may be a single cell and the colony may be a clonal colony of biological cells.

In another aspect, a composition is provided including a substrate having a dielectrophoresis (DEP) configuration and a surface; and a conditioned surface covalently linked to oxide moieties of the surface of the substrate. The composition may have a structure of Formula 1 or Formula 2, and may have any values of the elements of Formula 1 or Formula 2, as defined herein:

Formula 1

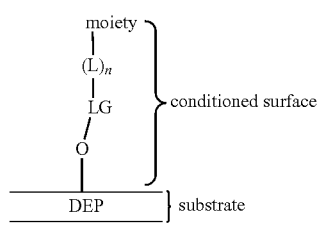

Formula 2

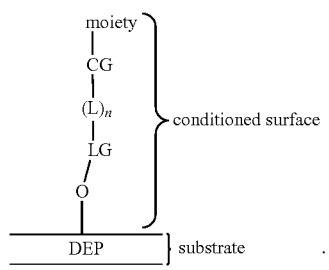

In some embodiments of the composition, the conditioned surface may include a linking group covalently linked to the oxide moieties of the surface, and the linking group may be linked to a moiety configured to support cell growth, viability, portability, or any combination thereof. In some embodiments, the linking group may be a siloxy linking group. In other embodiments, the linking group may be a phosphonate group. In some embodiments, the linking group may be directly linked to the moiety configured to support cell growth, viability, portability, or any combination thereof. In some embodiments, the linking group may be indirectly linked to the moiety configured to support cell growth, viability, portability, or any combination thereof. In some embodiments, the linking group may be indirectly linked to the moiety configured to support cell growth, viability, portability, or any combination thereof via connection to a linker. In some embodiments, the linking group may be indirectly linked to the moiety configured to support cell growth, viability, portability, or any combination thereof via connection to a first end of a linker. The linker may further include a linear portion wherein a backbone of the linear portion comprises 1 to 200 non-hydrogen atoms selected from any combination of silicon, carbon, nitrogen, oxygen, sulfur and phosphorus atoms. In some embodiments, the linker may further include a triazolylene moiety. In some embodiments, the triazolylene moiety may interrupt the linear portion of the linker or may be connected at a second end to the linear portion of the linker. In other embodiments, the backbone of the linear portion may include an arylene moiety.

In various embodiments, the moiety configured to support cell growth, viability, portability, or any combination thereof, may include an alkyl moiety, fluoroalkyl moiety, mono- or polysaccharide, alcohol moiety, polyalcohol moiety, alkylene ether moiety, polyelectrolyte moiety, amino moiety, carboxylic acid moiety, phosphonic acid moiety, sulfonate anion moiety, carboxybetaines moiety, sulfobetaine moiety, sulfamic acid moiety, or amino acid moiety. In some embodiments, the at least one conditioned surface may include amino acids, alkyl moieties, perfluoroalkyl moieties, dextran moieties and/or alkylene ether moieties. In some embodiments, the at least one conditioned surface may include alkyl or perfluoroalkyl moieties. In some embodiments, the alkyl or perfluoroalkyl moieties have a backbone chain length of greater than 10 carbons. In various embodiments, the conditioned surface may further include one or more cleavable moieties. The cleavable moiety may be configured to permit disruption of the conditioned surface thereby facilitating portability of the one or more biological cells after culturing.

In another aspect, a method is provided for culturing at least one biological cell in a microfluidic device having a flow region configured to contain a flow of a first fluidic medium, and at least one growth chamber, including the steps of introducing the at least one biological cell into the at least one growth chamber, wherein the at least one growth chamber is configured to have at least one surface conditioned to support cell growth, viability, portability, or any combination thereof; and, incubating the at least one biological cell for a period of time at least long enough to expand the at least one biological cell to produce a colony of biological cells. The at least one growth chamber may include an isolation region and a connection region, the isolation region being fluidically connected with the connection region and the connection region having a proximal opening to the flow region. In some embodiments, the isolation region of the microfluidic device may be configured to contain a second fluidic medium, and where, when the flow region and the at least one growth chamber are substantially filled with the first and second fluidic media respectively, components of the second fluidic medium may diffuse into the first fluidic medium and/or components of the first fluidic medium may diffuse into the second fluidic medium, and the first medium may not substantially flow into the isolation region. In some embodiments, the microfluidic device may further include a microfluidic channel having at least a portion of the flow region, and wherein the connection region of the at least one growth chamber may open directly into the microfluidic channel. The microfluidic device may be any microfluidic device as described herein, having any of the elements in any combination.

In some embodiments of the method, the at least one conditioned surface may include a linking group covalently linked to the surface, and further wherein the linking group is linked to a moiety configured to support cell growth, viability, portability, or any combination thereof of the one or more biological cells within the microfluidic device. In some other embodiments, the moiety configured to support cell growth, viability, portability, or any combination thereof, may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetain; sulfamic acids; or amino acids. In some embodiments, the at least one conditioned surface may include alkyl or perfluoroalkyl moieties. In other embodiments, the at least one conditioned surface may include alkylene ether moieties or dextran moieties.

In some embodiments of the method, the method may include a step of conditioning at least a surface of the at least one growth chamber. In some embodiments, conditioning may include treating the at least a surface of the at least one growth chamber with a conditioning reagent including a polymer. In other embodiments, conditioning may include treating at least a surface of the at least one growth chamber with one or more components of mammalian serum. In yet other embodiments, conditioning may include treating at least one surface of the at least one growth chamber with at least one cell adhesion blocking molecule.

In some embodiments of the method, introducing the at least one biological cell into the at least one growth chamber may include using a dielectrophoresis (DEP) force having sufficient strength to move the at least one biological cell. In some embodiments, using a DEP force may include optically actuating the DEP force.

In some embodiments of the method, the method may further include a step of perfusing the first fluidic medium during the incubating step, where the first fluidic medium is introduced via at least one inlet port of the microfluidic device and exported via at least one outlet of the microfluidic device, where, upon export, the first fluidic medium optionally includes components from the second fluidic medium.

In some embodiments of the method, the method may further include a step of cleaving one or more cleavable moieties of the conditioned surface after the incubating step, thereby facilitating export of the one or more biological cells out of the growth chamber or isolation region thereof and into the flow region.

In some embodiments of the method, the method may further include a step of exporting one or more biological cells out of the growth chamber or the isolation region thereof into the flow region.

In some embodiments of the method, the at least one biological cell may include a mammalian cell. In other embodiments of the method, the at least one biological cell may include at least one immunological cell. In yet other embodiments of the method, the at least one immunological cell may include a lymphocyte or leukocyte. In some other embodiments of the method, the at least one immunological cell may include a B cell, a T cell, NK cell, a macrophage, or a dendritic cell. In yet other embodiments, the at least one biological cell may include an adherent cell. Alternatively, the at least one biological cell may include a hybridoma cell.

In some embodiments of the method, the step of introducing the at least one biological cell into the at least one growth chamber may include introducing a single cell into the growth chamber, and the colony of biological cells produced by the incubating step may be a clonal colony.

In another aspect, a kit for culturing a biological cell is provided, including a microfluidic device having a flow region configured to contain a flow of a first fluidic medium; and at least one growth chamber including at least one surface conditioned to support cell growth, viability, portability, or any combination thereof within the microfluidic device. The at least one growth chamber may include an isolation region and a connection region, the isolation region being fluidically connected with the connection region and the connection region having a proximal opening to the flow region. The microfluidic device may be any microfluidic device as described herein having any combination of elements. In some embodiments, the at least one conditioned surface of the microfluidic device may include alkyl moieties, fluoroalkyl moieties, mono- or polysaccharide, moieties, alcohol moieties; polyalcohol moieties; alkylene ether moieties; polyelectrolyte moieties, amino moieties, carboxylic acid moieties, phosphonic acid moieties, sulfonate moieties; carboxybetaine moieties, sulfobetaine moieties; sulfamic acid moieties; or amino acid moieties. In some embodiments, the at least one conditioned surface of the microfluidic device comprises at least one of saccharide moieties, alkylene ether moieties, alkyl moieties, fluoroalkyl moieties, or amino acid moieties. In some embodiments, the alkyl or fluoroalkyl moieties have a backbone chain length of greater than 10 carbons.

In various embodiments of the kit, the at least one conditioned surface of the microfluidic device may include a linking group covalently linked to a surface of the microfluidic device, and the linking group may be linked to a moiety configured to support growth, viability, portability, or any combination thereof of the one or more biological cells within the microfluidic device. In some embodiments, the linking group may be a siloxy linking group. In other embodiments, the linking group may be a phosphonate linking group. In some embodiments, the linking group may be directly linked to the moiety configured to support cell growth, viability, portability, or any combination thereof. In other embodiments, the linking group may be indirectly linked to the moiety configured to support cell growth, viability, portability, or any combination thereof. The linking group may be indirectly linked to the moiety configured to support cell growth, viability, portability, or any combination thereof via a linker. The linking group may be indirectly linked to the moiety configured to support cell growth, viability, portability, or any combination thereof, via connection to a first end of a linker. In various embodiments, the linker may further include a linear portion wherein a backbone of the linear portion comprises 1 to 200 non-hydrogen atoms selected from any combination of silicon, carbon, nitrogen, oxygen, sulfur and phosphorus atoms. In some embodiments, the linker may include a triazolylene moiety.

In various embodiments of the kit, the kit may further include a surface conditioning reagent. In some embodiments, the surface conditioning reagent may include a polymer comprising at least one of alkylene ether moieties, carboxylic acid moieties, sulfonic acid moieties, phosphonic acid moieties, amino acid moieties, nucleic acid moieties or saccharide moieties. In some embodiments, the surface conditioning reagent may include a polymer including at least one of alkylene ether moieties, amino acid moieties, and/or saccharide moieties.

In other embodiments, the surface conditioning reagent may include at least one cell adhesion blocking molecule. In some embodiments, the at least one cell adhesion blocking molecule may disrupt actin filament formation, blocks integrin receptors, or reduces binding of cells to DNA fouled surfaces. In some embodiments, the at least one cell adhesion blocking molecule may be Cytochalasin B, an RGD containing peptide, an inhibitor of fibronectin, an antibody to an integrin, or a DNase 1 protein. In some embodiments, the surface conditioning reagent may include a combination of more than one cell adhesion blocking molecule.

In yet other embodiments, the surface conditioning reagent may include one or more components of mammalian serum. In some embodiment, the mammalian serum may be Fetal Bovine Serum (FBS), or Fetal Calf Serum (FCS).

In various embodiments of the kit, the kit may further include a culture medium additive including a reagent configured to replenish the conditioning of the at least one surface of growth chamber. The culture medium additive may include a Pluronics® polymer.

In various embodiments of the kit, the at least one conditioned surface of the microfluidic device may include a cleavable moiety. In some embodiments, the kit may further include a reagent configured to cleave the cleavable moiety of the conditioned surface.

In various embodiments of the kit, the kit may further include at least one reagent to detect a status of the biological cell.

BRIEF DESCRIPTION OF THE DRAWINGS

FIGS. 5A to 5E each represent an embodiment of system components capable of providing conditioned media to a microfluidic device to support cell growth, viability, portability, or any combination thereof.

FIG. 11A is a photographic representation of another embodiment of a culturing experiment according to the methods described herein, showing a microfluidic device before a cell is placed in the growth chambers of the device.

FIG. 11B is a photographic representation of an embodiment of the culturing experiment of FIG. 11A, at a later time when one cell is placed in one growth chamber of the microfluidic device.

FIGS. 12A-12C are photographic representations of an embodiment of the culturing experiment of FIGS. 11A and B, at a later time point, showing cell expansion during incubation of the cell of FIG. 11B.

FIGS. 13A-13C are photographic representations of an embodiment of the culturing experiment of FIG. 11A-B and FIGS. 12A-12C, at a later time point, showing export of expanded cells after the conclusion of the incubation period.

DETAILED DESCRIPTION OF THE INVENTION

Figure 1:
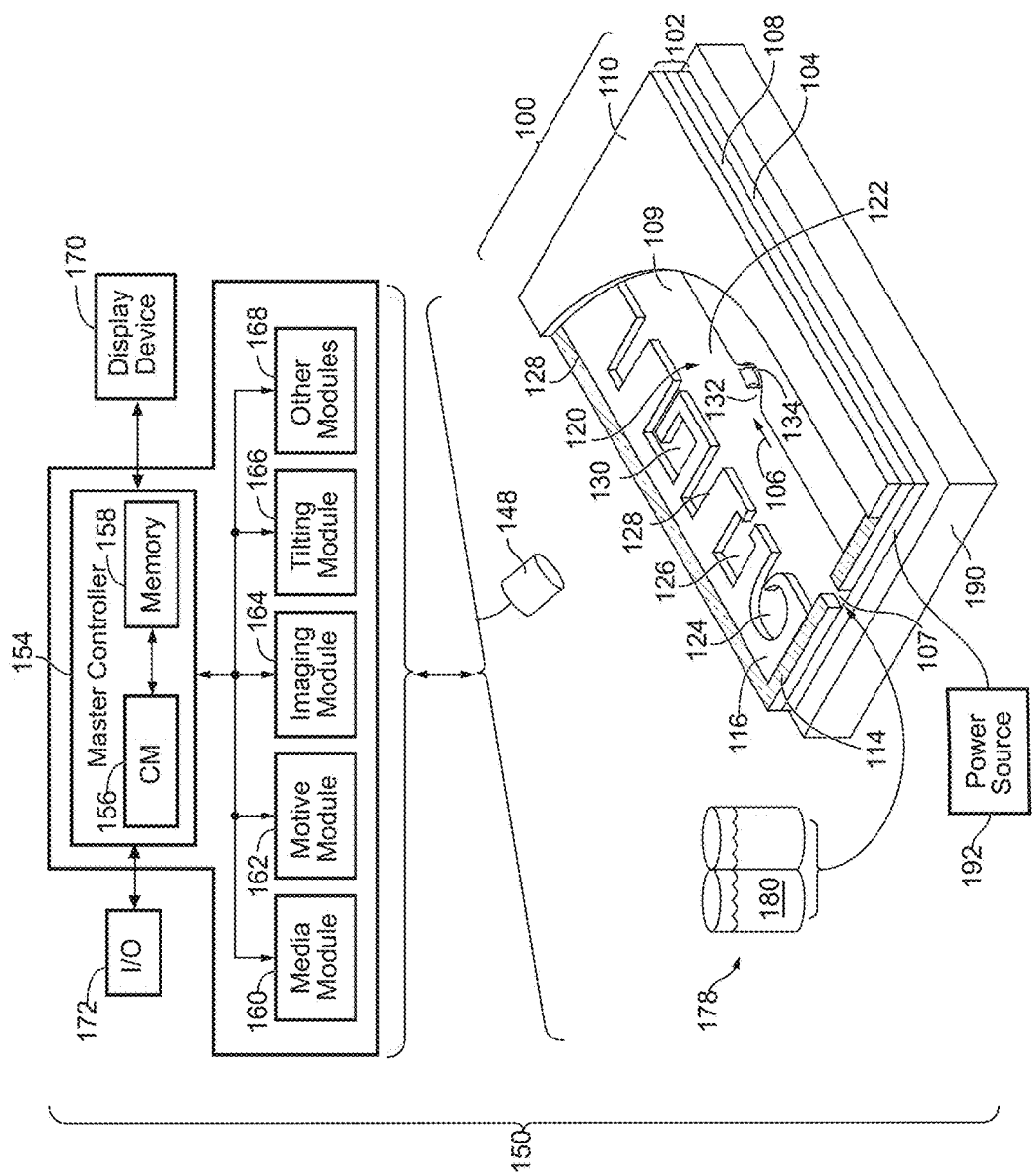
FIG. 1 illustrates an example of a system for use with a microfluidic device and associated control equipment according to some embodiments of the invention.

Microfluidic environments offer the opportunity to provide a cell or group of cells with a localized environment providing nutrients and/or soluble cell growth signaling species to the cell or group of cells in a time-dependent manner and location dependent concentration. These conditions may represent growing conditions more like that in vivo or, alternatively, permit perturbations to such typical conditions to permit study of and growth under nonstandard conditions. These requirements cannot be met using standardized macroscale cell culture methods. However, improvements are needed for more facile manipulation of a cell or cells to a) place the cell(s) into a microfluidic environment conducive to support cell growth, viability, portability, or any combination thereof; b) successfully maintain the cell(s) and/or expand the population of the cell(s); and/or c) define the conditions leading to successful growth and/or maintenance. The systems and methods described herein allow for more precise cell handling, environmental control, and cell isolation techniques for microfluidic cell culture, and may be used to produce, for example, clonal cell populations.

This specification describes exemplary embodiments and applications of the invention. The invention, however, is not limited to these exemplary embodiments and applications or to the manner in which the exemplary embodiments and applications operate or are described herein. Moreover, the Figures may show simplified or partial views, and the dimensions of elements in the Figures may be exaggerated or otherwise not in proportion for clarity. In addition, as the terms "on," "attached to," or "coupled to" are used herein, one element (e.g., a material, a layer, a substrate, etc.) can be "on," "attached to," or "coupled to" another element regardless of whether the one element is directly on, attached, or coupled to the other element or there are one or more intervening elements between the one element and the other element. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one. As used herein, the term "plurality" can be 2, 3, 4, 5, 6, 7, 8, 9, 10, or more.

As used herein, "air" refers to the composition of gases predominating in the atmosphere of the earth. The four most plentiful gases are nitrogen (typically present at a concentration of about 78% by volume, e.g., in a range from about 70-80%), oxygen (typically present at about 20.95% by volume at sea level, e.g. in a range from about 10% to about 25%), argon (typically present at about 1.0% by volume, e.g. in a range from about 0.1% to about 3%), and carbon dioxide (typically present at about 0.04%, e.g., in a range from about 0.01% to about 0.07%). Air may have other trace gases such as methane, nitrous oxide or ozone, trace pollutants and organic materials such as pollen, diesel particulates and the like. Air may include water vapor (typically present at about 0.25%, or may be present in a range from about 10 ppm to about 5% by volume). Air may be provided for use in culturing experiments as a filtered, controlled composition and may be conditioned as described herein.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least two ports configured to allow the fluid (and, optionally, micro-objects suspended in the fluid) to flow into and/or out of the microfluidic device. Typically, a microfluidic circuit of a microfluidic device will include at least one microfluidic channel and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 microliters. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 microliters.

As used herein, a "nanofluidic device" or "nanofluidic apparatus" is a type of microfluidic device having a microfluidic circuit that contains at least one circuit element configured to hold a volume of fluid of less than about 1 microliter, e.g., less than about 750, 500, 250, 200, 150, 100, 75, 50, 25, 20, 15, 10, 9, 8, 7, 6, 5, 4, 3, 2, 1 nL or less. Typically, a nanofluidic device will comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements are configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements are configured to hold a volume of fluid of about 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 300 times the length, at least 400 times the length, at least 500 times the length, or longer. In some embodiments, the length of a flow channel is in the range of from about 20,000 microns to about 100,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

As used herein, the term "obstruction" refers generally to a bump or similar type of structure that is sufficiently large so as to partially (but not completely) impede movement of target micro-objects between two different regions or circuit elements in a microfluidic device. The two different regions/ circuit elements can be, for example, a microfluidic incubation chamber and a microfluidic channel, or a connection region and an isolation region of a microfluidic incubation chamber.

As used herein, the term "constriction" refers generally to a narrowing of a width of a circuit element (or an interface between two circuit elements) in a microfluidic device. The constriction can be located, for example, at the interface between a microfluidic incubation chamber and a microfluidic channel, or at the interface between an isolation region and a connection region of a microfluidic incubation chamber.

As used herein, the term "transparent" refers to a material which allows visible light to pass through without substantially altering the light as is passes through.

As used herein, the term "micro-object" refers generally to any microscopic object that may be isolated and collected in accordance with the present invention. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells (e.g., embryos, oocytes, sperm cells, cells dissociated from a tissue, eukaryotic cells, protist cells, animal cells, mammalian cells, human cells, immunological cells including but not limited to T cells, B cells, Natural Killer Cells, Macrophages, Dendritic Cells and the like, hybridomas, cultured cells, cells from a cell line, cancer cells including but not limited to circulating tumor cells, infected cells, transfected and/or transformed cells including but not limited to CHO cells, reporter cells, prokaryotic cell, and the like); biological organelles (e.g. nuclei); vesicles, or complexes; synthetic vesicles; liposomes (e.g., synthetic or derived from membrane preparations); lipid nanorafts (as described in Ritchie et al. (2009) "Reconstitution of Membrane Proteins in Phospholipid Bilayer Nanodiscs," Methods Enzymol., 464:211-231), and the like; or a combination of inanimate micro-objects and biological micro-objects (e.g., microbeads attached to cells, liposome-coated microbeads, liposome-coated magnetic beads, or the like). Beads may further have other moieties/molecules covalently or non-covalently linked, such as fluorescent labels, proteins, small molecule signaling moieties, antigens, or chemical/biological species capable of use in an assay.

As used herein, the term "cell" refers to a biological cell, which can be a plant cell, an animal cell (e.g., a mammalian cell), a bacterial cell, a fungal cell, or the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. The term "clonal cells" refers to cells of the same clonal colony.

As used herein, "colony" of biological cells refers to 2 or more cells (e.g. 2-20, 4-40, 6-60, 8-80, 10-100, 20-200, 40-400, 60-600, 80-800, 100-1000, or greater than 1000 cells).

As used herein, the term "maintaining (a) cell(s)" refers to providing an environment comprising both fluidic and gaseous components that provide the conditions necessary to keep the cells viable and/or expanding.

As used herein, the term "expanding" when referring to cells, refers to increasing in cell number.

As referred to herein, "gas permeable" means that the material or structure is permeable to at least one of oxygen, carbon dioxide, or nitrogen. In some embodiments, the gas permeable material or structure is permeable to more than one of oxygen, carbon dioxide and nitrogen and may further be permeable to all three of these gases.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, when averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, a "non-sweeping" rate of fluidic medium flow means a rate of flow sufficient to permit components of a second fluidic medium in an isolation region of the growth chamber to diffuse into the first fluidic medium in the flow region and/or components of the first fluidic medium to diffuse into the second fluidic medium in the isolation region; and further wherein the first medium does not substantially flow into the isolation region.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

"Arylene" as used herein, refers to an aromatic radical with six to ten ring atoms (e.g., C6-C10 aromatic or C6-C10 aryl) which has at least one ring having a conjugated pi electron system which is carbocyclic (e.g., phenyl, fluorenyl, and naphthyl), and has one or two points of attachment to other portions of a molecule. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Examples of arylene include, but are not limited to, phenylene, naphthylene, and the like. An arylene moiety may be further substituted or may have no other substitutions other than the one or two points of attachment to the other parts of the molecule.

"Heteroarylene" as used herein, refers to a 5- to 18-membered aromatic radical (e.g., C5-C13 heteroaryl) that includes one or more ring heteroatoms selected from nitrogen, oxygen and sulfur, and which may include a monocyclic, bicyclic, tricyclic or tetracyclic ring system, and the -ene suffix indicates that the heteroaryl ring system has one or two points of attachment to other portions of a molecule. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical may optionally be oxidized. One or more nitrogen atoms, if present, may be optionally quaternized. The heteroaryl is attached to the rest of the molecule through any atom of the ring(s). Examples of heteroarylenes include, but are not limited to, benzimidazolylene, benzindolylene, isoxazolylene, thiazolylene, triazolylene, tetrazolylene, and thiophenylene (i.e. thienylene). A heteroarylene moiety may be further substituted or may have no other substitutions other than the one or two points of attachment to other parts of the molecule.

The term "heterocyclic" as used herein, refers to a substituted or unsubstituted 3-, 4-, 5-, 6-, or 7-membered saturated or partially unsaturated ring containing one, two, or three heteroatoms, preferably one or two heteroatoms independently selected from oxygen, nitrogen and sulfur; or to a bicyclic ring system containing up to 10 atoms including at least one heteroatom independently selected from oxygen, nitrogen, and sulfur wherein the ring containing the heteroatom is saturated. Examples of heterocyclyls include, but are not limited to, tetrahydrofuranyl, tetrahydrofuryl, pyrrolidinyl, piperidinyl, 4-pyranyl, tetrahydropyranyl, thiolanyl, morpholinyl, piperazinyl, dioxolanyl, dioxanyl, indolinyl, and 5-methyl-6-chromanyl. The heterocylic group may have one or two points of attachment to other parts of the molecule and may be further substituted or not further substituted.

System.

A system is provided for culturing one or more biological cells in a microfluidic device, including a microfluidic device comprising: a flow region configured to contain a flow of a first fluidic medium; and at least one growth chamber where the growth chamber has at least one surface conditioned to support cell growth, viability, portability, or any combination thereof.

Microfluidic Devices and Systems for Operating and Observing Such Devices.

FIG. 1 illustrates an example of a microfluidic device 100 and a system 150 which can be used in the practice of the present invention. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1, suitable microfluidic devices can include a plurality (e.g., 2 or 3) of such microfluidic circuits. Regardless, the microfluidic device 100 can be configured to be a nanofluidic device. In the embodiment illustrated in FIG. 1, the microfluidic circuit 120 comprises a plurality of microfluidic growth chambers 124, 126, 128, and 130, each having one or more openings in fluidic communication with flow path 106. As discussed further below, the microfluidic growth chambers comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1, the microfluidic circuit 120 is defined by an enclosure 102. Although the enclosure 102 can be physically structured in different configurations, in the example shown in FIG. 1 the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1 but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow channels, chambers, pens, traps, and the like. In the microfluidic circuit 120 illustrated in FIG. 1, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1 or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over growth chambers 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1 also shows a system 150 for operating and controlling microfluidic devices, such as microfluidic device 100. System 150, as illustrated, includes an electrical power source 192, an imaging device 194, and a tilting device 190.

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3, the imaging device 194 may further include a microscope (or an optical train), which may or may not include an eyepiece.

System 150 can further comprise a tilting device 190 configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more growth chambers. The term "above" as used herein denotes that the flow path 106 is positioned higher than the one or more growth chambers on a vertical axis defined by the force of gravity (i.e. an object in a growth chamber above a flow path 106 would have a higher gravitational potential energy than an object in the flow path). The term "below" as used herein denotes that the flow path 106 is positioned lower than the one or more growth chambers on a vertical axis defined by the force of gravity (i.e. an object in a growth chamber below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more growth chambers without being located directly above or below the growth chambers. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1. Alternatively, the media source 178 can be located in whole or in part inside the enclosure 102 of the microfluidic device 100. For example, the media source 178 can comprise reservoirs that are part of the microfluidic device 100.

FIG. 1 also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes, acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 2A and 2B, the enclosure 102 can comprise a dielectrophoresis (DEP), optoelectronic tweezers (OET) and/or opto-electrowetting (OEW) configuration (not shown in FIG. 1), and the motive module 162 can control the activation of electrodes and/or transistors (e.g., phototransistors) to select and move micro-objects (not shown) and/or droplets of medium (not shown) in the flow path 106 and/or growth chambers 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more growth chambers via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1, the microfluidic circuit 120 is illustrated as comprising a microfluidic channel 122 and growth chambers 124, 126, 128, 130. Each chamber comprises an opening to channel 122, but otherwise is enclosed such that the chambers can substantially isolate micro-objects inside the chamber from fluidic medium 180 and/or micro-objects in the flow path 106 of channel 122 or in other chambers. In some instances, chambers 124, 126, 128, 130 are configured to physically corral one or more micro-objects within the microfluidic circuit 120. Growth chambers in accordance with the present invention can comprise various shapes, surfaces and features that are optimized for use with DEP, OET, OEW, and/or gravitational forces, as will be discussed and shown in detail below.

The microfluidic circuit 120 may comprise any number of microfluidic growth chambers. Although five growth chambers are shown, microfluidic circuit 120 may have fewer or more growth chambers. In some embodiments, the microfluidic circuit 120 comprises a plurality of microfluidic growth chambers, wherein two or more of the growth chambers comprise differing structures and/or features.

In the embodiment illustrated in FIG. 1, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of growth chambers is configured (e.g., relative to a channel 122) such that they can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic growth chambers 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic growth chamber, such that upon tilting the microfluidic device 100 about an axis parallel to the channel 122, the trapped micro-object exits the trap 132 at a trajectory that causes the micro-object to fall into the opening of the growth chamber. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the growth chambers) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic growth chamber. In some embodiments, DEP forces are used to prevent a micro-object within a growth chamber (e.g., growth chamber 124, 126, 128, or 130) from being displaced therefrom. Further, in some embodiments, DEP forces are used to selectively remove a micro-object from a growth chamber that was previously collected in accordance with the teachings of the instant invention. In some embodiments, the DEP forces comprise optoelectronic tweezer (OET) forces.

In other embodiments, opto-electrowetting (OEW) forces are applied to one or more positions in the support structure 104 (and/or the cover 110) of the microfluidic device 100 (e.g., positions helping to define the flow path and/or the growth chambers) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic growth chamber. In some embodiments, OEW forces are used to prevent a droplet within a growth chamber (e.g., growth chamber 124, 126, 128, or 130) from being displaced therefrom. Further, in some embodiments, OEW forces are used to selectively remove a droplet from a growth chamber that was previously collected in accordance with the teachings of the instant invention.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic growth chambers, and the force of gravity can transport the micro-objects and/or droplets into the chambers. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 2A:
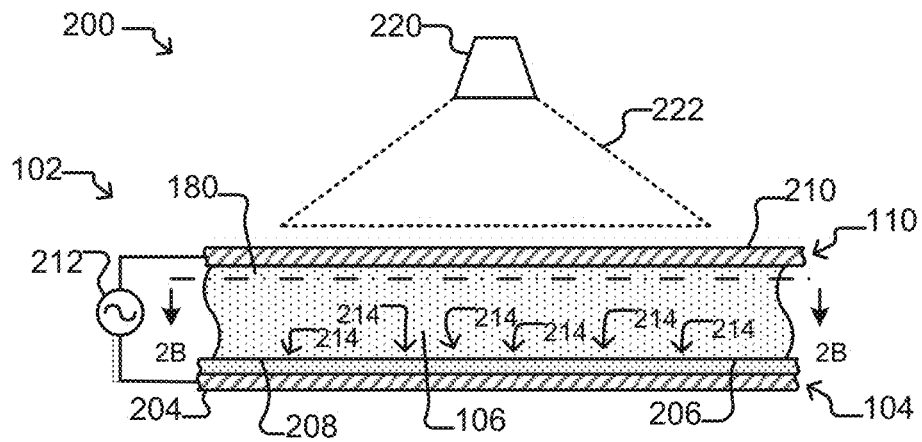
FIGS. 2A and 2B illustrate a microfluidic device according to some embodiments of the invention.

FIGS. 2A-2F illustrates various embodiments of microfluidic devices that can be used in the practice of the present invention. FIG. 2A depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an opto-electrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Motive Microfluidic Device Configurations.

As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 2B:
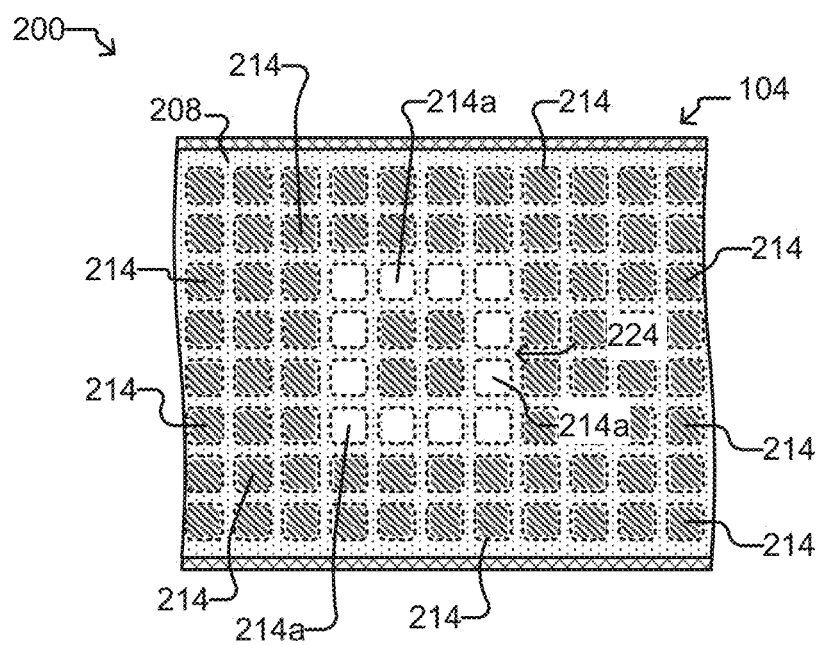

One example of a microfluidic device 200 comprising a DEP configuration is illustrated in FIGS. 2A and 2B. While for purposes of simplicity FIGS. 2A and 2B show a side cross-sectional view and a top cross-sectional view, respectively, of a portion of an enclosure 102 of the microfluidic device 200 having an open region/chamber 202, it should be understood that the region/chamber 202 may be part of a fluidic circuit element having a more detailed structure, such as a growth chamber, a flow region, or a flow channel. Furthermore, the microfluidic device 200 may include other fluidic circuit elements. For example, the microfluidic device 200 can include a plurality of growth chambers and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 2A, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 2A and 2B can have an optically-actuated DEP configuration. Accordingly, changing patterns of light 222 from the light source 220, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 2B, a light pattern 222 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 222 projected from a light source 220 into the microfluidic device 200. Whether the DEP forces attract or repel nearby micro-objects can depend on such parameters as the frequency of the power source 212 and the dielectric properties of the medium 180 and/or micro-objects (not shown).

The square pattern 224 of illuminated DEP electrode regions 214a illustrated in FIG. 2B is an example only. Any pattern of the DEP electrode regions 214 can be illuminated (and thereby activated) by the pattern of light 222 projected into the device 200, and the pattern of illuminated/activated DEP electrode regions 214 can be repeatedly changed by changing or moving the light pattern 222.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 microns. In such embodiments, the DEP electrode regions 214 can be created anywhere and in any pattern on the inner surface 208 of the electrode activation substrate 206, in accordance with the light pattern 222. The number and pattern of the DEP electrode regions 214 thus need not be fixed, but can correspond to the light pattern 222. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 222. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 222, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 222.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 220 can alternatively be used to illuminate the enclosure 102 from below.

With the microfluidic device 200 of FIGS. 2A-2B having a DEP configuration, the motive module 162 can select a micro-object (not shown) in the medium 180 in the region/chamber 202 by projecting a light pattern 222 into the device 200 to activate a first set of one or more DEP electrodes at DEP electrode regions 214a of the inner surface 208 of the electrode activation substrate 206 in a pattern (e.g., square pattern 224) that surrounds and captures the micro-object. The motive module 162 can then move the captured micro-object by moving the light pattern 222 relative to the device 200 to activate a second set of one or more DEP electrodes at DEP electrode regions 214. Alternatively, the device 200 can be moved relative to the light pattern 222.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 224), one or more micro-objects in region/chamber 202 can be trapped and moved within the region/chamber 202. The motive module 162 in FIG. 1 can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently linked to the surface of the dielectric layer. For example, molecules of the hydrophobic material can be covalently linked to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 nm to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 microns. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 222 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 222 (or moving microfluidic device 200 relative to the light source 220) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1 can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Growth Chambers.

Figure 2C:
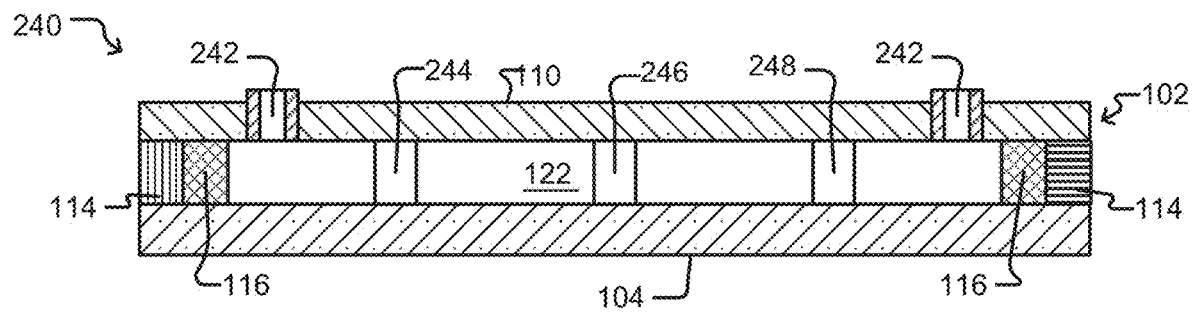
FIGS. 2C and 2D illustrate growth chambers according to some embodiments of the invention.
Figure 2D:
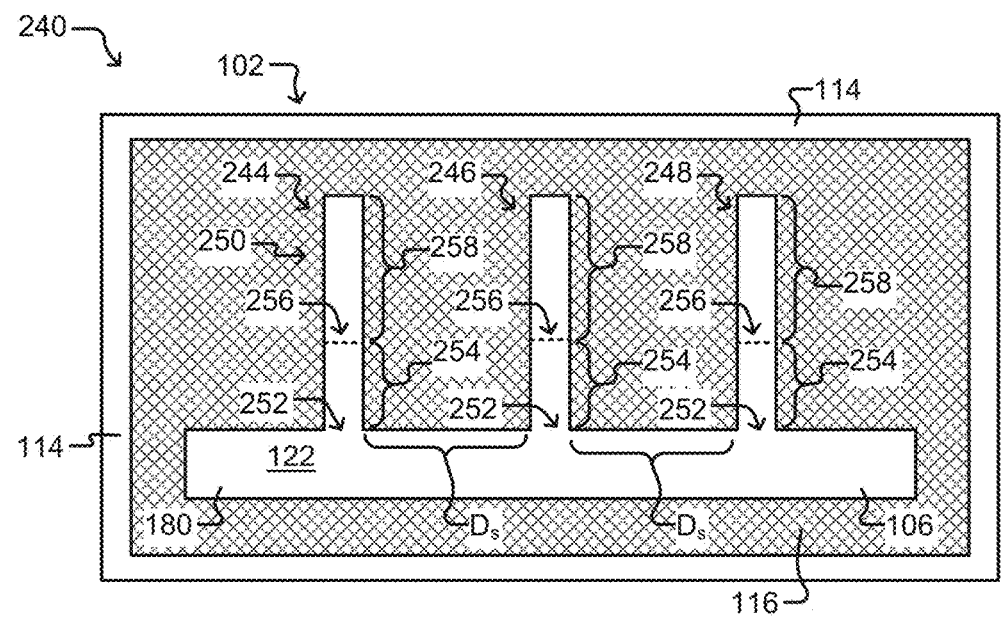

Non-limiting examples of generic growth chambers 244, 246, and 248 are shown within the microfluidic device 240 depicted in FIGS. 2C and 2D. Each growth chamber 244, 246, and 248 can comprise an isolation structure 250 defining an isolation region 258 and a connection region 254 fluidically connecting the isolation region 258 to a channel 122. The connection region 254 can comprise a proximal opening 252 to the channel 122 and a distal opening 256 to the isolation region 258. The connection region 254 can be configured so that the maximum penetration depth of a flow of a fluidic medium (not shown) flowing from the channel 122 into the growth chamber 244, 246, 248 does not extend into the isolation region 258. Thus, due to the connection region 254, a micro-object (not shown) or other material (not shown) disposed in an isolation region 258 of a growth chamber 244, 246, 248 can thus be isolated from, and not substantially affected by, a flow of medium 180 in the channel 122.

The channel 122 can thus be an example of a swept region, and the isolation regions 258 of the growth chambers 244, 246, 248 can be examples of unswept regions. As noted, the channel 122 and growth chambers 244, 246, 248 can be configured to contain one or more fluidic media 180. In the example shown in FIGS. 2C-2D, the ports 242 are connected to the channel 122 and allow a fluidic medium 180 to be introduced into or removed from the microfluidic device 240. Prior to introduction of the fluidic medium 180, the microfluidic device may be primed with a gas such as carbon dioxide gas. Once the microfluidic device 240 contains the fluidic medium 180, the flow 260 of fluidic medium 180 in the channel 122 can be selectively generated and stopped. For example, as shown, the ports 242 can be disposed at different locations (e.g., opposite ends) of the channel 122, and a flow 260 of medium can be created from one port 242 functioning as an inlet to another port 242 functioning as an outlet.

Figure 2E:
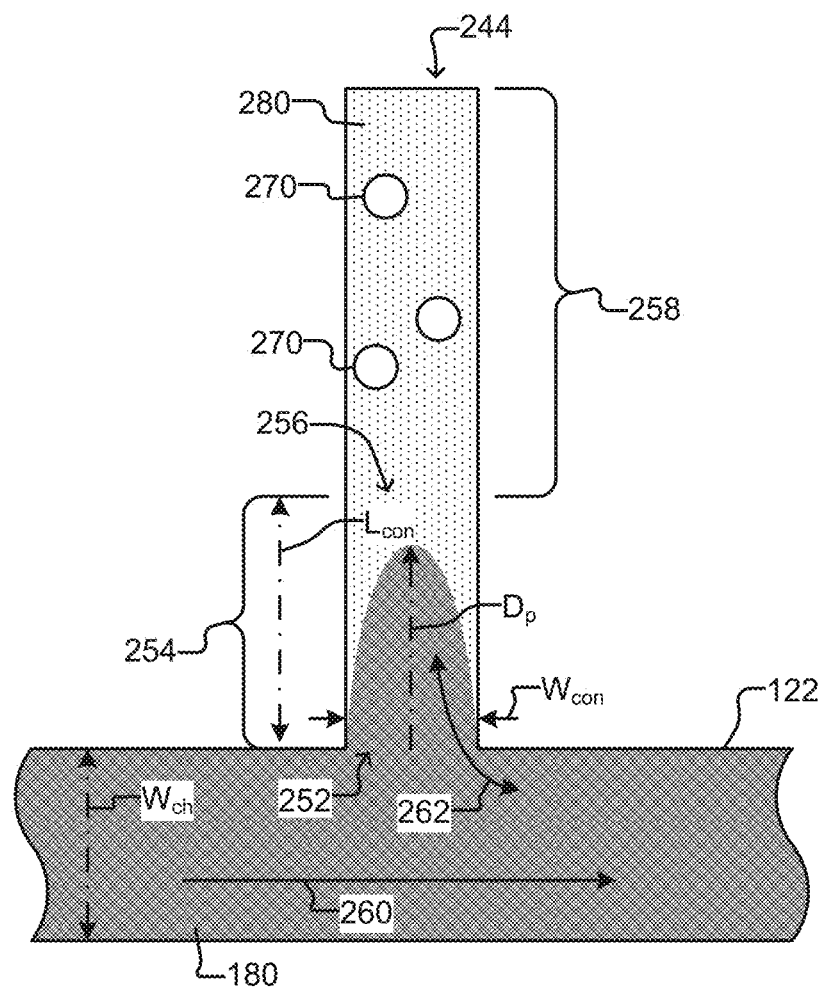
FIG. 2E illustrates a detailed growth chamber according to some embodiments of the invention.

FIG. 2E illustrates a detailed view of an example of a growth chamber 244 according to the present invention. Examples of micro-objects 270 are also shown.

As is known, a flow 260 of fluidic medium 180 in a microfluidic channel 122 past a proximal opening 252 of a growth chamber 244 can cause a secondary flow 262 of the medium 180 into and/or out of the growth chamber 244. To isolate micro-objects 270 in the isolation region 258 of a growth chamber 244 from the secondary flow 262, the length $L_{con}$ of the connection region 254 of the growth chamber 244 (i.e., from the proximal opening 252 to the distal opening 256) should be greater than the penetration depth $D_p$ of the secondary flow 262 into the connection region 254. The penetration depth $D_p$ of the secondary flow 262 depends upon the velocity of the fluidic medium 180 flowing in the channel 122 and various parameters relating to the configuration of the channel 122 and the proximal opening 252 of the connection region 254 to the channel 122. For a given microfluidic device, the configurations of the channel 122 and the opening 252 will be fixed, whereas the rate of flow 260 of fluidic medium 180 in the channel 122 will be variable. Accordingly, for each growth chamber 244, a maximal velocity Vmax for the flow 260 of fluidic medium 180 in channel 122 can be identified that ensures that the penetration depth $D_p$ of the secondary flow 262 does not exceed the length $L_{con}$ of the connection region 254. As long as the rate of the flow 260 of fluidic medium 180 in the channel 122 does not exceed the maximum velocity Vmax, the resulting secondary flow 262 can be limited to the channel 122 and the connection region 254 and kept out of the isolation region 258. The flow 260 of medium 180 in the channel 122 will thus not draw micro-objects 270 out of the isolation region 258. Rather, micro-objects 270 located in the isolation region 258 will stay in the isolation region 258 regardless of the flow 260 of fluidic medium 180 in the channel 122.

Moreover, as long as the rate of flow 260 of medium 180 in the channel 122 does not exceed Vmax, the flow 260 of fluidic medium 180 in the channel 122 will not move miscellaneous particles (e.g., microparticles and/or nanoparticles) from the channel 122 into the isolation region 258 of a growth chamber 244. Having the length $L_{con}$ of the connection region 254 be greater than the maximum penetration depth $D_p$ of the secondary flow 262 can thus prevent contamination of one growth chamber 244 with miscellaneous particles from the channel 122 or another growth chamber (e.g., growth chambers 246, 248 in FIG. 2D).

Because the channel 122 and the connection regions 254 of the growth chambers 244, 246, 248 can be affected by the flow 260 of medium 180 in the channel 122, the channel 122 and connection regions 254 can be deemed swept (or flow) regions of the microfluidic device 240. The isolation regions 258 of the growth chambers 244, 246, 248, on the other hand, can be deemed unswept (or non-flow) regions. For example, components (not shown) in a first fluidic medium 180 in the channel 122 can mix with a second fluidic medium 280 in the isolation region 258 substantially only by diffusion of components of the first medium 180 from the channel 122 through the connection region 254 and into the second fluidic medium 280 in the isolation region 258. Similarly, components (not shown) of the second medium 280 in the isolation region 258 can mix with the first medium 180 in the channel 122 substantially only by diffusion of components of the second medium 280 from the isolation region 258 through the connection region 254 and into the first medium 180 in the channel 122. The first medium 180 can be the same medium or a different medium than the second medium 280. Moreover, the first medium 180 and the second medium 280 can start out being the same, then become different (e.g., through conditioning of the second medium 280 by one or more cells in the isolation region 258, or by changing the medium 180 flowing through the channel 122).

The maximum penetration depth $D_p$ of the secondary flow 262 caused by the flow 260 of fluidic medium 180 in the channel 122 can depend on a number of parameters, as mentioned above. Examples of such parameters include: the shape of the channel 122 (e.g., the channel can direct medium into the connection region 254, divert medium away from the connection region 254, or direct medium in a direction substantially perpendicular to the proximal opening 252 of the connection region 254 to the channel 122); a width $W_{ch}$ (or cross-sectional area) of the channel 122 at the proximal opening 252; and a width $W_{con}$ (or cross-sectional area) of the connection region 254 at the proximal opening 252; the velocity V of the flow 260 of fluidic medium 180 in the channel 122; the viscosity of the first medium 180 and/or the second medium 280, or the like.

In some embodiments, the dimensions of the channel 122 and growth chambers 244, 246, 248 can be oriented as follows with respect to the vector of the flow 260 of fluidic medium 180 in the channel 122: the channel width $W_{ch}$ (or cross-sectional area of the channel 122) can be substantially perpendicular to the flow 260 of medium 180; the width $W_{con}$ (or cross-sectional area) of the connection region 254 at opening 252 can be substantially parallel to the flow 260 of medium 180 in the channel 122; and/or the length $L_{con}$ of the connection region can be substantially perpendicular to the flow 260 of medium 180 in the channel 122. The foregoing are examples only, and the relative position of the channel 122 and growth chambers 244, 246, 248 can be in other orientations with respect to each other.

As illustrated in FIG. 2E, the width $W_{con}$ of the connection region 254 can be uniform from the proximal opening 252 to the distal opening 256. The width $W_{con}$ of the connection region 254 at the distal opening 256 can thus be in any of the ranges identified herein for the width $W_{con}$ of the connection region 254 at the proximal opening 252. Alternatively, the width $W_{con}$ of the connection region 254 at the distal opening 256 can be larger than the width $W_{con}$ of the connection region 254 at the proximal opening 252.

As illustrated in FIG. 2E, the width of the isolation region 258 at the distal opening 256 can be substantially the same as the width $W_{con}$ of the connection region 254 at the proximal opening 252. The width of the isolation region 258 at the distal opening 256 can thus be in any of the ranges identified herein for the width $W_{con}$ of the connection region 254 at the proximal opening 252. Alternatively, the width of the isolation region 258 at the distal opening 256 can be larger or smaller than the width $W_{con}$ of the connection region 254 at the proximal opening 252. Moreover, the distal opening 256 may be smaller than the proximal opening 252 and the width $W_{con}$ of the connection region 254 may be narrowed between the proximal opening 252 and distal opening 256. For example, the connection region 254 may be narrowed between the proximal opening and the distal opening, using a variety of different geometries (e.g. chamfering the connection region, beveling the connection region). Further, any part or subpart of the connection region 254 may be narrowed (e.g. a portion of the connection region adjacent to the proximal opening 252).

Figure 4A:
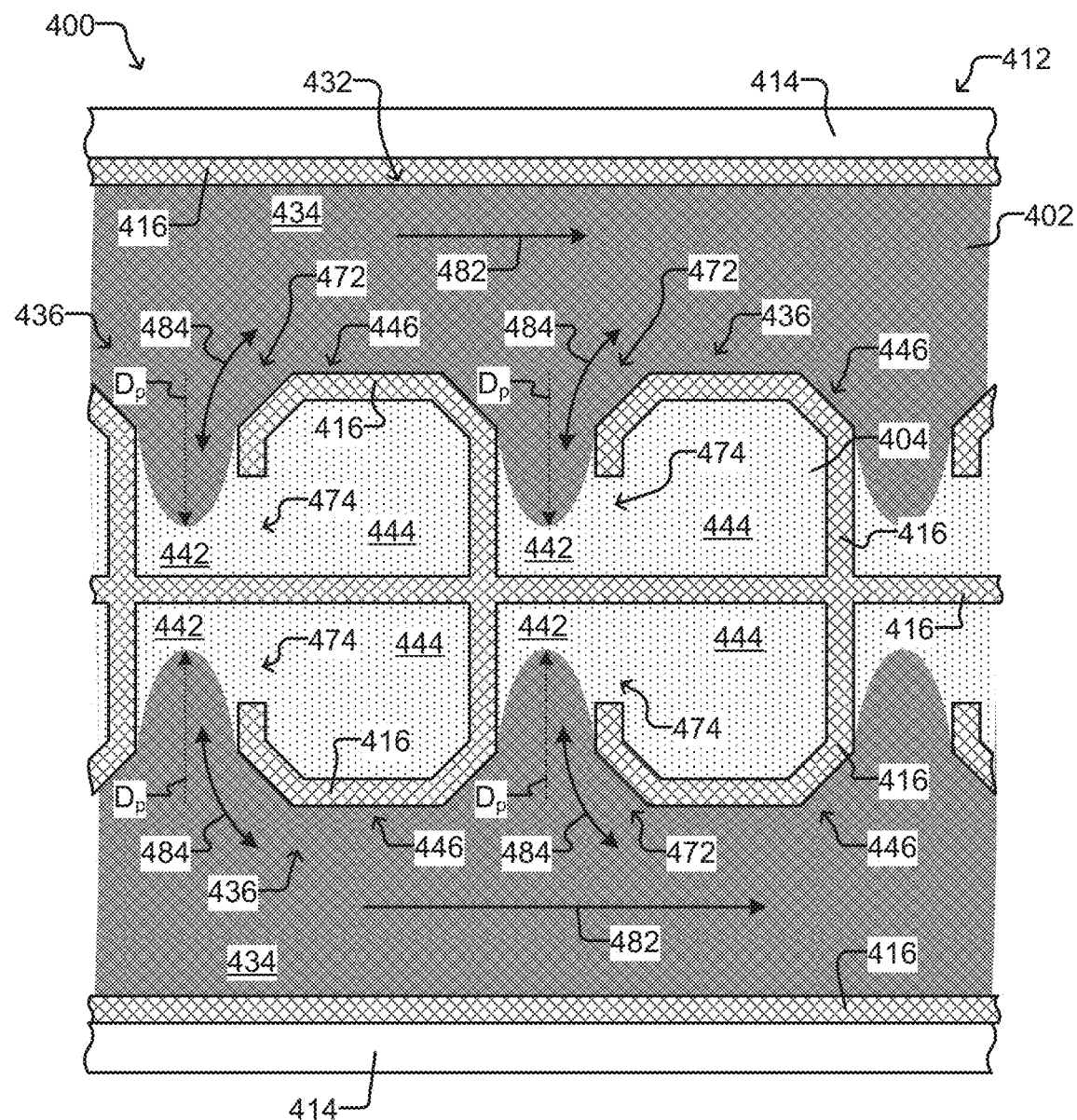
FIGS. 4A-C show another embodiment of a microfluidic device, including a further example of a growth chamber used therein.
Figure 4B:
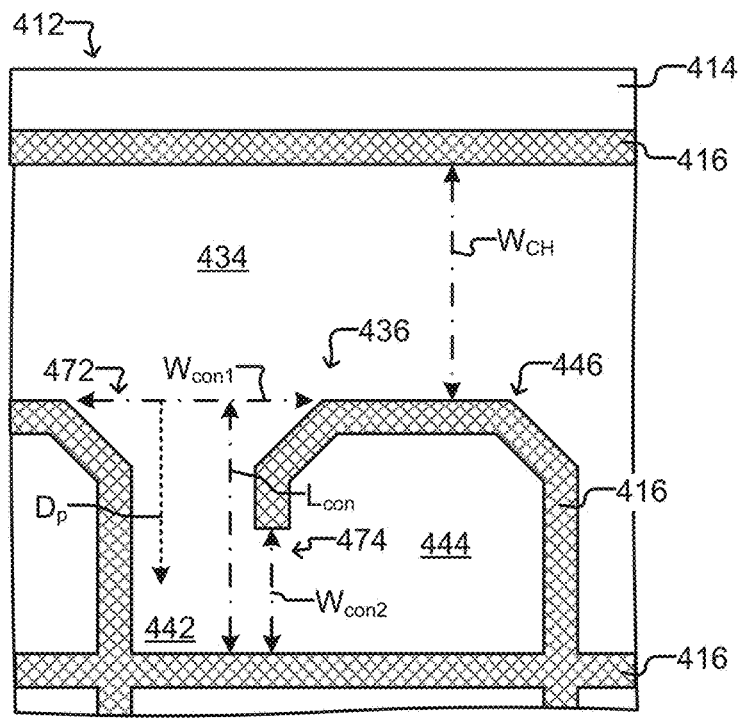
Figure 4C:
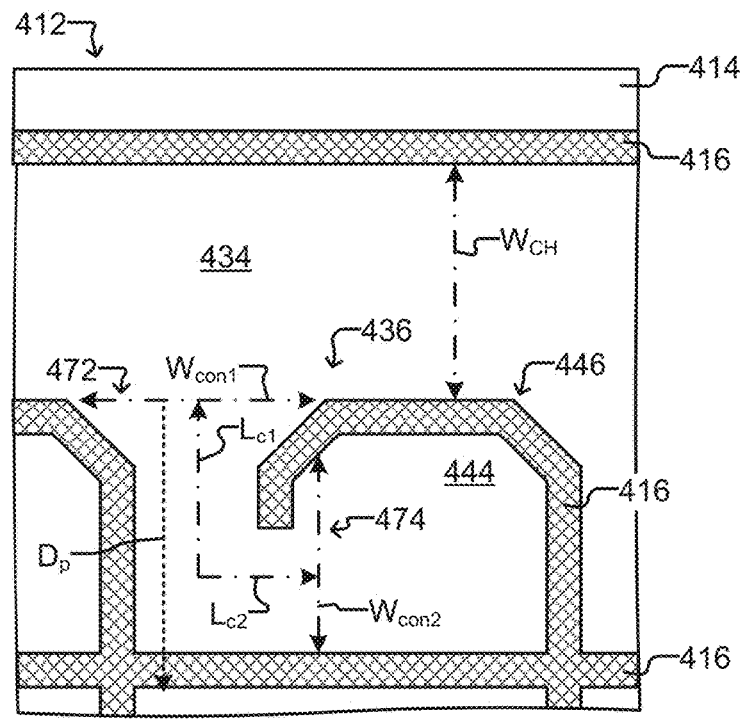

FIGS. 4A-C depict another exemplary embodiment of a microfluidic device 400 containing a microfluidic circuit 432 and flow channels 434, which are variations of the respective microfluidic device 100, circuit 132 and channel 134 of FIG. 1. The microfluidic device 400 also has a plurality of growth chambers 436 that are additional variations of the above-described growth chambers 124, 126, 128, 130, 244, 246 or 248. In particular, it should be appreciated that the growth chambers 436 of device 400 shown in FIGS. 4A-C can replace any of the above-described growth chambers 124, 126, 128, 130, 244, 246 or 248 in devices 100, 200, 240 and 290. Likewise, the microfluidic device 400 is another variant of the microfluidic device 100, and may also have the same or a different DEP configuration as the above-described microfluidic device 100, 200, 240, 290, as well as any of the other microfluidic system components described herein.

The microfluidic device 400 of FIGS. 4A-C comprises a support structure (not visible in FIGS. 4A-C, but can be the same or generally similar to the support structure 104 of device 100 depicted in FIG. 1), a microfluidic circuit structure 412, and a cover (not visible in FIGS. 4A-C, but can be the same or generally similar to the cover 110 of device 100 depicted in FIG. 1). The microfluidic circuit structure 412 includes a frame 414 and microfluidic circuit material 416, which can be the same as or generally similar to the frame 114 and microfluidic circuit material 116 of device 100 shown in FIG. 1. As shown in FIG. 4A, the microfluidic circuit 432 defined by the microfluidic circuit material 416 can comprise multiple channels 434 (two are shown but there can be more) to which multiple growth chambers 436 are fluidically connected.

Each growth chamber 436 can comprise an isolation structure 446, an isolation region 444 within the isolation structure 446, and a connection region 442. From a proximal opening 472 at the channel 434 to a distal opening 474 at the isolation structure 436, the connection region 442 fluidically connects the channel 434 to the isolation region 444. Generally, in accordance with the above discussion of FIGS. 2D and 2E, a flow 482 of a first fluidic medium 402 in a channel 434 can create secondary flows 484 of the first medium 402 from the channel 434 into and/or out of the respective connection regions 442 of the growth chambers 436.

As illustrated in FIG. 4B, the connection region 442 of each growth chamber 436 generally includes the area extending between the proximal opening 472 to a channel 434 and the distal opening 474 to an isolation structure 446. The length $L_{con}$ of the connection region 442 can be greater than the maximum penetration depth $D_p$ of secondary flow 484, in which case the secondary flow 484 will extend into the connection region 442 without being redirected toward the isolation region 444 (as shown in FIG. 4A). Alternatively, as illustrated in FIG. 4C, the connection region 442 can have a length $L_{con}$ that is less than the maximum penetration depth $D_p$, in which case the secondary flow 484 will extend through the connection region 442 and be redirected toward the isolation region 444. In this latter situation, the sum of lengths $L_{c1}$ and $L_{c2}$ of connection region 442 is greater than the maximum penetration depth $D_p$, so that secondary flow 484 will not extend into isolation region 444. Whether length $L_{con}$ of connection region 442 is greater than the penetration depth $D_p$, or the sum of lengths $L_{c1}$ and $L_{c2}$ of connection region 442 is greater than the penetration depth $D_p$, a flow 482 of a first medium 402 in channel 434 that does not exceed a maximum velocity $V_{max}$ will produce a secondary flow having a penetration depth $D_p$, and micro-objects (not shown but can be the same or generally similar to the micro-objects 270 shown in FIG. 2E) in the isolation region 444 of a growth chamber 436 will not be drawn out of the isolation region 444 by a flow 482 of first medium 402 in channel 434. Nor will the flow 482 in channel 434 draw miscellaneous materials (not shown) from channel 434 into the isolation region 444 of a growth chamber 436. As such, diffusion is the only mechanism by which components in a first medium 402 in the channel 434 can move from the channel 434 into a second medium 404 in an isolation region 444 of a growth chamber 436. Likewise, diffusion is the only mechanism by which components in a second medium 404 in an isolation region 444 of a growth chamber 436 can move from the isolation region 444 to a first medium 402 in the channel 434. The first medium 402 can be the same medium as the second medium 404, or the first medium 402 can be a different medium than the second medium 404. Alternatively, the first medium 402 and the second medium 404 can start out being the same, then become different, e.g., through conditioning of the second medium by one or more cells in the isolation region 444, or by changing the medium flowing through the channel 434.

As illustrated in FIG. 4B, the width $W_{ch}$ of the channels 434 (i.e., taken transverse to the direction of a fluid medium flow through the channel indicated by arrows 482 in FIG. 4A) in the channel 434 can be substantially perpendicular to a width $W_{con1}$ of the proximal opening 472 and thus substantially parallel to a width $W_{con2}$ the distal opening 474. The width $W_{con1}$ of the proximal opening 472 and the width $W_{con2}$ the distal opening 474, however, need not be substantially perpendicular to other. For example, an angle between an axis (not shown) on which the width $W_{con1}$ of the proximal opening 472 is oriented and another axis on which the width $W_{con2}$ of distal the opening 474 is oriented can be other than perpendicular and thus other 90°. Examples of alternatively oriented angles include angles in any of the following ranges: from about 30° to about 90°, from about 45° to about 90°, from about 60° to about 90°, or the like.

In various embodiments of growth chambers (e.g. 124, 126, 128, 130, 244, 246,248, or 436), the isolation region (e.g. 258 or 444) is configured to contain a plurality of micro-objects. In other embodiments, the isolation region can be configured to contain only one, two, three, four, five, or a similar relatively small number of micro-objects. Accordingly, the volume of an isolation region can be, for example, at least $3 \times 10^3$, $6 \times 10^3$, $9 \times 10^3$, $1 \times 10^4$, $2 \times 10^4$, $4 \times 10^4$, $8 \times 10^4$, $1 \times 10^5$, $2 \times 10^5$, $4 \times 10^5$, $8 \times 10^5$, $1 \times 10^6$, $2 \times 10^6$, $4 \times 10^6$, $6 \times 10^6$, $1 \times 10^7$, $2 \times 10^7$, $4 \times 10^7$, $6 \times 10^7$, $1 \times 10^8$, cubic microns, or more.

In various embodiments of growth chambers, the width $W_{ch}$ of the channel 122, 434 at a proximal opening (e.g. 252, 472) can be within any of the following ranges: 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. The foregoing are examples only, and the width $W_{ch}$ of the channel 122, 434 can be in other ranges (e.g., a range defined by any of the endpoints listed above). Moreover, the $W_{ch}$ of the channel 122, 434 can be selected to be in any of these ranges in regions of the channel other than at a proximal opening of a growth chamber.

In some embodiments, a growth chamber has a cross-sectional height of about 30 to about 200 microns, or about 50 to about 150 microns. In some embodiments, the growth chamber has a cross-sectional area of about 100,000 to about 2,500,000 square microns, or about 200,000 to about 2,000,000 square microns. In some embodiments, a connection region has a cross-sectional height that matches the cross-sectional height of the corresponding growth chamber. In some embodiments, the connection region has a cross-sectional width of about 50 to about 500 microns, or about 100 to about 300 microns.

In various embodiments of growth chambers the height $H_{ch}$ of the channel 122, 434 at a proximal opening 252, 472 can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the channel 122, 434 can be in other ranges (e.g., a range defined by any of the endpoints listed above). The height $H_{ch}$ of the channel 122, 434 can be selected to be in any of these ranges in regions of the channel other than at a proximal opening of a growth chamber.

In various embodiments of growth chambers a cross-sectional area of the channel 122, 434 at a proximal opening 252, 472 can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the channel 122 at a proximal opening 252, 472 can be in other ranges (e.g., a range defined by any of the endpoints listed above).

In various embodiments of growth chambers, the length $L_{con}$ of the connection region 254, 442 can be in any of the following ranges: 1-200 microns, 5-150 microns, 10-100 microns, 15-80 microns, 20-60 microns, 20-500 microns, 40-400 microns, 60-300 microns, 80-200 microns, and 100-150 microns. The foregoing are examples only, and length $L_{con}$ of a connection region 254, 442 can be in a different range than the foregoing examples (e.g., a range defined by any of the endpoints listed above).

In various embodiments of growth chambers the width $W_{con}$ of a connection region 254, 442 at a proximal opening 252 can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region 254, 442 at a proximal opening 252 can be different than the foregoing examples (e.g., a range defined by any of the endpoints listed above).

In various embodiments of growth chambers the width $W_{con}$ of a connection region 254, 442 at a proximal opening 252, 472 can be in any of the following ranges: 2-35 microns, 2-25 microns, 2-20 microns, 2-15 microns, 2-10 microns, 2-7 microns, 2-5 microns, 2-3 microns, 3-25 microns, 3-20 microns, 3-15 microns, 3-10 microns, 3-7 microns, 3-5 microns, 3-4 microns, 4-20 microns, 4-15 microns, 4-10 microns, 4-7 microns, 4-5 microns, 5-15 microns, 5-10 microns, 5-7 microns, 6-15 microns, 6-10 microns, 6-7 microns, 7-15 microns, 7-10 microns, 8-15 microns, and 8-10 microns. The foregoing are examples only, and the width $W_{con}$ of a connection region 254, 442 at a proximal opening 252, 472 can be different than the foregoing examples (e.g., a range defined by any of the endpoints listed above).

In various embodiments of growth chambers, a ratio of the length $L_{con}$ of a connection region 254, 442 to a width $W_{con}$ of the connection region 254, 442 at the proximal opening 252, 472 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 254 to a width $W_{con}$ of the connection region 254, 442 at the proximal opening 252, 472 can be different than the foregoing examples.

In various embodiments of microfluidic devices 100, 200, 240, 290, 400, $V_{max}$ can be set around 0.2, 0.3, 0.4, 0.5, 0.6, 0.7, 0.8, 0.9, 1.0, 1.1, 1.2, 1.3, 1.4, or 1.5 microliters/sec. In some other embodiments. Alternatively, $V_{max}$ can be set at about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 microliters/sec. In yet other embodiments, $V_{max}$ can be set at or about 2.0, 2.2, 2.4, 2.6, 2.8, 3.0, 3.2, 3.4, 3.6, 3.8, 4.0, 4.2, 4.4, 4.6, 4.8, 5.0, 6.0, 7.0, 8.0 or about 9.0 microliters/sec.

In various embodiments of microfluidic devices having growth chambers, the volume of an isolation region 258, 444 of a growth chamber can be, for example, at least $3\times10^3$, $6\times10^3$, $9\times10^3$, $1\times10^4$, $2\times10^4$, $4\times10^4$, $8\times10^4$, $1\times10^5$, $2\times10^5$, $4\times10^5$, $8\times10^5$, $1\times10^6$, $2\times10^6$, $4\times10^6$, $6\times10^6$ cubic microns, or more. In various embodiments of microfluidic devices having growth chambers, the volume of a growth chamber may be about $5\times10^3$, $7\times10^3$, $1\times10^4$, $3\times10^4$, $5\times10^4$, $8\times10^4$, $1\times10^5$, $2\times10^5$, $4\times10^5$, $6\times10^5$, $8\times10^5$, $1\times10^6$, $2\times10^6$, $4\times10^6$, $8\times10^6$, $1\times10^7$, $3\times10^7$, $5\times10^7$, or about $8\times10^7$ cubic microns, or more. In some embodiments, the microfluidic device has growth chambers wherein no more than $1\times10^2$ biological cells may be maintained, and the volume of a growth chamber may be no more than $2\times10^6$ cubic microns. In some embodiments, the microfluidic device has growth chambers wherein no more than $1\times10^2$ biological cells may be maintained, and a growth chamber may be no more than $4\times10^5$ cubic microns. In yet other embodiments, the microfluidic device has growth chambers wherein no more than 50 biological cells may be maintained, a growth chamber may be no more than $4\times10^5$ cubic microns.

In various embodiment, the microfluidic device has growth chambers configured as in any of the embodiments discussed herein where the microfluidic device has about 100 to about 500 growth chambers; about 200 to about 1000 growth chambers, about 500 to about 1500 growth chambers, about 1000 to about 2000 growth chambers, or about 1000 to about 3500 growth chambers.

In some other embodiments, the microfluidic device has growth chambers configured as in any of the embodiments discussed herein where the microfluidic device has about 1500 to about 3000 growth chambers, about 2000 to about 3500 growth chambers, about 2500 to about 4000 growth chambers, about 3000 to about 4500 growth chambers, about 3500 to about 5000 growth chambers, about 4000 to about 5500 growth chambers, about 4500 to about 6000 growth chambers, about 5000 to about 6500 growth chambers, about 5500 to about 7000 growth chambers, about 6000 to about 7500 growth chambers, about 6500 to about 8000 growth chambers, about 7000 to about 8500 growth chambers, about 7500 to about 9000 growth chambers, about 8000 to about 9500 growth chambers, about 8500 to about 10,000 growth chambers, about 9000 to about 10,500 growth chambers, about 9500 to about 11,000 growth chambers, about 10,000 to about 11,500 growth chambers, about 10,500 to about 12,000 growth chambers, about 11,000 to about 12,500 growth chambers, about 11,500 to about 13,000 growth chambers, about 12,000 to about 13,500 growth chambers, about 12,500 to about 14,000 growth chambers, about 13,000 to about 14,500 growth chambers, about 13,500 to about 15,000 growth chambers, about 14,000 to about 15,500 growth chambers, about 14,500 to about 16,000 growth chambers, about 15,000 to about 16,500 growth chambers, about 15,500 to about 17,000 growth chambers, about 16,000 to about 17,500 growth chambers, about 16,500 to about 18,000 growth chambers, about 17,000 to about 18,500 growth chambers, about 17,500 to about 19,000 growth chambers, about 18,000 to about 19,500 growth chambers, about 18,500 to about 20,000 growth chambers, about 19,000 to about 20,500 growth chambers, about 19,500 to about 21,000 growth chambers, or about 20,000 to about 21,500 growth chambers.

Figure 2F:
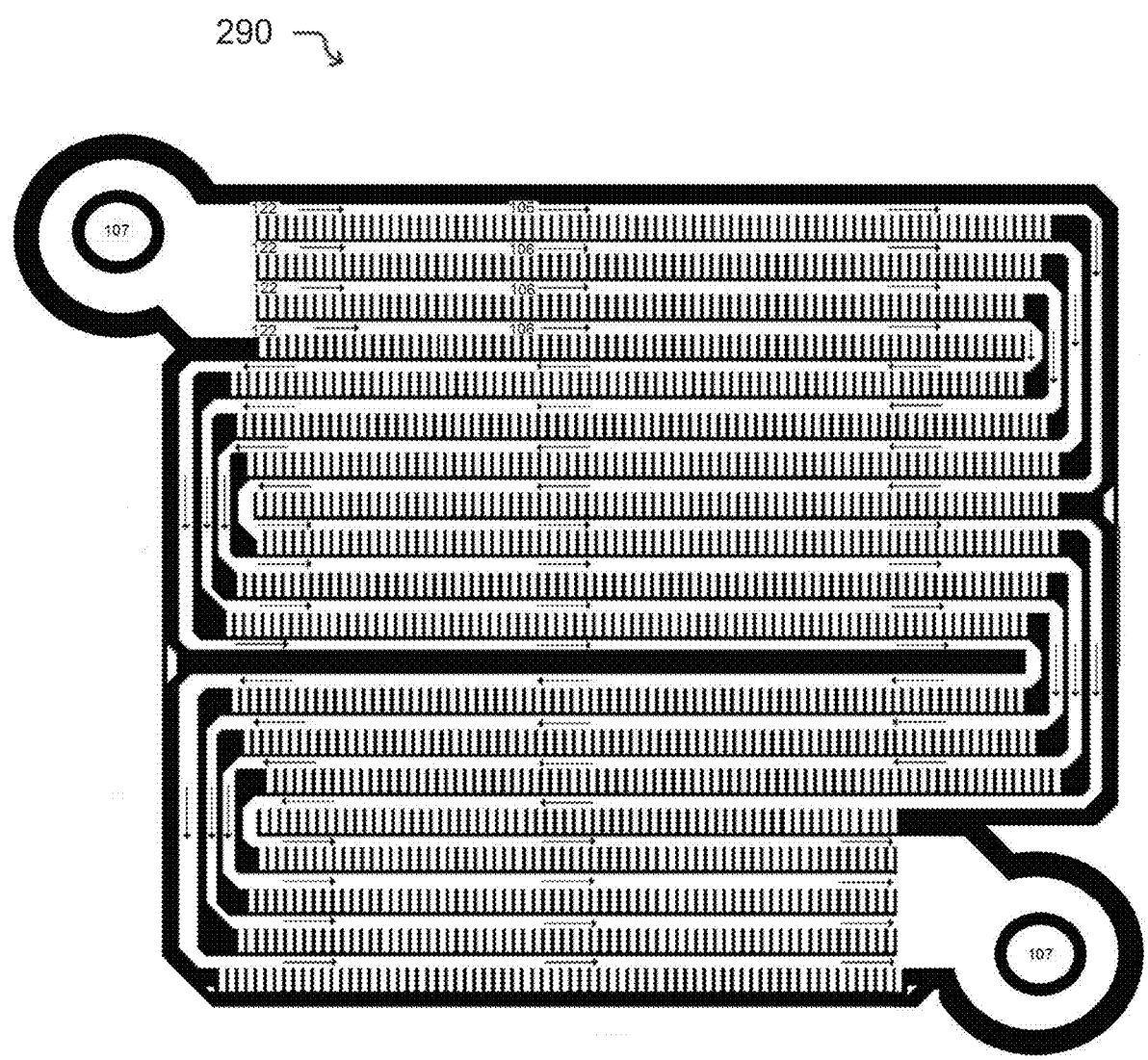
FIG. 2F illustrates a microfluidic device according to an embodiment of the invention.

FIG. 2F illustrates a microfluidic device 290 according to one embodiment. The microfluidic device 290 illustrated in FIG. 2F is a stylized diagram of a microfluidic device 100. In practice the microfluidic device 290 and its constituent circuit elements (e g channels 122 and growth chambers 128) would have the dimensions discussed herein. The microfluidic circuit 120 illustrated in FIG. 2F has two ports 107, four distinct channels 122 and four distinct flow paths 106. The microfluidic device 290 further comprises a plurality of growth chambers opening off of each channel 122. In the microfluidic device illustrated in FIG. 2F, the growth chambers have a geometry similar to the pens illustrated in FIG. 2E and thus, have both connection regions and isolation regions. Accordingly, the microfluidic circuit 120 includes both swept regions (e.g. channels 122 and portions of the connection regions 254 within the maximum penetration depth $D_p$ of the secondary flow 262) and non-swept regions (e.g. isolation regions 258 and portions of the connection regions 254 not within the maximum penetration depth $D_p$ of the secondary flow 262).

Figure 3A:
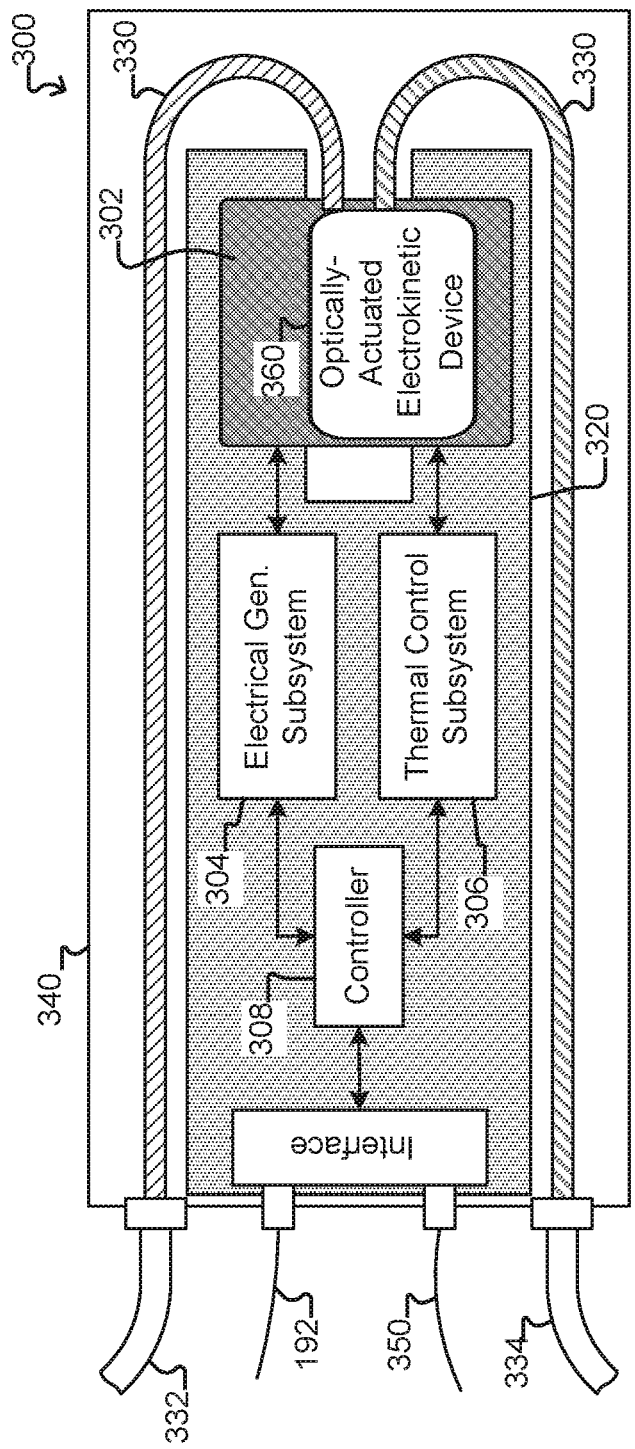
FIG. 3A illustrates a specific example of a system for use with a microfluidic device and associated control equipment according to some embodiments of the invention.
Figure 3B:
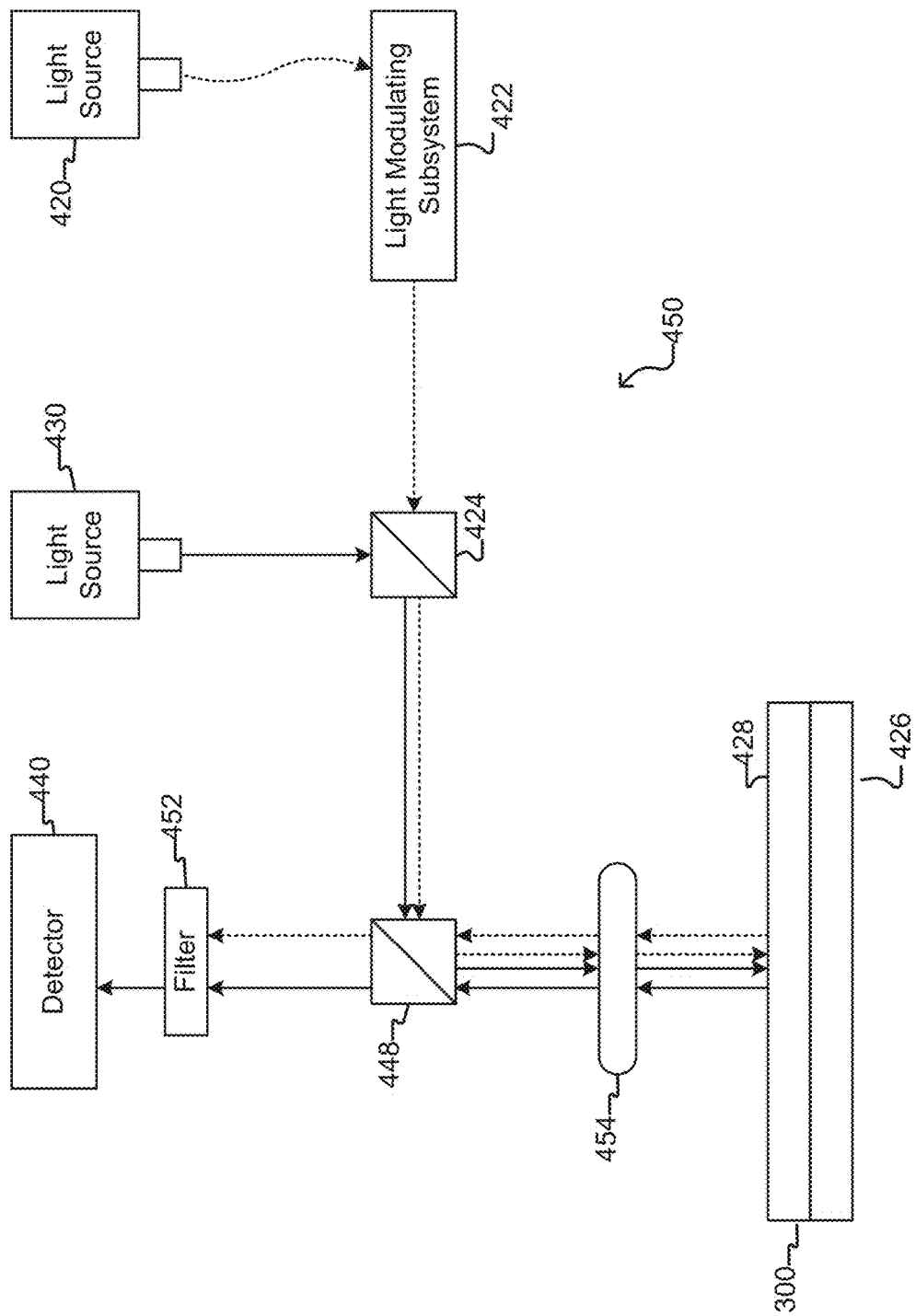
FIG. 3B illustrates an imaging device according to some embodiments of the invention.

FIGS. 3A and 3B shows various embodiments of system 150 which can be used to operate and observe microfluidic devices (e.g. 100, 200, 240, 290) according to the present invention. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 360 (e.g., an optically-actuated electrokinetic device 100) and providing electrical connections from power source 192 to microfluidic device 360. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 360 when it is being held by socket 302. Thus, the electrical signal generation subsystem 304 can be part of power source 192. The ability to apply a biasing voltage to microfluidic device 360 does not mean that a biasing voltage will be applied at all times when the microfluidic device 360 is held by the socket 302. Rather, in most cases, the biasing voltage will be applied intermittently, e.g., only as needed to facilitate the generation of electrokinetic forces, such as dielectrophoresis or electrowetting, in the microfluidic device 360.

As illustrated in FIG. 3A, the nest 300 can include a printed circuit board assembly (PCBA) 320. The electrical signal generation subsystem 304 can be mounted on and electrically integrated into the PCBA 320. The exemplary nest 300 includes socket 302 mounted on PCBA 320, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 360 held by the socket 302. In certain embodiments, the oscilloscope measures the waveform at a location proximal to the microfluidic device 360 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 360 and then adjust its own output voltage as needed such that the measured voltage at the microfluidic device 360 is the desired value. In some embodiments, the waveform amplification circuit can have a +6.5V to −6.5V power supply generated by a pair of DC-DC converters mounted on the PCBA 320, resulting in a signal of up to 13 Vpp at the microfluidic device 100.

As illustrated in FIG. 3A, the nest 300 can further include a thermal control subsystem 306. The thermal control subsystem 306 can be configured to regulate the temperature of microfluidic device 360 held by the nest 300. For example, the thermal control subsystem 306 can include a Peltier thermoelectric device (not shown) and a cooling unit (not shown). The Peltier thermoelectric device can have a first surface configured to interface with at least one surface of the microfluidic device 360. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 330 configured to circulate cooled fluid through the cooling block. In the embodiment illustrated in FIG. 3A, the nest 300 comprises an inlet 332 and an outlet 334 to receive cooled fluid from an external reservoir (not shown), introduce the cooled fluid into the fluidic path 330 and through the cooling block, and then return the cooled fluid to the external reservoir. In some embodiments, the Peltier thermoelectric device, the cooling unit, and/or the fluidic path 330 can be mounted on a casing 340 of the nest 300. In some embodiments, the thermal control subsystem 306 is configured to regulate the temperature of the Peltier thermoelectric device so as to achieve a target temperature for the microfluidic device 360. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient +/−0.02 ppm/CO) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 350 which allows the microprocessor of the controller 308 to communicate with an external master controller 154 via the interface 310. In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 350, the electrical signal generation subsystem 304 and the thermal control subsystem 306 can communicate with the external master controller 154. In this manner, the master controller 154 can, among other things, assist the electrical signal generation subsystem 304 by performing scaling calculations for output voltage adjustments. A Graphical User Interface (GUI) (not shown), provided via a display device 170 coupled to the external master controller 154, can be configured to plot temperature and waveform data obtained from the thermal control subsystem 306 and the electrical signal generation subsystem 304, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 422. The light modulating subsystem 422 can include a digital mirror device (DMD) or a microshutter array system (MSA), either of which can be configured to receive light from a light source 420 and transmits a subset of the received light into an optical train of microscope 450. Alternatively, the light modulating subsystem 422 can include a device that produces its own light (and thus dispenses with the need for a light source 420), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 422 can be, for example, a projector. Thus, the light modulating subsystem 422 can be capable of emitting both structured and unstructured light. One example of a suitable light modulating subsystem 422 is the Mosaic™ system from Andor Technologies™. In certain embodiments, imaging module 164 and/or motive module 162 of system 150 can control the light modulating subsystem 422.

In certain embodiments, the imaging device 194 further comprises a microscope 450. In such embodiments, the nest 300 and light modulating subsystem 422 can be individually configured to be mounted on the microscope 450. The microscope 450 can be, for example, a standard research-grade light microscope or fluorescence microscope. Thus, the nest 300 can be configured to be mounted on the stage 426 of the microscope 450 and/or the light modulating subsystem 422 can be configured to mount on a port of microscope 450. In other embodiments, the nest 300 and the light modulating subsystem 422 described herein can be integral components of microscope 450.

In certain embodiments, the microscope 450 can further include one or more detectors 440. In some embodiments, the detector 440 is controlled by the imaging module 164. The detector 440 can include an eye piece, a charge-coupled device (CCD), a camera (e.g., a digital camera), or any combination thereof. If at least two detectors 440 are present, one detector can be, for example, a fast-frame-rate camera while the other detector can be a high sensitivity camera. Furthermore, the microscope 450 can include an optical train configured to receive reflected and/or emitted light from the microfluidic device 360 and focus at least a portion of the reflected and/or emitted light on the one or more detectors 440. The optical train of the microscope can also include different tube lenses (not shown) for the different detectors, such that the final magnification on each detector can be different.

In certain embodiments, imaging device 194 is configured to use at least two light sources. For example, a first light source 420 can be used to produce structured light (e.g., via the light modulating subsystem 422) and a second light source 430 can be used to provide unstructured light. The first light source 420 can produce structured light for optically-actuated electrokinesis and/or fluorescent excitation, and the second light source 430 can be used to provide bright field illumination. In these embodiments, the motive module 164 can be used to control the first light source 420 and the imaging module 164 can be used to control the second light source 430. The optical train of the microscope 450 can be configured to (1) receive structured light from the light modulating subsystem 422 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 440. The optical train can be further configured to receive unstructured light from a second light source and focus the unstructured light on at least a second region of the microfluidic device, when the device is held by the nest 300. In certain embodiments, the first and second regions of the microfluidic device can be overlapping regions. For example, the first region can be a subset of the second region.

In FIG. 3B, the first light source 420 is shown supplying light to a light modulating subsystem 422, which provides structured light to the optical train of the microscope 450 of system 450. The second light source 430 is shown providing unstructured light to the optical train via a beam splitter 424. Structured light from the light modulating subsystem 422 and unstructured light from the second light source 430 travel from the beam splitter 424 through the optical train together to reach a second beam splitter 424 (or dichroic filter 448, depending on the light provided by the light modulating subsystem 422), where the light gets reflected down through the objective 454 to the sample plane 428. Reflected and/or emitted light from the sample plane 428 then travels back up through the objective 454, through the beam splitter and/or dichroic filter 448, and to a dichroic filter 452. Only a fraction of the light reaching dichroic filter 452 passes through and reaches the detector 440.

In some embodiments, the second light source 430 emits blue light. With an appropriate dichroic filter 452, blue light reflected from the sample plane 428 is able to pass through dichroic filter 452 and reach the detector 440. In contrast, structured light coming from the light modulating subsystem 422 gets reflected from the sample plane 428, but does not pass through the dichroic filter 452. In this example, the dichroic filter 452 is filtering out visible light having a wavelength longer than 495 nm. Such filtering out of the light from the light modulating subsystem 422 would only be complete (as shown) if the light emitted from the light modulating subsystem did not include any wavelengths shorter than 495 nm. In practice, if the light coming from the light modulating subsystem 422 includes wavelengths shorter than 495 nm (e.g., blue wavelengths), then some of the light from the light modulating subsystem would pass through filter 452 to reach the detector 440. In such an embodiment, the filter 452 acts to change the balance between the amount of light that reaches the detector 440 from the first light source 420 and the second light source 430. This can be beneficial if the first light source 420 is significantly stronger than the second light source 430. In other embodiments, the second light source 430 can emit red light, and the dichroic filter 452 can filter out visible light other than red light (e.g., visible light having a wavelength shorter than 650 nm).

Additional System Components for Maintenance of Viability of Cells within the Growth Chambers of the Microfluidic Device.

In order to promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells.

Conditioned Surface of the Microfluidic Device.

In some embodiments, at least one surface of the microfluidic device is conditioned to support cell growth, viability, portability, or any combination thereof. In some embodiments, substantially all the inner surfaces are conditioned. A conditioned surface may be one of the elements facilitating successful cell incubation within the microfluidic device. Identification of an appropriate conditioned surface may require balancing a number of operational requirements. First, the conditioned surface may provide a contacting surface that acts to shield cells from the types of materials which may be used in the fabrication of microfluidic devices of this class. Without being limited by theory, the conditioned surface may be surrounded by waters of hydration, which provide an aqueous, not a metallic contact layer with the cells. Second, the conditioned surface may provide a contacting surface with which the at least one biological cell may be supported adequately during incubation, without substantially inhibiting the ability of the cell to be removed from the growth chamber after completion of incubation. For example, many cells require a contacting surface to have some degree of hydrophilicity in order to adhere sufficiently to be viable and/or grow. Alternatively, some cells may require a contacting surface having a degree of hydrophobicity in order to grow and present desired levels of viability. Additionally, some cells may require the presence of selected proteins or peptide motifs within the contacting surface in order to initiate viability/growth responses. Third, the conditioning of the at least one surface may permit the motive forces used in the microfluidic device to function substantially within normal functioning power range. For example, if light actuated motive forces are employed, the conditioned surface may substantially permit passage of light through the conditioned surface such that the light actuated motive force is not substantially inhibited.

The at least one conditioned surface may include a surface of the growth chamber or a surface of the flow region, or a combination thereof. In some embodiments, each of a plurality of growth chambers has at least one conditioned surface. In other embodiments each of a plurality of flow regions has at least one conditioned surface. In some embodiments, at least one surface of each of a plurality of growth chambers and each of a plurality of flow regions are conditioned surfaces.

Conditioned Surface Including a Polymer.

The at least one conditioned surface may include a polymer. The polymer may be covalently or non-covalently linked to the at least one surface. Polymers may have a variety of structural motifs, including block polymers (and copolymers); star polymers (star copolymers); and graft or comb polymers (graft copolymers), all of which may be suitable for use herein.

The polymer may include a polymer including alkylene ether moieties. A wide variety of alkylene ether containing polymers may be suitable for use in the microfluidic device described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a conditioned surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the polymer conditioned surface may include a polymer containing carboxylic acid moieties. The carboxylic acid subunit may be an alkyl, alkenyl or aromatic moiety containing subunit. One non-limiting example is polylactic acid (PLA).

In some other embodiments, the polymer conditioned surface may include a polymer containing urethane moieties, such as, but not limited to polyurethane.

In other embodiments, the polymer conditioned surface may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. These latter exemplary polymers are polyelectrolytes and may alter the characteristics of the surface to aid/deter adhesion.

In yet other embodiments, the polymer conditioned surface may include a polymer containing phosphate moieties, either at a terminus of the polymer backbone or pendant from the backbone of the polymer.

In yet other embodiments, the polymer conditioned surface may include a polymer containing saccharide moieties. In a non-limiting example, polysaccharides such as those derived from algal polysaccharides such as xanthan gum or dextran may be suitable to form a polymer conditioned surface which may aid or prevent cell adhesion. For example, a dextran polymer having a size about 3 Kda may be used to provide a conditioned surface within a microfluidic device.

In yet other embodiments, the polymer conditioned surface may include a polymer containing nucleotide moieties, i.e. a nucleic acid, which may have ribonucleotide moieties or deoxyribonucleotide moieties. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation. A nucleic acid containing polymer may include a polyelectrolyte which may aid or prevent adhesion.

In yet other embodiments, the polymer conditioned surface may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA). In some embodiments, an extracellular matrix (ECM) protein may be provided within the conditioned surface for optimized cell adhesion to foster cell growth. A cell matrix protein which may be included in a conditioned surface can include, but is not limited to, a collagen, an elastin, an RGD-containing peptide (e.g. a fibronectin), or a laminin. In yet other embodiments, growth factors, cytokines, hormones or other cell signaling species may be provided within the at least one conditioned surface of the microfluidic device.

In further embodiments, the polymer conditioned surface may include a polymer including amine moieties. The polyamino polymer may include a natural polyamine polymer or a synthetic polyamine polymer. Examples of natural polyamines include spermine, spermidine, and putrescine.

In some embodiments, the polymer conditioned surface may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the conditioned surface.

Covalently Linked Conditioned Surface.

In some embodiments, the at least one conditioned surface includes a covalently linked moiety configured to support cell growth, viability, portability, or any combination thereof of the one or more biological cells within the microfluidic device. The covalently linked moiety can include a linking group, wherein the linking group is covalently linked to a surface of the microfluidic device. The linking group is also linked to the moiety configured to support cell growth, viability, portability, or any combination thereof of the one or more biological cells within the microfluidic device. The surface to which the linking group links may include a surface of the substrate of the microfluidic device, which for embodiments in which the microfluidic device includes a DEP configuration, can include silicon and/or silicon dioxide. In some embodiments, the covalently linked conditioned surface includes all of the inner surfaces of the microfluidic device.

Figure 9:
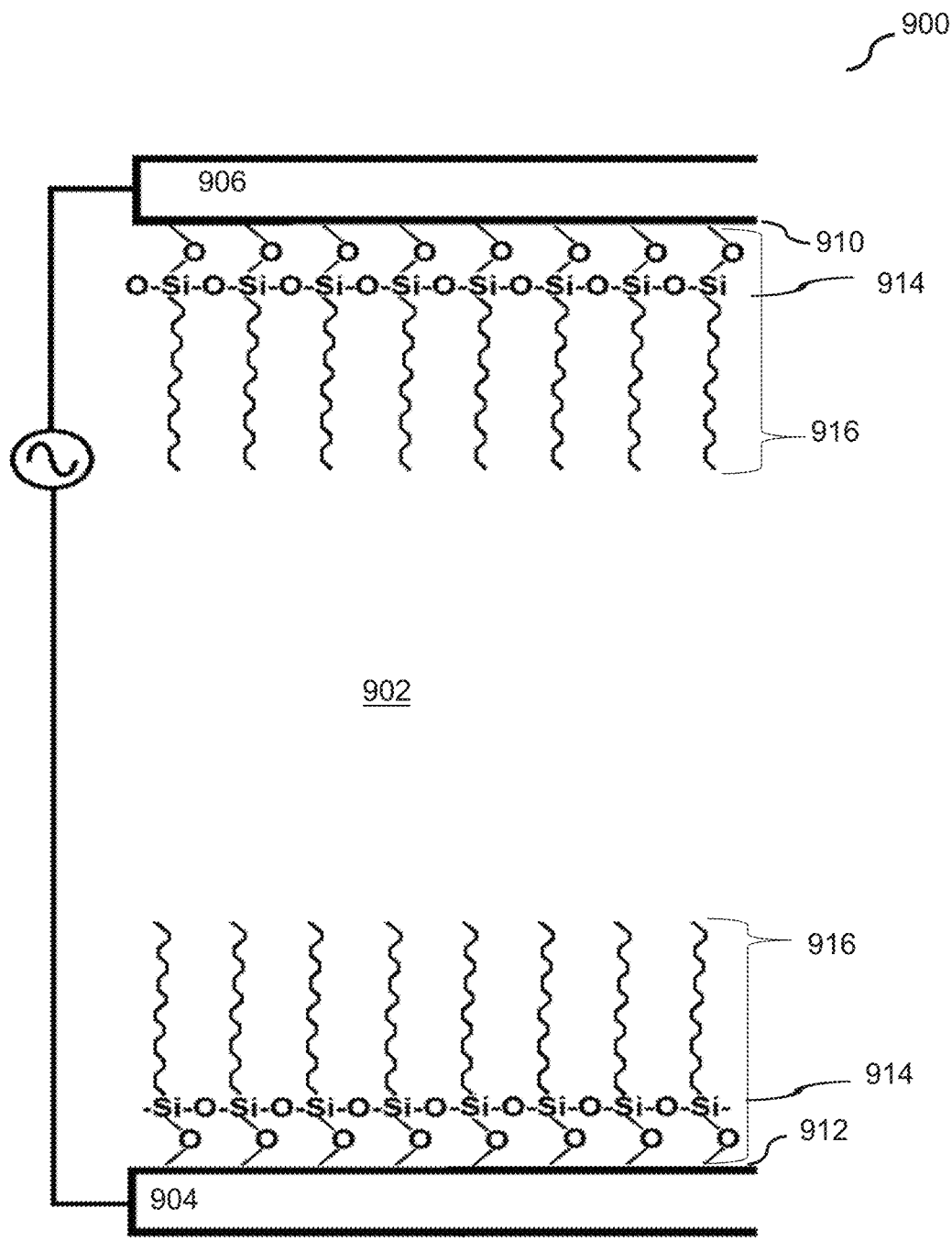
FIG. 9 is a schematic representation of a conditioned surface providing enhanced support cell growth, viability, portability, or any combination thereof.

A schematic representation is shown in FIG. 9 for a microfluidic device having a conditioned surface. As seen in FIG. 9, a microfluidic device 900 has a first DEP substrate 904 and a second DEP substrate 906 facing an enclosed region 902 of the microfluidic device which may include the at least one growth chamber and/or the flow region. The device 900 may be otherwise configured like any of microfluidic devices 100, 200, 240, 290, 400, 500A-E, or 600. The enclosed region 902 may be the region in which biological cells are either maintained or are imported into or exported out from. The inner surfaces 910 (of the second DEP substrate 906) and 912 (of the first DEP substrate 904) are modified with a conditioned surface 916, which may be any moiety supporting cell growth, viability, portability, or any combination thereof. The conditioned surface is covalently linked to oxide functionalities of the inner surfaces via a siloxy linking group 914 in this embodiment.

In some embodiments, the covalently linked moiety configured to support cell growth, viability, portability, or any combination thereof, may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

The covalently linked moiety configured to support cell growth, viability, portability, or any combination thereof of one or more biological cells within the microfluidic device may be any polymer as described herein, and may include one or more polymers containing alkylene oxide moieties, carboxylic acid moieties, saccharide moieties, sulfonic acid moieties, phosphate moieties, amino acid moieties, nucleic acid moieties, or amino moieties.

In other embodiments, the covalently linked moiety configured to support cell growth, viability, portability, or any combination thereof of one or more biological cells may include non-polymeric moieties such as an alkyl moiety, fluoroalkyl moiety (including but not limited to perfluoroalkyl), amino acid moiety, alcohol moiety, amino moiety, carboxylic acid moiety, phosphonic acid moiety, sulfonic acid moiety, sulfamic acid moiety, or saccharide moiety.

In some embodiments, the covalently linked moiety may be an alkyl group. The alkyl group can comprise carbon atoms that form a linear chain (e.g., a linear chain of at least 10 carbons, or at least 14, 16, 18, 20, 22, or more carbons). Thus, the alkyl group may be an unbranched alkyl. In some embodiments, the alkyl group may include a substituted alkyl group (e.g., some of the carbons in the alkyl group can be fluorinated or perfluorinated). The alkyl group may comprise a linear chain of substituted (e.g., fluorinated or perfluorinated) carbons joined to a linear chain of non-substituted carbons. For example, the alkyl group may include a first segment, which may include a perfluoroalkyl group, joined to a second segment, which may include a non-substituted alkyl group. The first and second segments may be joined directly or indirectly (e.g., by means of an ether linkage). The first segment of the alkyl group may be located distal to the linking group, and the second segment of the alkyl group may be located proximal to the linking group. In other embodiment, the alkyl group may include a branched alkyl group and may further have one or more arylene group interrupting the alkyl backbone of the alkyl group. In some embodiments, a branched or arylene-interrupted portion of the alkyl or fluorinated alkyl group is located at a point distal to the covalent linkage to the surface.

In other embodiments, the covalently linked moiety may include at least one amino acid, which may include more than one amino acids. The covalently linked moiety may include a peptide or a protein. In some embodiments, the covalently linked moiety may include an amino acid which may provide a zwitterionic surface to support cell growth, viability, portability, or any combination thereof.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the growth chamber.

The covalently linked moiety may include one or more carboxylic acid, phosphonic acid, sulfamic or sulfonic acid moieties. In some embodiments, the covalently linked moiety may include one or more nucleic acid moieties, which may have a sequence of individual nucleotides that is designed to capture nucleic acids from biological cells within the microfluidic device. The capture nucleic acids may have a nucleotide sequence that is complementary to the nucleic acid from the biological cells and may capture the nucleic acid by hybridization.

The conditioned surface may be composed of only one kind of moiety or may include more than one different kind of moiety. For example, the fluoroalkyl conditioned surfaces (including perfluoroalkyl) may have a plurality of covalently linked moieties which are all the same, e.g. has the same covalent attachment to the surface and has the same number of fluoromethylene units comprising the fluoroalkyl moiety supporting growth and/or viability and/or portability. Alternatively, the conditioned surface may have more than one kind of moiety attached to the surface. For example, the conditioned surface may include alkyl or fluoroalkyl groups having a specified number of methylene or fluoromethylene units and may further include a further set of groups attached to the surface having a charged moiety attached to an alkyl or fluoroalkyl chain that has a greater number of methylene or fluoromethylene units. In some embodiments, the conditioned surface having more than one kind of moiety attached may be designed such that a first set of attached ligands which have a greater number of backbone atoms and thus having a greater length from the covalent attachment to the surface, may provide capacity to present bulkier moieties at the conditioned surface, while a second set of attached ligands having different, less sterically demanding termini while having fewer backbone atoms can help to functionalize the entire substrate surface to prevent undesired adhesion or contact with a silicon or alumina substrate itself. In another example, the moieties attached to the surface may provide a zwitterionic surface presenting alternating charges in a random fashion on the surface.

Conditioned Surface Properties.

In some embodiments, the covalently linked moieties may form a monolayer when covalently linked to the surface of the microfluidic device (e.g., a DEP configured substrate surface). In some embodiments, the conditioned surface formed by the covalently linked moieties may have a thickness of less than 10 nm (e.g., less than 5 nm, or about 1.5 to 3.0 nm). In other embodiments, the conditioned surface formed by the covalently linked moieties may have a thickness of about 10 nm to about 50 nm. In some embodiments, the conditioned surface does not require a perfectly formed monolayer to be suitably functional for operation within a DEP configuration.

In various embodiments, the conditioned surface(s) of the microfluidic device may provide desirable electrical properties. Without intending to be limited by theory, one factor that impacts robustness of a conditioned surface is intrinsic charge trapping. Different surface conditioning materials may trap electrons which can lead to breakdown of the material. Defects in the conditioned surface may lead to charge trapping and further breakdown of the conditioned surface.

Aside from the composition of the conditioned surface, other factors such as physical thickness of the hydrophobic material can impact DEP force. Various factors can alter the physical thickness of the conditioned surface, such as the manner in which the conditioned surface is formed on the substrate (e.g. vapor deposition, liquid phase deposition, spin coating, flooding, and electrostatic coating). The physical thickness and uniformity of the conditioned surface can be measured using an ellipsometer.

In addition to its electrical properties, the conditioned surface may also have properties that are beneficial in use with biological molecules. For example, a conditioned surface that contains fluorinated (or perfluorinated) carbon chains may provide a benefit relative to alkyl-terminated chains in reducing the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Various properties for conditioned surfaces which may be used in DEP configurations are included in the table below. As can be seen, for entries 1 to 7, which were all covalently linked conditioned surfaces as described herein, the thickness as measured by ellipsometry were consistently thinner than that of entry 8, a CYTOP surface which was formed by non-covalent spin coating (N/A represents data not available throughout the table). Fouling was found to be more dependent upon the chemical nature of the surface than upon the mode of formation as the fluorinated surfaces were typically less fouling than that of alkyl (hydrocarbon) conditioned surfaces

TABLE 1

Properties of various conditioned surfaces prepared by covalently modifying a surface, compared to CYTOP, a non-covalently formed surface.

| Surface modification type | Formula of surface modifying reagent | Thickness | Fouling |
|---|---|---|---|
| Alkyl terminated siloxane ($C_{16}$) | $CH_3-(CH_2)_{15}-Si-(OCH_3)_3$ | N/A | More fouling than fluorinated layers. |
| Alkyl terminated siloxane ($C_{18}$) | $CH_3-(CH_2)_{17}-Si-(OCH_3)_3$ | ~2 nm | More fouling than fluorinated layers. |
| Alkyl-terminated phosphonate ester $C_{18}P$ | $CH_3-(CH_2)_{17}-P=O(OH)_2$ | N/A | More fouling than fluorinated layers. |
| Alkyl terminated siloxane ($C_{22}$) | $CH_3-(CH_2)_{21}-Si-(OCH_2CH_3)_3$ | ~2-2.5 nm | More fouling than fluorinated layers. |
| Fluoro-alkyl-terminated alkyl-siloxane $C_{10}F$ | $CF_3-(CF_2)_7-(CH_2)_2-Si-(OCH_3)_3$ | ~1 nm | More resistant to fouling than alkyl-terminated layers |
| Fluoro-alkyl-terminated alkyl-siloxane ($C_{16}F$) | $CF_3-(CF_2)_{13}-(CH_2)_2-Si-(OCH_3)_3$ | ~2 nm | More resistant to fouling than alkyl-terminated layers |
| Fluoro-alkyl-terminated alkoxy-alkyl-siloxane $C_6FC_{13}$ | $CF_3-(CF_2)_5-(CH_2)_2-O-(CH_2)_{11}-Si(OCH_3)_3$ | ~2 nm | N/A |
| CYTOP Fluoropolymer [1,2] | | ~30 nm | More resistant to fouling than alkyl-terminated layers |

1. CYTOP structure:

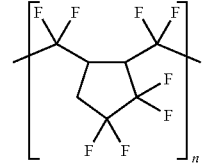

2. Spin coated, not covalent.

Linking Group to Surface.

The covalently linked moieties forming the conditioned surface are attached to the surface via a linking group. The linking group may be a siloxy linking group formed by the reaction of a siloxane containing reagent with oxides of the substrate surface, which may be formed from silicon or aluminum oxide. In some other embodiments, the linking group may be a phosphonate ester formed by the reaction of a phosphonic acid containing reagent with the oxides of the silicon or aluminum substrate surface.

Multi-Part Conditioned Surface.

The covalently linked conditioned surface may be formed by reaction of a surface conditioning reagent which is configured to already contain the moiety providing the conditioned surface (e.g., an alkyl siloxane reagent or a fluoro substituted alkyl siloxane reagent, which may include a perfluoroalkyl siloxane reagent), as is described below. Alternatively, the conditioned surface may be formed by coupling the moiety which supports cell growth, viability, portability, or any combination thereof to a surface modifying ligand that itself is covalently linked to the surface.

Structures for a Conditioned Surface and Methods of Preparation.

In some embodiments, a conditioned surface covalently linked to oxides of the surface of the dielectrophoresis substrate has a structure of Formula 1:

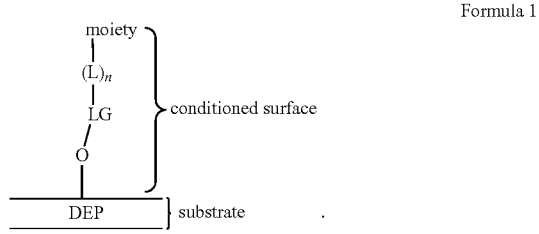

Formula 1

The conditioned surface may be linked covalently to oxides of the surface of the dielectrophoresis substrate. The dielectrophoresis substrate may be silicon or alumina, and oxides may be present as part of the native chemical structure of the substrate or may be introduced as discussed below. The conditioned surface may be attached to the oxides via a linking group LG which may be a siloxy or phosphonate ester group, formed from the reaction of a siloxane or phosphonic acid group with the oxides.

The moiety configured to support cell growth, viability, portability, or any combination thereof, may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocyclic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids. An alkyl or fluoroalkyl moiety may have a backbone chain length of equal to or greater than 10 carbons. In some embodiments, the alkyl or fluoroalkyl moiety may have a backbone chain length of about 10, 12, 14, 16, 18, 20, or 22 carbons.

The linking group LG may be directly or indirectly connected to the moiety providing support cell growth, viability, portability, or any combination thereof within the microfluidic device. When the linking group LG is directly connected to the moiety, optional linker L is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and phosphorus atoms, subject to chemical bonding limitations as is known in the art. It may be interrupted with any combination of one or more moieties selected from the group consisting of ether, amino, carbonyl, amido, or phosphonate groups, in some non-limiting examples. Additionally, the linker L may have one or more arylene, heteroarylene, or heterocyclic groups interrupting the backbone of the linker. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

Surface Conditioning Reagent.

When the moiety configured to support cell growth, viability, portability, or any combination thereof, and thereby providing the conditioned surface, is added to the surface of the substrate in a one step process, a surface conditioning reagent of Formula 6 may be used to introduce the conditioned surface.

The surface conditioning reagent may have a structure of Formula 6:

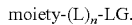

Formula 6

In the surface conditioning reagent of Formula 6, the surface conditioning reagent may include a linking group LG, which may be siloxane or a phosphonic acid group. The linking group LG may be directly or indirectly linked to the moiety configured to support cell growth, viability, portability, or any combination thereof. LG may be directly (n=0) or indirectly (n=1) linked to the moiety configured to support cell growth, viability, portability, or any combination thereof via connection to a first end of a linker L. The linker L may further include a linear portion wherein a backbone of the linear portion may have 1 to 200 non-hydrogen atoms selected from any combination of silicon, carbon, nitrogen, oxygen, sulfur and phosphorus atoms, subject to chemical bonding limitations as is known in the art. The backbone of the linear portion may further include one or more arylene moieties. The moiety configured to support cell growth, viability, portability, or any combination thereof ("moiety"), may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocyclic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acid; or amino acids. The moiety configured to support cell growth, viability, portability, or any combination thereof may include alkyl or perfluoroalkyl moieties. The alkyl or perfluoroalkyl moieties may have a backbone chain length of greater than 10 carbons. The moiety configured to support cell growth, viability, portability, or any combination thereof of the surface conditioning reagent may include saccharide moieties, and may be dextran. In other embodiments, the moiety configured to support cell growth, viability, portability, or any combination thereof of the surface conditioning reagent may include alkylene ether moieties. The alkylene ether moieties may be polyethylene glycol. The surface conditioning reagent may further include a cleavable moiety, which may be located within the linker L or may be part of the moiety configured to support cell growth, viability, portability, or any combination thereof of the surface conditioning reagent. The cleavable moiety may be configured to permit disruption of the conditioned surface thereby promoting portability of the one or more biological cells.

In some embodiments, the moiety supporting cell growth, viability, portability, or any combination thereof may be added to the surface of the substrate in a multi-step process. When the moiety is coupled to the surface in a step wise fashion, the linker L may further include a coupling group CG, as shown in Formula 2.

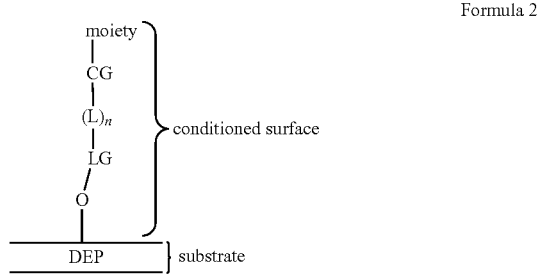

Formula 2

In some embodiments, the coupling group CG represents the resultant moiety from reaction of a reactive moiety $R_x$ and a moiety that it is configured to react with, a reactive pairing moiety $R_{px}$. For example, one typical CG may include a carboxamidyl group, which is the result of the reaction of an amino group with a derivative of a carboxylic acid, such as an activated ester, an acid chloride or the like. CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end of the linker L, where the moiety is attached. In some other embodiments, the coupling group CG may interrupt the backbone of the linker L. In some embodiments, the coupling group CG is triazolylene, which is the result of a reaction between an alkyne group and an azide group, either of which may be the reactive moiety or the reactive pairing moiety, as is known in the art for use in Click coupling reactions. A triazolylene group may also be further substituted. For example, a dibenzocylcooctenyl fused triazolylene moiety may result from the reaction of a conditioning modification reagent having a dibenzocyclooctynyl reactive pairing moiety $R_{px}$ with an azido reactive moiety $R_x$ of the surface modifying ligand, which are described in more detail in the following paragraphs. A variety of dibenzocyclooctynyl modified molecules are known in the art or may be synthesized to incorporate a moiety configured to support cell growth, viability, portability, or any combination thereof.

When the conditioned surface is formed in a multi-step process, the moiety supporting cell growth, viability, portability, or any combination thereof may be introduced by reaction of a conditioning modification reagent (Formula 5) with a substrate having a surface modifying ligand covalently linked thereto, having a structure of Formula 3.

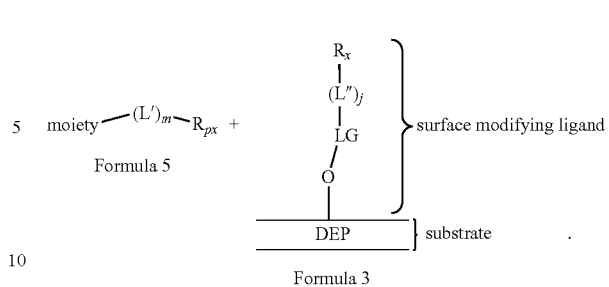

Formula 3

The intermediate modified surface of Formula 3 has a surface modifying ligand attached thereto, which has a formula of -LG-(L")j-$R_x$, which is linked to the oxide of the substrate, and is formed similarly as described above for the conditioned surface of Formula 1. The surface of the DEP substrate is as described above, and includes oxides either native to the substrate or introduced therein. The linking group LG is as described above. A linker L" may be present (j=1) or absent (j=0). The linker L" may have a linear portion where a backbone of the linear portion may include 1 to 100 non-hydrogen atoms selected from any combination of silicon, carbon, nitrogen, oxygen, sulfur and phosphorus atoms, subject to chemical bonding limitations as is known in the art. It may be interrupted with any combination of ether, amino, carbonyl, amido, or phosphonate groups, in some non-limiting examples. Additionally, the linker L" may have one or more arylene, heteroarylene, or heterocyclic groups interrupting the backbone of the linker. In some embodiments, the backbone of the linker L" may include 10 to 20 carbon atoms. In other embodiments, the backbone of the linker L" may include about 5 atoms to about 100 atoms; about 10 atoms to about 80 atoms, about 10 atoms to about 50 atoms, or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

A reactive moiety $R_x$ is present at the terminus of the surface modifying ligand distal to the covalent linkage of the surface modifying ligand with the surface. The reactive moiety $R_x$ is any suitable reactive moiety useful for coupling reactions to introduce the moiety that supports cell growth, viability, portability, or any combination thereof. In some embodiments, the reactive moiety $R_x$ may be an azido, amino, bromo, a thiol, an activated ester, a succinimidyl or alkynyl moiety.

Conditioning Modification Reagent.

The conditioning modification reagent (Formula 5) is configured to supply the moiety supporting cell growth, viability, portability, or any combination thereof.

Formula 5

The moiety configured to support cell growth, viability, portability, or any combination thereof of the conditioning modification reagent is linked to the surface modifying ligand by reaction of a reactive pairing moiety $R_{px}$ with the reactive moiety $R_x$. The reactive pairing moiety $R_{px}$ is any suitable reactive group configured to react with the respective reactive moiety $R_x$. In one non-limiting example, one suitable reactive pairing moiety $R_{px}$ may be an alkyne and the reactive moiety $R_x$ may be an azide. The reactive pairing moiety $R_{px}$ may alternatively be an azide moiety and the respective reactive moiety $R_x$ may be alkyne. In other embodiments, the reactive pairing moiety $R_{px}$ may be an active ester functionality and the reactive moiety $R_x$ may be an amino group. In other embodiments, the reactive pairing moiety $R_{px}$ may be aldehyde and the reactive moiety $R_x$ may be amino Other reactive moiety-reactive pairing moiety combinations are possible, and these examples are in no way limiting.

The moiety configured to support cell growth, viability, portability, or any combination thereof of the conditioning modification reagent of Formula 5, may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocyclic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

The moiety providing enhanced cell growth, viability, portability, or any combination thereof of the conditioning modification reagent of Formula 5 may be directly (L', where m=0) or indirectly connected to the reactive pairing moiety $R_{px}$. When the reactive pairing moiety $R_{px}$ is connected indirectly to the moiety providing enhanced cell growth, viability, portability, or any combination thereof, the reactive pairing moiety $R_{px}$ may be connected to a linker L' (m=1). The reactive pairing moiety $R_{px}$ may be connected to a first end of the linker L', and the moiety providing enhanced cell growth, viability, portability, or any combination thereof may be connected to a second end of the linker L'. Linker L' may have a linear portion wherein a backbone of the linear portion includes 1 to 100 non-hydrogen atoms selected from any combination of silicon, carbon, nitrogen, oxygen, sulfur and phosphorus atoms, subject to chemical bonding limitations as is known in the art. It may be interrupted with any combination of ether, amino, carbonyl, amido, or phosphonate groups, in some non-limiting examples. Additionally, the linker L' may have one or more arylene, heteroarylene, or heterocyclic groups interrupting the backbone of the linker L'. In some embodiments, the backbone of the linker L' may include 10 to 20 atoms. In other embodiments, the backbone of the linker L' may include about 5 atoms to about 100 atoms; about 10 atoms to about 80 atoms; about 10 atoms to about 50 atoms; or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

When the conditioning modification reagent (Formula 5) reacts with the surface having a surface modifying ligand (Formula 3), a substrate having a conditioned surface of Formula 2 is formed. Linker L' and linker L" then are formally part of linker L, and the reaction of the reactive pairing moiety $R_{px}$ with the reactive moiety $R_x$ yields the coupling group CG of Formula 2.

Surface Modifying Reagent.

The surface modifying reagent is a compound having a structure LG-(L")$_j$-$R_x$ (Formula 4). The linking group LG links covalently to the oxides of the surface of the dielectrophoresis substrate. The dielectrophoresis substrate may be silicon or alumina, and oxides may be present as part of the native chemical structure of the substrate or may be introduced as discussed herein. The linking group LG may be a siloxy or phosphonate ester group, formed from the reaction of a siloxane or phosphonic acid group with the oxide on the surface of the substrate. The reactive moiety $R_x$ is described above. The reactive moiety $R_x$ may be connected directly (L", j=0) or indirectly via a linker L" (j=1) to the linking group LG. The linking group LG may be attached to a first end of the linker L" and the reactive moiety $R_x$ may be connected to a second end of the linker L", which will be distal to the surface of the substrate once the surface modifying ligand has been attached to the surface as in Formula 3.

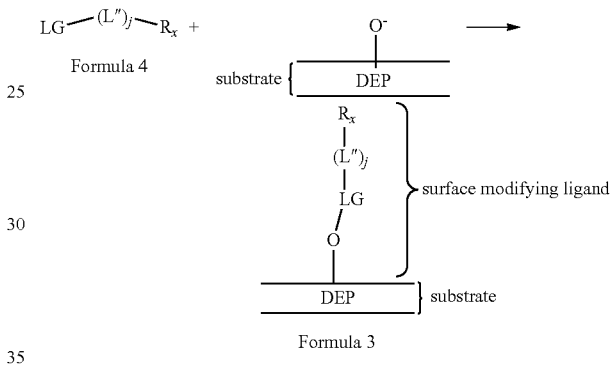

Linker L" may have a linear portion wherein a backbone of the linear portion includes 1 to 100 non-hydrogen atoms selected from any combination of silicon, carbon, nitrogen, oxygen, sulfur and phosphorus atoms. It may be interrupted with any combination of ether, amino, carbonyl, amido, or phosphonate groups, in some non-limiting examples. Additionally, the linker L" may have one or more arylene, heteroarylene, or heterocyclic groups interrupting the backbone of the linker L". In some embodiments, the backbone of the linker L" may include 10 to 20 atoms. In other embodiments, the backbone of the linker L" may include about 5 atoms to about 100 atoms; about 10 atoms to about 80 atoms, about 10 atoms to about 50 atoms, or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

Cleavable Moieties.

In various embodiments, any of: the moiety supporting cell growth, viability, portability, or any combination thereof, linker L, linker L', linker L" or coupling group CG may further include a cleavable moiety, as discussed below. The cleavable moiety may be configured to permit disruption of a conditioned surface of a microfluidic device which promotes portability of the one or more biological cells. In some embodiments, portability of the one or more biological cells is desirable in order to be able to move the cells after culturing the cells for a period of time, and in particular, to be able to export the cells out of the microfluidic device.

Compositions of Substrates.

Accordingly, a composition is provided, including a substrate having a dielectrophoresis (DEP) configuration and a surface; and a conditioned surface covalently linked to oxide moieties of the surface of the substrate. The conditioned surface on the substrate may have a structure of Formula 1 or Formula 2:

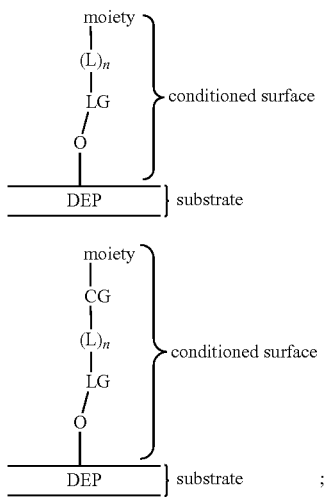

where LG is a linking group; L is a linker which may be present (n=1) or absent (n=0); moiety is the moiety supporting cell growth, viability, portability, or any combination thereof within the microfluidic device; and CG is a coupling group, as defined herein.

The conditioned surface may include a linking group LG covalently linked to the oxide moieties of the surface. The linking group may further be linked to a moiety configured to support cell growth, viability, portability, or any combination thereof. The linking group may be a siloxy linking group. In other embodiments, the linking group may be a phosphonate ester. The linking group may be directly or indirectly linked to the moiety configured to support cell growth, viability, portability, or any combination thereof. The linking group may be indirectly linked to the moiety configured to support cell growth, viability, portability, or any combination thereof via connection to a first end of a linker. The linker may further include a linear portion wherein a backbone of the linear portion may have 1 to 200 non-hydrogen atoms selected from any combination of silicon, carbon, nitrogen, oxygen, sulfur and phosphorus atoms, as discussed above. The backbone of the linear portion may further include one or more arylene moieties.

The linker may have a coupling group CG, defined as above. The coupling group CG may include a triazolylene moiety. The triazolylene moiety may interrupt the linear portion of the linker or may be connected at a second end to the linear portion of the linker. The second end of the linker may be distal to the surface of the substrate. The moiety configured to support cell growth, viability, portability, or any combination thereof may include one or more of alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol); alkylene ethers, including but not limited to polyethylene glycol; polyelectrolytes (including but not limited to poly acrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids. In some embodiments, a mixture of different moieties is incorporated in the conditioned surface, such as, but not limited to a mixture of anionic and cationic functionalities which provide a zwitterionic conditioned surface. The conditioned surface may include alkyl or perfluoroalkyl moieties. The alkyl or perfluoroalkyl moieties may have a backbone chain length of greater than 10 carbons. The conditioned surface may include saccharide moieties, and may be dextran. In other embodiments, the conditioned surface may include alkylene ether moieties. The alkylene ether moieties may be polyethylene glycol. The conditioned surface may further include a cleavable moiety. The cleavable moiety may be configured to permit disruption of the conditioned surface thereby promoting portability of the one or more biological cells.

Another composition is provided, including a substrate including a dielectrophoresis (DEP) configuration and a surface, and a surface modifying ligand covalently linked to oxide moieties of the surface of the substrate. The substrate having a surface modifying ligand may have a structure of Formula 3:

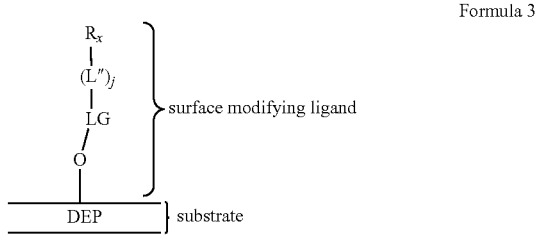

where LG is linking group; L" is an optional linker, j is 0 or 1. The linker L" is present when j=1 and absent when j=0; and $R_x$ is a reactive moiety as described herein.

The reactive moiety of the surface modifying ligand may be azido, amino, bromo, a thiol, an activated ester, a succinimidyl or alkynyl moiety. The surface modifying ligand may be covalently linked to the oxide moieties via a linking group. The linking group may be a siloxy moiety. In other embodiments, the linking group may be a phosphonate ester. The linking group may be connected indirectly via a linker to the reactive moiety of the surface modifying ligand. The linking group may be attached to a first end of the linker and the reactive moiety may be attached to a second end of the linker. The linker L" may include a linear portion wherein a backbone of the linear portion includes 1 to 100 non-hydrogen atoms selected from any combination of silicon, carbon, nitrogen, oxygen, sulfur and phosphorus atoms. The backbone of the linker L" may include 10 to 20 atoms. In other embodiments, the backbone of the linker L" may include about 5 atoms to about 50 atoms. In some embodiments, the backbone of the linker L" may include all carbon atoms. The backbone of the linear portion may include one or more arylene moieties. The linker L" may include a triazolylene moiety. The triazolylene moiety may interrupt or may be attached at a terminus of the linker L". The surface modifying ligand may include a cleavable moiety. The cleavable moiety may be configured to permit disruption of a conditioned surface of a microfluidic device thereby promoting portability of the one or more biological cells.

Method of Preparation.

In some embodiments, the conditioned surface or the surface modifying ligand is deposited on the inner surfaces of the microfluidic device using chemical vapor deposition. Through vapor deposition of molecules, the conditioned surface/surface modifying ligand can achieve densely packed monolayers in which the molecules comprising the conditioned surface/surface modifying ligand are covalently linked to the molecules of the inner surfaces of any of the microfluidic devices (100, 200, 240, 290, 400, 500A-E, 600). To achieve a desirable packing density, molecules comprising, for example, alkyl-terminated siloxane can be vapor deposited at a temperature of at least 110° C. (e.g., at least 120° C., 130° C., 140° C., 150° C., 160° C., etc.), for a period of at least 15 hours (e.g., at least 20, 25, 30, 35, 40, 45, or more hours). Such vapor deposition is typically performed under vacuum and in the presence of a water source, such as a hydrated sulfate salt (e.g., $MgSO_4 \cdot 7H_2O$). Typically, increasing the temperature and duration of the vapor deposition produces improved characteristics of the conditioned surface/surface modifying ligand. In some embodiments, the conditioned surface or the surface modifying ligand may be introduced by reaction in a liquid phase.

To prepare the microfluidic surfaces, the cover, microfluidic circuit material, and the electrode activation substrate may be treated by an oxygen plasma treatment, which can remove various impurities, while at the same time introducing an oxidized surface (e.g., oxides at the surface, which may be covalently modified as described herein). The oxygen plasma cleaner can be operated, for example, under vacuum conditions, at 100 W for 60 seconds. Alternatively, liquid-phase treatments, which include oxidizing agents such as hydrogen peroxide to oxidize the surface may be used. For example, a mixture of hydrochloric acid and hydrogen peroxide or a mixture of sulfuric acid and hydrogen peroxide (e.g, piranha solution, which may have a ratio of sulfuric acid to hydrogen peroxide in a range from about 3:1 to about 7:1).

The vapor deposition process can be optionally improved, for example, by pre-cleaning the cover, microfluidic circuit material, and the electrode activation substrate. For example, such pre-cleaning can include a solvent bath, such as an acetone bath, an ethanol bath, or a combination thereof. The solvent bath can include sonication.

In some embodiments, vapor deposition is used to coat the inner surface(s) of the microfluidic device after the microfluidic device has been assembled to form an enclosure defining a microfluidic circuit.

When a substrate having a surface modifying ligand is further reacted with conditioning modification reagent to prepare the substrate having a conditioned surface, the reaction may be performed in situ using any suitable solvent that will solubilize the reagent and will not disrupt either microfluidic circuit material or the surface having a surface modifying ligand. In some embodiments, the solvent is an aqueous solution.

Methods of Preparing a Conditioned Surface or a Surface Including a Surface Modifying Ligand.

Accordingly, a method of preparing a modified surface of a microfluidic device having a dielectrophoresis (DEP) configuration is provided, including the steps of providing a surface of a substrate of a microfluidic device, where the substrate includes a DEP configuration; reacting oxides of the surface with a modifying reagent, thereby converting the surface of the substrate into a modified surface. In some embodiments, the surface of the substrate may be plasma cleaned to provide the oxides on the surface. In some embodiments, the surface may be plasma cleaned before assembling the microfluidic device. In other embodiments, the surface may be plasma cleaned after assembling the microfluidic device.

The method, wherein the step of reacting the oxides of the surface with the modifying reagent is performed by exposing the surface to a liquid comprising the modifying reagent. In some embodiments, the step of reacting the oxides of the surface may be performed by exposing the surface to a vapor containing the modifying reagent at reduced pressure.

In some embodiments, the modifying reagent may include a surface conditioning reagent having a first moiety configured to react covalently with the surface and a second moiety configured to support cell growth, viability, portability, or any combination thereof, thereby modifying the surface to a surface conditioned to support cell growth, viability, portability, or any combination thereof.

The surface conditioning reagent may have a structure of Formula 6:

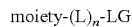

Formula 6

The first moiety may include a linking group LG, which may be siloxane or a phosphonic acid group. The linking group LG may be directly or indirectly linked to the moiety configured to support cell growth, viability, portability, or any combination thereof. The first moiety may be directly (n=0) or indirectly (n=1) linked to the second moiety, which is the moiety configured to support cell growth, viability, portability, or any combination thereof via connection to a first end of a linker L. The linker L may further include a linear portion wherein a backbone of the linear portion may have 1 to 200 non-hydrogen atoms selected from any combination of silicon, carbon, nitrogen, oxygen, sulfur and phosphorus atoms. The backbone of the linear portion may further include one or more arylene moieties. The second moiety of the surface conditioning reagent ("moiety") may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acid; or amino acids. The second moiety of the surface conditioning reagent may include alkyl or perfluoroalkyl moieties. The alkyl or perfluoroalkyl moieties may have a backbone chain length of greater than 10 carbons. The second moiety of the surface conditioning reagent may include saccharide moieties, and may be dextran. In other embodiments, the second moiety of the surface conditioning reagent may include alkylene ether moieties. The alkylene ether moieties may be polyethylene glycol. The surface conditioning reagent may further include a cleavable moiety, which may be located within the linker L or may be part of the second moiety of the surface conditioning reagent. The cleavable moiety may be configured to permit disruption of the conditioned surface thereby promoting portability of the one or more biological cells.

In various embodiments, the modifying reagent may include a surface modifying reagent, having a structure of Formula 4 as defined above, where the surface modifying reagent includes a first moiety LG configured to react with the surface and a second moiety $R_x$ which may be or may be modified to include a reactive moiety including azido, amino, bromo, a thiol, an activated ester, a succinimidyl or alkynyl moiety, thereby converting the surface into a surface comprising a surface modifying ligand, having a structure of Formula 3, as described above. In some embodiments, the first moiety of the surface modifying reagent, which is configured to react with the oxides of the surface, may be a siloxane or a phosphonic acid.

In some embodiments, the method includes a step of reacting the surface comprising a surface modifying ligand (Formula 3) with a conditioning modification reagent including a first moiety configured to support cell growth, viability, portability, or any combination thereof, and a second moiety $R_{px}$ configured to react with the reactive moiety of the surface modifying ligand; thereby providing a surface conditioned to support cell growth, viability, portability, or any combination thereof of a biological cell, having a structure of Formula 2, as described above. The conditioning modification reagent may have a structure of Formula 5. In some embodiments, the first moiety of the conditioning modification reagent comprises at least one of an alkylene oxide moiety, amino acid moiety, a saccharide moiety, an anionic moiety, a cationic moiety and a zwitterionic moiety.

In various embodiments, any of the surface conditioning reagent, surface modifying reagent or the conditioning modification reagent may further include a cleavable moiety as described herein.

Conditioned Surface Containing Other Components.

The conditioned surface may additionally include other components, other than or in addition to a polymer or a conditioned surface formed by a covalently linked moiety, including biologically compatible metal ions (e.g., calcium, sodium, potassium, or magnesium), antioxidants, surfactants, and/or essential nutrients. A non-limiting exemplary list includes vitamins such as B7, alpha-tocopherol, alpha-tocopherol acetate, vitamin A and its acetate; proteins such as BSA, Catalase, Insulin, Transferrin, Superoxide Dismutase; small molecules such as corticosterone, D-galactose, ethanolamine hydrochloride, reduced glutathione, L-carnitine hydrochloride, linoleic acid, linolenic acid, progesterone, putrescine dihydrochloride, and triiodo-thyronine; and salts, including but not limited to sodium selenite, sodium phosphate, potassium phosphate, calcium phosphate, and/or magnesium phosphate. Antioxidants may include but are not limited to carotenoids, cinnamic acids and derivatives, ferulic acid, polyphenols such as flavonoids, quinones and derivatives (including mitoquinone-Q), N-acetyl cysteine, and antioxidant vitamins such as ascorbic acid, vitamin E and the like. The conditioned surface may include a culture medium supplement such as B-27® Supplement, which contains antioxidants and many of the other components listed above. B-27® Supplement is commercially available (50λ), serum free from ThermoFisher Scientific, (Cat #17504044).

In some embodiments, the at least one conditioned surface may include one or more components of mammalian serum. In some embodiments, the mammalian serum is Fetal Bovine Serum (FBS), or Fetal Calf Serum (FCS). The conditioned surface may include specific components of mammalian serum such as specific amounts and types of proteins usually found in serum, which may be provided in defined amounts and type from serum free or defined media.

In other embodiments, the at least one conditioned surface does not include a mammalian serum. In various embodiments, the at least one conditioned surface may not include any titanium, nickel, or iron metal ions. In yet other embodiments, the at least one conditioned surface may not include any significant concentration of titanium, nickel, or iron metal ions. In yet another embodiment, the at least one conditioned surface may not include any gold, aluminum, or tungsten metal ions.

Reagent Treatment to Reduce Adhesion. Cocktail of Reagents.

As cells are cultured within a microfluidic device, the cells actively secrete proteins and other biomolecules and passively exude similar biomolecules which can adhere to the surfaces within the microfluidic device. The cells in culture may adhere to each other or to the conditioned surface, and become difficult to remove from the growth chamber, in order to export from the microfluidic device. Additionally, under some circumstances, it may be desirable to bring additional cells, of the same or different type from the culturing cells, into the microfluidic device. These newly delivered cells may also become adhered to the surface fouling accumulated within the microfluidic environment, and present difficulties in removing from the device at a later time point.

Treatment with proteases such as trypsin or Accutase® (an enzymatic mixture having proteolytic and collagenolytic activity, Innovative Cell Technologies) may not provide sufficient efficacy to, for one non-limiting example, permit exportation of the adhered cells from the microfluidic device. One or more proteins and/or peptides that provide anti-adhesive properties may be used as a cocktail to reduce such adherence for both scenarios. Biomolecules or small molecules having activity against one of a variety of cell adherence mechanisms may be used. Some of the cell adhesion mechanisms that may be inhibited may be active actin filament formation and related processes, which may be targeted by use of compounds such as Cytochalasin B (New England Biosciences Cat No: M0303S), a small molecule inhibitor of microfilament extension. Specific receptor driven adhesion processes, such as, but not limited to inhibition of integrin receptors mediating adhesion to fibronectin (which may be found on a fouled surface) may be targeted, by use of, for example RGD containing peptides. Another type of fouling materials, that of nucleic acids released from dead cell, may attract cell binding, which may be targeted by use of an endonuclease which will cleave fouling nucleic acids. One specific endonuclease, deoxyribonuclease 1 (DNase 1, Sigma Aldrich, Catalog No. AMPD1-1KT) also binds to actin, thus providing a dual activity blockage of adherence. In some embodiments, a cocktail of all three blocking agents may be used to prevent/reduce cell adherence.

General Treatment Protocol. After Culture:

For cells that have been growing within a microfluidic device for 2, 3, 4 days or more, the cocktail of the three anti-adhesion reagents or single anti-adhesion reagent as described below, may be flowed into the microfluidic device and allowed to diffuse into the growth chamber for a period of time from about 20 min, 30 min, 40 min, 50 min, or 60 min before exporting the cells.

Pre-Treatment:

For cells to be imported into a microfluidic device, the cells may be pre-incubated in a culture medium containing the cocktail or the single anti-adhesion reagent for about 30 min, and then imported to the microfluidic chip. The inhibition persists without further addition of reagent, for periods of time of 1, 2, 3, or more hours.

RGD tripeptide (mw. 614.6, Santa Cruz Biotechnology Cat No: sc-201176) may be present in the culture medium or pre-importation incubation medium in a concentration of about 0.1 mM to about 20 mM. In some embodiments, the RGD tripeptide may be present at a concentration of about 0.1, 0.5, 0.7, 1.0, 3.0, 5.0 6.0, 8.0, 10.0 millimolar, or any value within that range. Cytocholasin B may be present in the pre-importation incubation medium at a concentration of about 0.01 micromolar to about 50 micromolar, or at about 0.01, 0.05, 0.1, 2, 4, 6, 8, 10, 20, 30, 50 micromolar, or any value within the range. DNase 1 may be present at a concentration of about 0.001 U/microliter to about 10 U/microliter, or at about 0.001, 0.005, 0.01, 0.05, 1.0, 5.0, 10 U/microliter, or any value within that range.

In some embodiments, a single reagent may be used to reduce adhesion before or after cells have been cultured in a microfluidic device. For example, RGD tripeptide may be used at a concentration of 5 mg/ml either for pre-incubation or may be flowed in as a treatment within the microfluidic device prior to export.

Another inhibitor which may be used is a tetrapeptide fibronectin inhibitor (Arg-Gly-Asp-Ser-OH, mw. 433.4, Santa Cruz Biotechnology Cat No: sc-202156)). The fibronectin inhibitor may be used at a concentration of about 1.75 micrograms/ml (4 micromolar).

Similarly to the use of the protein or small molecule reagents to reduce or prevent adhesion, antibodies to extracellular adhesion related proteins may be used to effect export and portability within the microfluidic device. One non limiting example is anti-B1 integrin: clone M-106. (Santa Cruz Biotechnology Cat No: sc-8978).

Conditioned Surface Containing a Cleavable Moiety.

In some embodiments, the conditioned surface may have cleavable moieties incorporated within the covalently or non-covalently linked molecules of the conditioned surface. The conditioned surface may include a peptide motif such as RGD, having a function as above, or it may have another peptide motif that promotes cell growth or provides contact cues for cell proliferation. In other embodiments, the conditioned surface provides nonspecific support for the cells, and may act to simply buffer the cells from the silicon or aluminum oxide surfaces of the microfluidic device. It may be desirable, after a period of cell culture is completed, to disrupt the conditioned surface, to promote export of the expanded cell population within a growth chamber of the microfluidic device. This may be useful when cells demonstrate adherent behavior. The conditioned surface may be disrupted, partially or fully removed by incorporating other peptide motifs that are substrates for a protease that is not highly secreted by the cells of interest. In one non-limiting example, a peptide motif of ENLYQS (Glu-Asn-Leu-Tyr-Gln-Ser) may be incorporated at pre-designed intervals into a conditioned surface. This motif is a substrate for TEV protease (Tobacco Etch Virus cysteine protease, Sigma Aldrich catalog no. T4455) which is highly sequence specific, and therefore useful for highly controlled cleavage. After the culture period is completed, TEV protease may be flowed into the microfluidic device and allowed to diffuse into the isolation region of the growth chambers. The conditioned surface is then disrupted, facilitating export of the cells within the microfluidic device. Therefore, a variety of other proteolytic motifs may be designed and incorporated into a conditioned surface, to be cleaved by a suitably specific protease as one of skill in the art can devise.

Fluidic Medium.

With regard to the foregoing discussion about microfluidic devices having a channel and one or more growth chambers, a fluidic medium (e.g., a first medium and/or a second medium) can be any fluid that is capable of maintaining a cell in a substantially viable state. The viable state will depend on the biological micro-object and the culture experiment being performed.

The first and/or second fluidic medium may provide both fluidic and dissolved gaseous components necessary for cell viability, and may also maintain pH in a desired range, using either buffered fluidic media or pH monitoring or both.

If the cell is a mammalian cell, the first fluidic medium and/or the second fluidic medium may include mammalian serum or a defined serum free medium as is known in the art, which is capable of providing essential nutrients, hormones, growth factors or cell growth signals. Similarly to the conditioned surface above, the first fluidic medium and/or the second fluidic medium may include Fetal Bovine Serum (FBS), or Fetal Calf Serum (FCS). Alternatively, the first fluidic medium and/or the second fluidic medium may not include any animal sourced serum but may include a defined medium which may include any or all of physiologically relevant metal ions (including but not limited to sodium, potassium, calcium, magnesium, and/or zinc) antioxidants, surfactants, and/or essential nutrients. The defined medium may be serum free, while still containing some proteins, where the proteins are of defined amount and type. A non-limiting exemplary list of components in a serum free medium includes vitamins such as B7, alpha-tocopherol, alpha-tocopherol acetate, vitamin A and its acetate; proteins such as BSA, Catalase, Insulin, Transferrin, Superoxide Dismutase; small molecules such as corticosterone, D-galactose, ethanolamine hydrochloride, reduced glutathione, L-carnitine hydrochloride, linoleic acid, linolenic acid, progesterone, putrescine dihydrochloride, and triiodo-thyronine; and salts, including but not limited to sodium selenite, sodium phosphate, potassium phosphate, calcium phosphate, and/or magnesium phosphate. The fluidic medium may contain any of the antioxidants described above for the conditioned surface.

The fluidic medium may be sterile filtered through a 0.22 micron filter unit (VWR, Cat. No. 73520-986).

In some embodiments, a suitable culture medium may include or may be composed entirely of any of Dulbecco's Modified Eagle's medium (ThermoFisher Scientific, Cat #11960-051); FreeStyle™ Medium (Invitrogen, ThermoFisher Scientific, Cat. No. 11960-051); RPMI-1640 (GIBCO®, ThermoFisher Scientific, Cat. No. 11875-127); Hybridoma-SFM (ThermoFisher Scientific, Cat. No. 12045-076); Medium E (Stem Cell, Cat. No. 3805); 1×CD CHO Medium (ThermoFisher Scientific, Cat. No. 10743-011); Iscove's Modified Dulbecco's Medium (ThermoFisher Scientific, Cat. No. 12440-061); or CD DG44 medium (ThermoFisher Scientific, Cat. No. 10743-011).

The culture medium may additionally include Fetal Bovine Serum (FBS, available from GIBCO®, ThermoFisher Scientific), Heat Deactivated Fetal Bovine Serum; or Fetal Calf Serum (FCS, Sigma-Aldrich Cat Nos. F2442, F6176, F4135 and others). FBS may be present at a concentration of about 1% to about 20% v/v; about 1% to about 15% v/v, about 1% to about 10% v/v, or about 1% to about 5% v/v, or any number within any of the ranges. The culture medium may additionally include Human AB serum (Sigma-Aldrich, Cat. No. S2146), and may be present in a concentration of about 1% to about 20% v/v; about 1% to about 15% v/v, about 1% to about 10% v/v, or about 1% to about 5% v/v, or any number within any of the ranges.

The culture medium may additionally include penicillin-streptomycin (ThermoFisher Scientific, Cat. No. 15140-163). The pen-strep may be present in a concentration in a range of about 0.01% to about 10% v/v; about 0.1% to about 10% v/v; about 0.01% to about 5% v/v; about 0.1% to about 5% v/v; about 0.1% to about 3% v/v; about 0.1% to about 2% v/v; about 0.1% to about 1% v/v; or any value within any of the ranges. In other embodiments, the culture medium may include geneticin (ThermoFisher Scientific, Cat. No. 101310-035). Geneticin may be present in a concentration of about 0.5 micrograms/ml; about 1.0 micrograms/ml; about 5.0 micrograms/ml; about 10.0 micrograms/ml; about 15 micrograms/ml; about 20 micrograms/ml; about 30 micrograms/ml; about 50 micrograms/ml; about 70 micrograms/ml; about 100 micrograms/ml; or any value in these ranges.

The culture medium may include a buffer. The buffer may be one of Good's buffers. The buffer may be, but is not limited to 4-(2-hydroxyethyl)-1-piperazineethanesulfonic acid (HEPES)(ThermoFisher Scientific, Cat. No. 15630-080. The buffer may be present in a concentration of about 1 millimolar; about 3 millimolar; about 5 millimolar; about 7 millimolar; about 9 millimolar; about 10 millimolar; about 12 millimolar; about 15 millimolar; about 20 millimolar; about 40 millimolar; about 60 millimolar; about 100 millimolar; or any values in these ranges.

The culture medium may additionally include a dipeptide substitute for glutamine, GlutaMAX™ (GIBCO® Thermo-Fisher Scientific, Cat No. 35050-079). The substitute for glutamine may be present in a concentration of about 0.2 millimolar; about 0.5 millimolar; about 0.7 millimolar; about 1.0 millimolar; about 1.2 millimolar; about 1.5 millimolar; about 1.7 millimolar; about 2.0 millimolar; about 2.5 millimolar; about 3.0 millimolar; about 4.0 millimolar; about 7.0 millimolar, or about 10.0 millimolar, or any value in these ranges. The culture medium may include MEM non-essential Amino Acid (ThermoFisher Scientific, Cat. No. 10370-088). The MEM non-essential Amino Acid may be present in a concentration of about 0.2 millimolar; about 0.5 millimolar; about 0.7 millimolar; about 1.0 millimolar; about 1.2 millimolar; about 1.5 millimolar; about 1.7 millimolar; about 2.0 millimolar; about 2.5 millimolar; about 3.0 millimolar; about 4.0 millimolar; about 7.0 millimolar, or about 10.0 millimolar, or any value in these ranges.

The culture medium may additionally contain glucose (ThermoFisher Scientific, Cat. No. 15023-021). Glucose may be present in a concentration of about 0.1 g/L; about 0.3 g/L; about 0.5 g/L; about 0.8 g/L; about 1.0 g/L; about 1.5 g/L; about 2.0 g/L; about 2.5 g/L; about 3.0 g/L; about 3.5 g/L; about 4.0 g/L; about 5.0 g/L; about 7.0 g/L; about 10.0 g/L; or any values in these ranges.

The culture medium may additionally include mercaptoethanol (ThermoFisher Scientific, Cat. No. 31350-010). Mercaptoethanol may be present in a concentration of about about 0.001% to about 1.5% v/v; about 0.005% to about 1.0% v/v; about 0.01% to about 1.0% v/v; about 0.15% to about 1.0% v/v; about 0.2% to about 1% v/v; or any value in these ranges.

The culture medium may include OPI culture medium additive, including oxaloacetate, pyruvate, and insulin (Sigma-Aldrich, Cat. No. 0-5003). OPI culture medium additive may be present in a concentration of about 0.001% to about 1.5% v/v; about 0.005% to about 1.0% v/v; about 0.01% to about 1.0% v/v; about 0.15% to about 1.0% v/v; about 0.2% to about 1% v/v; or any value in these ranges. The culture medium may contain B-27 supplement (50×), serum free (ThermoFisher Scientific, Cat. No. 17504-163). B-27 supplement may be present in a concentration of about 0.01% to about 10.5% v/v; about 0.05% to about 5.0% v/v; about 0.1% to about 5.0% v/v; about 0.5% to about 5% v/v; or any value in these ranges.

As described herein, a culture medium or an additive for a culture medium may include one or more Pluronic® polymers useful for yielding a conditioned surface, and may include Pluronic® L44, L64, P85, F68 and F127 (including F127NF). The Pluronic® polymer may be present in the culture medium at a concentration of about 0.001% v/v to about 10% v/v; about 0.01% v/v to about 5% v/v; about 0.01% v/v to about 1% v/v, or about 0.05% to about 1% v/v. For a culture medium additive which may be provided as a kit, the concentration may be 1×, 5×, 10×, 100×, or about 100× the final culture medium concentration.

The culture medium may include IL 6 (Sigma-Aldrich, Cat. No. SRP3096-20UG). IL 6 may be present in a concentration of about 1 nM; about 5 nM, about 10 nM, about 15 nM, about 20 nM, about 25 nM, about 30 nM, about 40 nM, about 50 nM or any values in these ranges.

The culture medium may additionally include sodium pyruvate (ThermoFisher Scientific, Cat. No. 11360-070). The substitute for glutamine may be present in a concentration of about 0.01 millimolar; about 0.02 millimolar; about 0.04 millimolar; about 0.06 millimolar; about 0.08 millimolar; about 0.1 millimolar; about 0.5 millimolar; about 0.7 millimolar; about 1.0 millimolar; about 1.2 millimolar; about 1.5 millimolar; about 1.7 millimolar; about 2.0 millimolar; about 2.5 millimolar; about 3.0 millimolar; about 4.0 millimolar; about 7.0 millimolar, or about 10.0 millimolar, or any value in these ranges.

Gaseous Environment.

The system provides a mixture of gases necessary for cell viability, including but not limited to oxygen and carbon dioxide. Both gases dissolve into the fluidic medium, and may be used by the cells, thus altering over time the gas content of the fluidic medium in an isolation region of a growth chamber. In particular, carbon dioxide content can change over time, which affects the pH of the fluidic media in the microfluidic device. In some experimental conditions, non-optimal oxygen partial pressure may be used.

Temperature Control.

In some embodiments, the at least one conditioned surface of the growth chamber(s) and/or flow region(s) is conditioned by controlling the temperature of the at least one conditioned surface. The system may include a component that can control and modulate the temperature of the at least one conditioned surface of the growth chambers and/or flow regions of the microfluidic device. The system may include Peltier heating, resistive heating, or any other suitable method for providing temperature modulation to the microfluidic device. The system may also include sensors and/or feedback components to control heat input to a predetermined range. In some embodiments, the at least one conditioned surface has a temperature of at least about 25° C., 26° C., 27° C., 28° C., 29° C., 30° C., 31° C., 32° C., 33° C., 34° C., 35° C., 36° C., 37° C., 38° C., 39° C., or about 40° C., and is stable at that temperature. In some embodiments, the at least one surface has a temperature greater than about 25° C. In other embodiments, the at least one surface has a temperature in the range from about 30°-40° C.; about 35°

C. to about 38° C.; or about 36° C. to about 37° C. In some embodiments, the at least one conditioned surface has a temperature of at least about 30° C.

Flow Controller Providing Perfusion During Incubation.

The flow controller may perfuse the first fluidic medium in the flow region, as described above, during the incubation period to provide nutrients to the cells in growth chambers and to carry waste away from the growth chambers, where the exchange of nutrients and removal of waste occurs substantially via diffusion. The controller may be a separate component from the microfluidic device or may be incorporated as part of the microfluidic device. The flow controller may be configured to perfuse the medium in the flow region non-continuously. The flow controller may be configured to perfuse the medium(s) in a periodic manner, or an irregular manner.

In some other embodiments, the controller may be configured to perfuse the fluidic medium(s) in the flow region once about every 4 h, 3 h, 2 h, 60 min, 57 min, 55 min, 53 min, 50 min, 47 min, 45 min, 43 min, 40 min, 37 min, 35 min, 33 min, 30 min, 27 min, 25 min, 23 min, 20 min, 17 min, 15 min, 13 min, 10 min, 7 min or 5 min. In some embodiments, the controller may be configured to perfuse the fluidic medium once about every 5 min to about every 20 min. In other embodiments, the controller may be configured to perfuse the fluidic medium once about every 15 min to about every 45 min. In yet other embodiments, the controller may be configured to perfuse the fluidic medium once every 30 min to about every 60 min. In other embodiments, the controller may be configured to perfuse the fluidic medium once every 45 min to about every 90 min. In some other embodiments, the controller may be configured to perfuse the fluidic medium once every 60 min to about 120 min. Alternatively, the controller may be configured to perfuse the fluidic medium once every 2 h to every 6 h.

In some embodiments, the controller 226 may be configured to perfuse the medium for a period of time that may be about 5, 10, 15, 20, 25, 30, 35, 40, 45, 50, 55, 60, 65, or 70 sec. In other embodiments, the controller may be configured to perfuse the medium for about 1 min, 1.2 min, 1.4 min, 1.5 min, 1.6 min, 1.8 min, 2.0 min, 2.2 min, 2.4 min, 2.5 min, 2.6 min 2.8 min, 3.0 min, 3.2 min, 3.4 min, 3.5 min, 3.6 min, 3.8 min, or 4.0 min.

In various embodiments, the controller may be configured to perfuse the medium for about 5 sec to about 4 min, about 10 sec to about 3.5 min, about 15 sec to about 3 min, about 15 sec to about 2 min, about 25 sec to about 90 sec about 30 sec to about 75 sec, about 40 sec to about 2.0 min, about 60 sec to about 2.5 min, about 90 sec to about 3.0 min, or 1.8 min to about 4 min.

The flow controller (not shown) may be configured to perfuse the first fluidic medium in the flow region at a rate that is much greater than the average rate of diffusion of components from the isolation region of the growth chambers to the flow channel. For example, the rate of fluid flow in the flow region may be about 0.009, 0.01, 0.02, 0.03, 0.05, 0.1, 0.2, 0.3, 0.4, 0.5, 0.6, 0.7, 0.8, 0.9, 1.0, 1.1, 1.2, 1.3, 1.4, 1.5, 1.7, 1.9, 2.0, 2.2, 2.4, 2.6, 2.8, 3.0, 3.2, 3.4, 3.6, 3.8, 4.0, 4.2, 4.4, 4.6, 4.8, 5.0, 6.0, 7.0, 8.0 or 9.0 microliters/sec, any of which is a rate of velocity that will sweep a connection region of the growth chamber (but will not sweep an isolation region of the growth chamber(s). The controller may be capable of providing a velocity of first fluidic medium which is a non-sweeping rate of fluidic medium velocity, i.e., any suitable rate below the $V_{max}$, the maximal velocity for the microfluidic device that avoids rupture of the microfluidic device due to excessive pressure and limits the movement of components between a second fluidic medium in the growth chamber and a first fluidic medium in the flow region to diffusion. In some embodiments, the controller may be configured to perfuse the first fluidic medium through the flow region at about 0.05, 0.06, 0.07, 0.08, 0.09, 0.10, 0.11, 0.12, 0.13, 0.14, 0.15, 0.16, 0.17, 0.18, 0.19, 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, 2.00, 2.10, 2.20, 2.30, 2.40, 2.50, 2.60, 2.70, 2.80, 2.90, or 3.00 microliters/sec. In some embodiments, the controller may be configured to perfuse the first fluidic medium through each of a plurality of flow regions at about 0.01, 0.02, 0.03, 0.04, 0.05, 0.06, 0.07, 0.08, 0.09, 0.10, or about 0.11 microliters/sec.

In various embodiments, the rate of flow and duration of perfusion provides a total amount of the first fluidic medium at least about 3, 4, 5, 6, 7, 8, 9, 10, 11, 15, 20, 25, 30, 35, 50, 75, 100, 200, 300, or more volumes of the flow channel.

Figure 7:
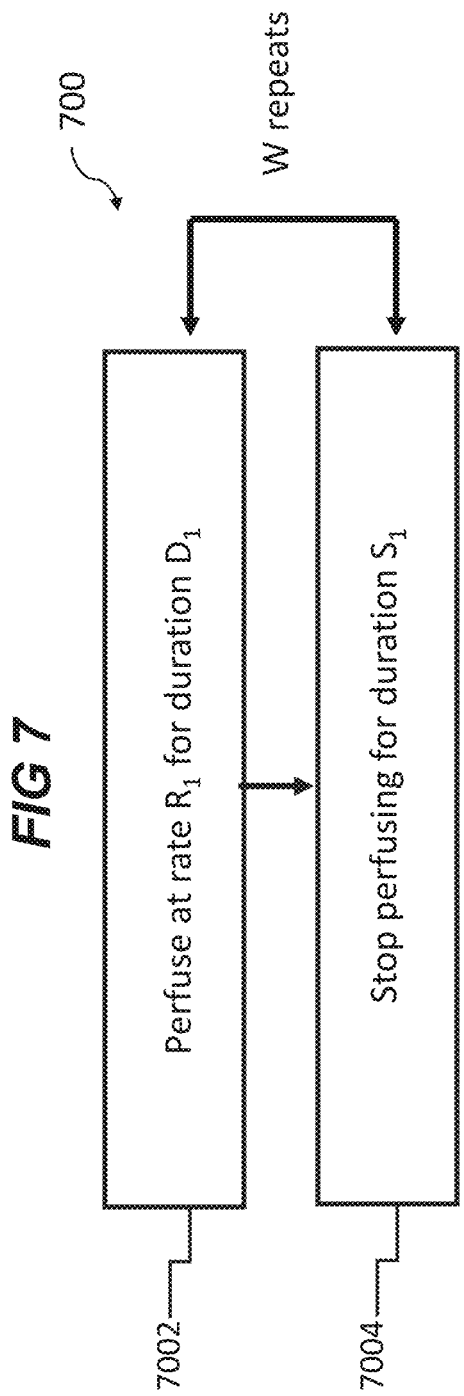
FIG. 7 is an example of one embodiment of a process for perfusing a fluidic medium in a microfluidic device.
Figure 8:
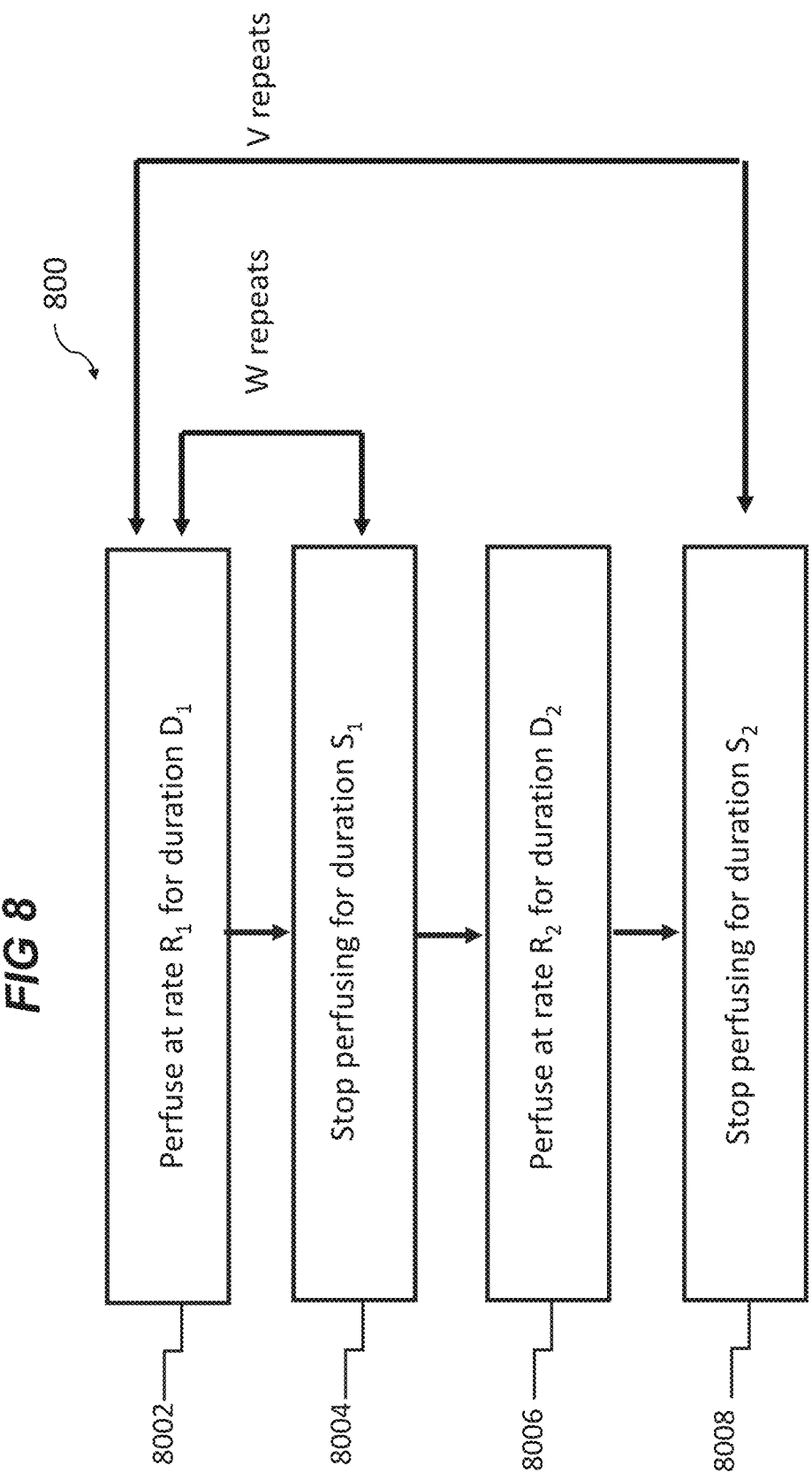
FIG. 8 is an example of another embodiment of a process for perfusing a fluidic medium in a microfluidic device.

In various embodiments, perfusion may be accomplished using varying durations of time, varying flow rates, and perfusion stop duration times as shown in the methods of FIGS. 7 and 8 and discussed below.

Reservoir, Medium Conditioning, and Introduction Components.

The system may further include a reservoir configured to contain the fluidic medium which may be introduced at the inlet port 124 of the microfluidic device and may be perfused by the flow controller. The reservoir may be fluidically connected to any of the microfluidic devices as described herein (non-limiting examples include 100, 200, 240, 290 or 400) at an upstream location. (FIGS. 5A-E). The fluidic medium may be conditioned in the reservoir to contain the desired balance of gases, i.e., for one non-limiting example, a mixture containing 5% carbon dioxide which provides optimized growth for cells under culture, and may also moderate pH in the microfluidic device.

In some embodiments, the reservoir may further contain a population of cells different from the cells under study in the microfluidic device. This population of cells may be feeder cells which produce soluble signaling or growth factors necessary for growth and/or viability by the cells in the microfluidic device. In this manner, the fluidic medium may be conditioned for optimized growth and/or viability prior to introduction to the microfluidic device. Using the reservoir to house the feeder cell population may prevent contamination of the population of cells under culture in the microfluidic device; the soluble secretions from the feeder cells may be incorporated into the fluidic medium delivered into the microfluidic device, but the feeder cells may not be drawn up with the fluidic medium.

One embodiment of a reservoir, conditioning and introduction component of the system is shown in FIG. 5A. The reservoir in this embodiment may be another microfluidic device 502, which contains fluidic medium 202 (not shown) which is conditioned within the microfluidic device 502. Microfluidic device 502 has an enclosure 510 and a base 512, at least one of which is gas permeable. Microfluidic device 502 also may contain a population of feeder cells being maintained such that the feeder cells produce soluble growth factors or other cell signaling components necessary for growth and/or viability of the cell(s) in microfluidic device 500A. Reservoir 502 may be housed within a chamber 516, providing a 5% carbon dioxide gaseous environment, for one non-limiting example of a gaseous environment. Fluidic medium 202 in reservoir 502 absorbs the gaseous mixture (e.g., 5% carbon dioxide in air) through the gas permeable walls of the reservoir, and also absorbs the soluble secretions from the feeder cells. The medium 202 is perfused by pump 514 through gas impermeable connecting conduit 506 from the reservoir 502 into microfluidic device 500A via inlet port 124 and forms flow 212 in flow channel 134 of microfluidic device 500A. In this embodiment, none of pump connecting conduit 504 (not labelled), transfer connecting conduit 506, base 104 or enclosure 102 is gas permeable. The fluidic medium flow 212 sweeps past growth chambers of the microfluidic device 500A and permits diffusion of waste components of fluidic medium 204 out of the growth chambers (not shown) while permitting diffusion of components from fluidic medium 202 in the flow channel 134 into the growth chambers. Eventually, spent fluidic medium 202' (not shown) exits microfluidic device 500A via export port 124' in export connecting conduit 508.

Figure 5B:
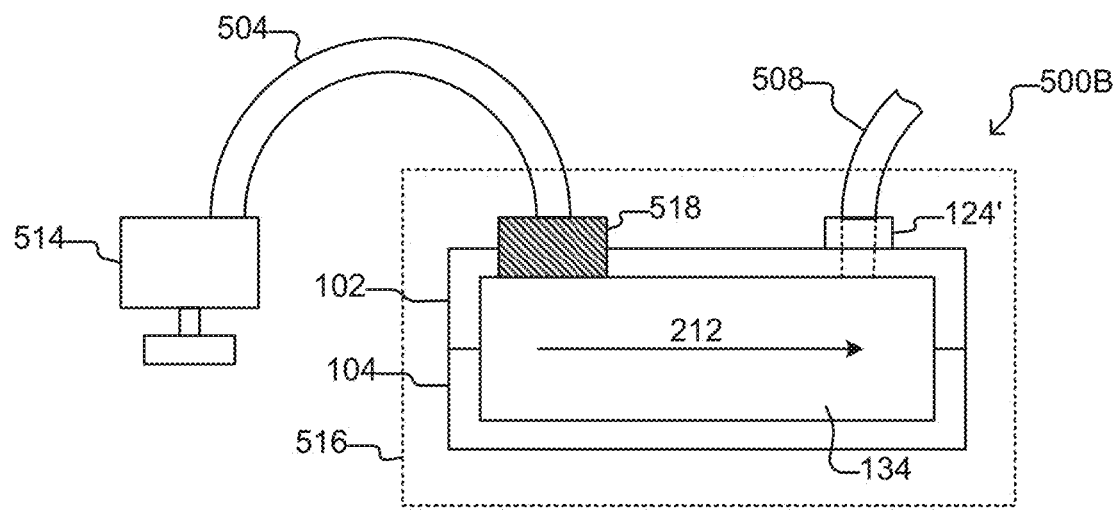

In another embodiment, fluidic medium 202 is transferred into the microfluidic device 500B via pump connecting conduit 504 and through gas permeable block 518, as shown in FIG. 5B. Gas permeable block 518 is incorporated into and forms a portion of the upper surface of the enclosure 102. The portion of the upper surface of enclosure 102 formed by gas permeable block 518 may be upstream of the growth chambers of microfluidic device 500B. Microfluidic device 500B is housed within a chamber 516 which provides a gaseous environment (e.g., 5% carbon dioxide) which is exchanged into fluidic media in the microfluidic device 500B. The chamber 516 may additionally provide conditioning to the microfluidic device 500B for temperature and/or humidity. None of pump connecting conduit 504, enclosure 102 or base 104 are gas permeable, and the exchange through gas permeable block 518 may act as "lungs" to the microfluidic device 500B and properly condition the media within the microfluidic device 500B. In this embodiment, fluidic medium 202 may be additionally conditioned in another component prior to loading into pump 514, and may thus also contain, for example, secreted substances from a feeder cell culture.

Figure 5C:
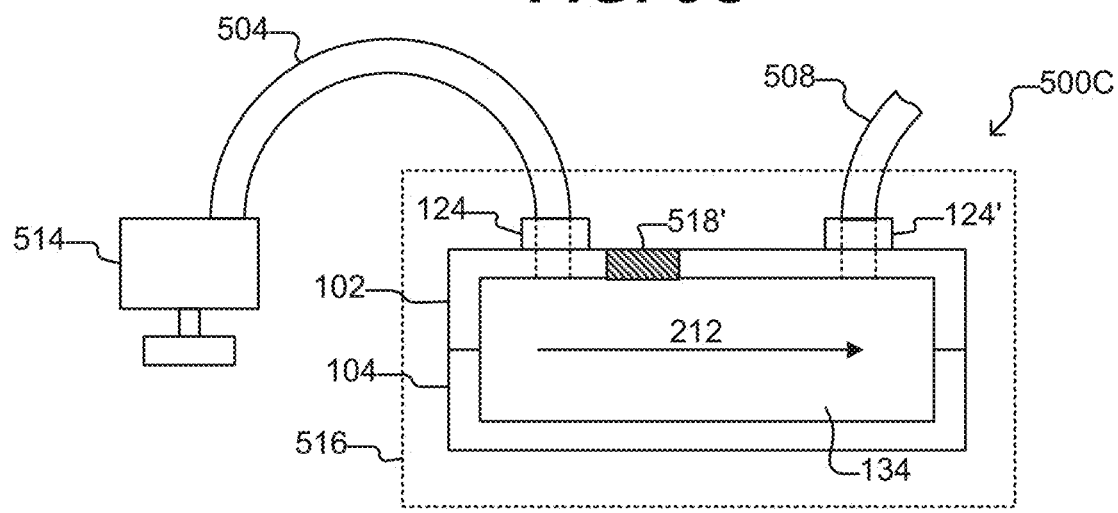

In another embodiment, the gas permeable block is integral to the upper surface of the enclosure 102 of microfluidic device 500C, forming a gas permeable section 518', as shown in FIG. 5C. Fluidic media may be conditioned and introduced as discussed above for the embodiment of FIG. 5B and may further include secreted substances from a feeder cell population. The microfluidic device 500C may be housed in a chamber 516 containing a gaseous environment, for instance 5% carbon dioxide in air. The gaseous environment can exchange across the gas permeable section 518', which can be one section or a plurality of sections in the upper surface of enclosure 102. The chamber 516 may further condition the device 500C for proper temperature and humidity. In this embodiment, the pump connecting conduit 504, enclosure 102 (other than the gas permeable block 518') and base 104 may be gas impermeable. In some embodiments, at least one gas permeable section 518' is located above a growth chamber of microfluidic device 500C. In another embodiment, at least one gas permeable section 518' is located above the flow region 134 of microfluidic device 500C. In yet other embodiments, gas permeable sections 518' may be located above both at least one growth chamber and at least one flow region 134.

Figure 5D:
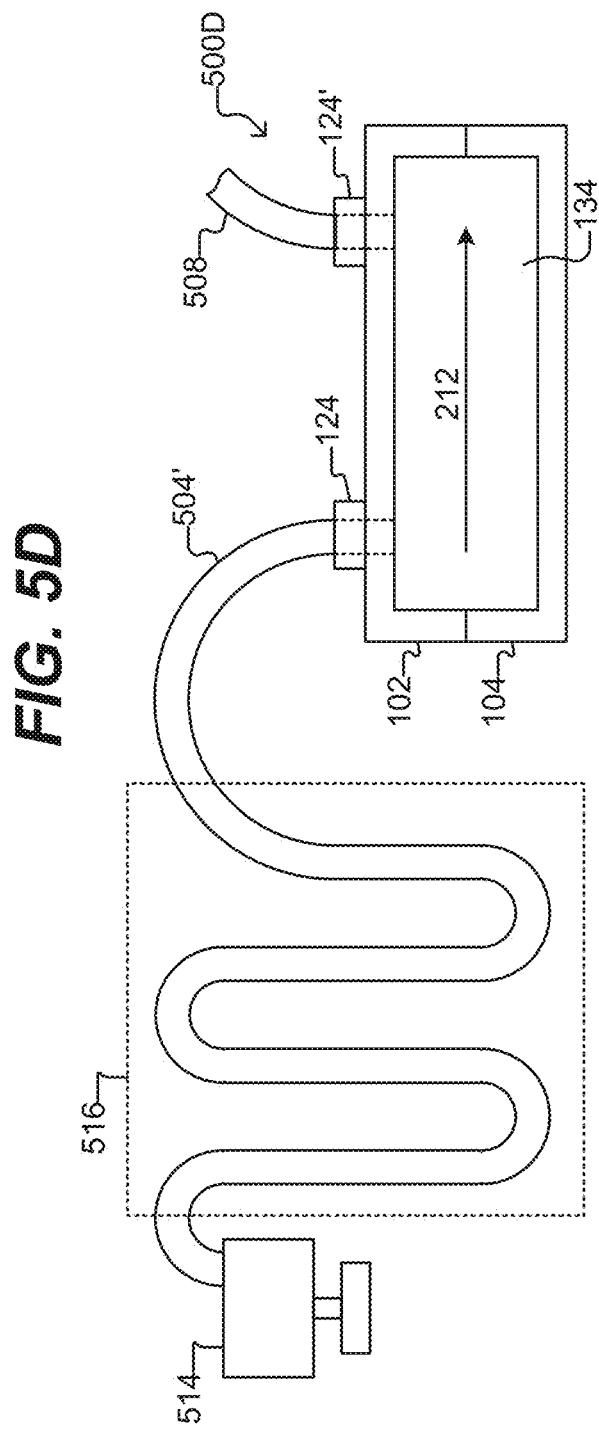

In a further embodiment, gas permeable tubing 504' may be used to condition (e.g. to equilibrate) the fluidic medium prior to the introduction of the medium into microfluidic device 500D, as shown in FIG. 5D. The length of the gas permeable tubing 504' may be selected to provide sufficient surface area to permit effective gas exchange and equilibration within an enclosure 516, which may contain a gaseous environment such as, in a non-limiting example, 5% carbon dioxide in air. The environment of 516 may further condition the media within gas permeable pump connecting conduit 504' for temperature and/or humidity. One non-limiting example of a gas permeable material that can be used for gas permeable connecting conduits is Teflon® AF. The fluidic medium may be conditioned prior to introduction to the pump component 514, by contact with a feeder cell population and resultingly may contain secreted substances which may optimize growth and/or viability of the cell(s) under culture in microfluidic device 500D. The prior conditioning with the feeder cell population may take place within the chamber 516 or may be performed in another culturing component having its own environmental controls for any of temperature, humidity, pH and/or gaseous environment. In this embodiment, enclosure 102 and base 104 of the microfluidic device 500D can be gas impermeable.

Figure 5E:
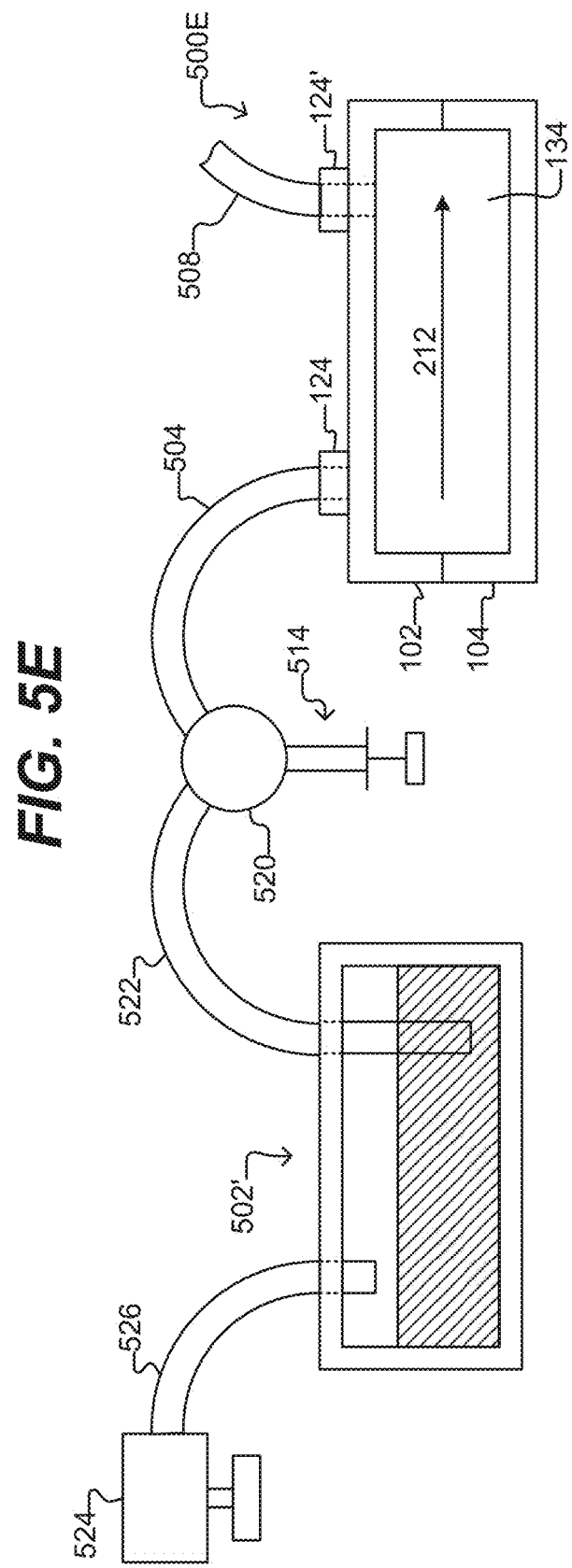

In yet another embodiment of the reservoir, medium conditioning and introduction components of the system, the medium may be conditioned in a reservoir 502' capable of being placed under an appropriate gaseous environment, as shown in FIG. 5E. The reservoir 502' does not need to be a microfluidic device or any particular type of culture component. The reservoir 502' is placed under an appropriate gaseous environment, such as, for example, 5% carbon dioxide in air, by providing a connecting feed 526 from a gaseous environment source 524. Fluidic medium within the reservoir 502' has gaseous exchange with the gaseous environment provided from source 524, and is thereby conditioned. The fluidic medium in the reservoir 502' may also contain a culture of feeder cells to provide secreted substances that may optimize growth and/or viability of cells under culture in microfluidic device 500E. Conditioned fluidic medium may be transferred from reservoir 502' via transfer connecting conduit 522, which connects to a valve 520 on a pump 514, and may be injected by the pump 514 into channel 134 of microfluidic device 500E via connecting conduit 504. Fluidic medium injected into microfluidic device 500E forms fluidic flow 212. After traversing flow channel 134, the spent fluidic medium 202' exits microfluidic device 500E via export conduit 508. In this embodiment, transfer connecting conduit 522, connecting conduit 504, valve 520, pump 514, enclosure 102, and base 104 may all be gas impermeable. In some embodiments, connecting conduit 526, connecting the source 524 to the reservoir 502', may be substantially gas impermeable. In other embodiments, the connecting conduit 526 does not need to be substantially gas impermeable but may be relatively gas impermeable.

In some embodiments of the system shown in FIG. 5E, the gas (not shown) may be either continuously flowing or may be pulsed, e.g., replaced periodically (not shown) imported from source 524 may be 5% carbon dioxide in air. In other embodiments, the gas imported from source 524 may be 100% carbon dioxide. When 100% carbon dioxide gas is used, small amounts of the carbon dioxide gas may be injected into the headspace (not shown) of the reservoir 502' to maintain the headspace at a 5% carbon dioxide mixture. In some embodiments, when gas is injected into the headspace of the reservoir 502', the reservoir 502' may further include a fan (not shown) to mix the injected gas with the other gaseous components (not shown) already present in the headspace (not shown). In some embodiments, where import of the gas is pulsed, the lid 102 of the microfluidic device 500E may have a carbon dioxide sensor (not shown) incorporated or attached therein. In some embodiments, 100% carbon dioxide gas may be imported from source 524 to save cost compared to the use of commercially available 5% carbon dioxide in air gas mixtures. In other embodiments, 100% carbon dioxide gas may be introduced into source 524 and mixed with air to prepare a 5% carbon dioxide mixture therein.

In any of the above embodiments, the chamber 516 may further be humidified such that the gaseous environment of the chamber does not change the osmolality of the fluidic medium in the microfluidic device and/or reservoir.

In another embodiment, an alternative approach to providing proper gaseous exchange to cells being cultured in the growth chambers may provide gas flow through the flow region of the microfluidic device (not shown). The appropriate gas (e.g., 5% carbon dioxide) may be pumped or pulsed directly through the flow channel Because the isolation regions of the growth chambers are designed to be mostly unswept volumes, the cells located therein are undisturbed by air or bubbles moving through the flow channel (swept region). This would provide very fast gas exchange between the gas in the flow channel and the fluidic medium inside the growth chambers because the diffusion distance is very small compared to, for example, the diffusion distance within a 50 mL conical tube. The gas may then be replaced by fluidic medium after any selected amount of time. Gas flow can be repeated at any desired frequency to keep the dissolved gaseous components at a stable concentration, which also has an effect on the pH of the fluidic medium. Alternatively, less than optimal gas composition or repetition may be used to perturb the environment of the cell.

In summary, there are a variety of components and configurations which may be used to provide conditioned media to cell(s) in growth chambers of the microfluidic devices described herein. Any of the microfluidic devices 100, 200, 240, 290 or 400 may be used with any of the embodiments of FIGS. 5A-5E. Systems and kits may include connecting conduits configured to connect to inlets and/or outlets of the microfluidic device. Connecting conduits may also be configured to connect to reservoirs and/or pump components.

Accordingly, a microfluidic device for culturing one or more biological cells is provided, including a flow region configured to contain a flow of a first fluidic medium; and at least one growth chamber comprising at least one surface conditioned to support cell growth, viability, portability, or any combination thereof within the microfluidic device, where the at least one growth chamber includes an isolation region and a connection region, the isolation region is fluidically connected with the connection region and the connection region includes a proximal opening to the flow region. In various embodiments, the isolation region of the microfluidic device may be configured to contain a second fluidic medium. When the flow region and the at least one growth chamber are substantially filled with the first and second fluidic media respectively, then components of the second fluidic medium may diffuse into the first fluidic medium and/or components of the first fluidic medium may diffuse into the second fluidic medium; and the first medium does not substantially flow into the isolation region. In various embodiments, the at least one conditioned surface may be conditioned to support portability of the one or more biological cells within the microfluidic device. In some embodiments, the moiety of the conditioned surface may be configured to support portability of the biological cells within the microfluidic device.

In some embodiments, the at least one conditioned surface of the microfluidic device may include a polymer including alkylene ether moieties. In other embodiments, the at least one conditioned surface of the microfluidic device may include a polymer comprising carboxylic acid moieties, sulfonic acid moieties, nucleic acid moieties, or phosphonic acid moieties. In yet other embodiments, the at least one conditioned surface of the microfluidic device may include a polymer including saccharide moieties. In some embodiments, the polymer including saccharide moieties may be dextran. In some other embodiments, the at least one conditioned surface of the microfluidic device may include a polymer comprising amino acid moieties.

Alternatively, the at least one conditioned surface of the microfluidic device may include one or more components of mammalian serum. The components of mammalian serum may be supplements for a culture medium. In some embodiments, the mammalian serum may be Fetal Bovine Serum (FBS), or Fetal Calf Serum (FCS).

In various embodiments of the microfluidic device, the at least one conditioned surface may include saccharide moieties. In some embodiments, the at least one conditioned surface may include alkylene ether moieties. In other embodiments, the at least one conditioned surface may include amino acid moieties. In some other embodiments, the at least one conditioned surface may include alkyl or perfluoroalkyl moieties. In some embodiments, the alkyl or perfluoroalkyl moieties may have a backbone chain length of greater than 10 carbons. In some embodiments, the at least one conditioned surface may include a moiety which may be alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to poly acrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments of the microfluidic device, the at least one conditioned surface may include a linking group covalently linked to a surface of the microfluidic device, and the linking group may be linked to a moiety configured to support cell growth, viability, portability, or any combination thereof within the microfluidic device. In some embodiments, the linking group may be a siloxy linking group. In other embodiments, the linking group may be a phosphonate linking group. In some embodiments, the linking group may be indirectly linked to the moiety configured to support cell growth, viability, portability, or any combination thereof. In some embodiments, the moiety of the conditioned surface may be configured to support portability of the biological cells within the microfluidic device. In other embodiments, the linking group may be directly linked to the moiety configured to support cell growth, viability, portability, or any combination thereof. In other embodiments, the linking group may be indirectly linked to the moiety configured to support cell growth, viability, portability, or any combination thereof, via a linker. In various embodiments, the linker may include a triazolylene moiety.

In various embodiments of the microfluidic device, the at least one conditioned surface may include zwitterions. In other embodiments, the at least one conditioned surface may include phosphonic acid moieties or carboxylic acid moieties. In yet other embodiments, the conditioned surface may include anions. In some other embodiments, the at least one conditioned surface may include amino or guanidine moieties. In other embodiments, the at least one conditioned surface may include cations.

In various embodiments of the microfluidic device, the at least one conditioned surface may include at least one cell adhesion blocking molecule. The at least one cell adhesion blocking molecule may disrupt actin filament formation, block integrin receptors, or reduces binding of cells to DNA fouled surfaces. The at least one cell adhesion blocking molecule may be Cytochalasin B, an RGD containing peptide, or a DNase 1 protein. In yet other embodiments, the at least one cell adhesion blocking molecule may include a combination of more than one type of cell adhesion blocking molecules.

In various embodiments of the microfluidic device, the at least one conditioned surface is configured to be heated to a temperature of at least about 30° C. The at least one conditioned surface may be configured to be stable at a temperature of at least about 30° C.

In various embodiments of the microfluidic device, the microfluidic device may further include a microfluidic channel comprising at least a portion of the flow region. In some embodiments, the connection region of the at least one growth chamber may open directly into the microfluidic channel. In some embodiments, the isolation region of the at least one growth chamber of the microfluidic device may have dimensions sufficient to support cell expansion to a range of about 100 cells. In some embodiments, no more than $1 \times 10^2$ biological cells may be maintained in the at least one growth chamber. In some embodiments, the volume of the at least one growth chamber may be less than or equal to about $2 \times 10^6$ cubic microns. In other embodiments, no more than $1 \times 10^2$ biological cells may be maintained in the at least one growth chamber, and the volume of the at least one growth chamber may be less than or equal to about $1 \times 10^7$ cubic microns.

In various embodiments of the microfluidic device, the microfluidic device may further include at least one inlet port configured to input the first or second fluidic medium into the flow region and at least one outlet port configured to receive the first medium as it exits from the flow region.

In various embodiments of the microfluidic device, the microfluidic device may further include a substrate having a dielectrophoresis (DEP) configuration configured to introduce one or more biological cells into or move the one or more biological cells out of the growth chamber. The DEP configuration may be optically actuated.

In various embodiments of the microfluidic device, the microfluidic device may further include a deformable lid region above the at least one growth chamber or the isolation region thereof, whereby depressing the deformable lid region exerts a force sufficient to export the biological cell from the isolation region to the flow region. In some embodiments, the microfluidic device may include a lid where at least a portion of the lid is gas permeable, thereby providing a source of gaseous molecules to a fluidic medium located in the microfluidic device. In some embodiments, the gas permeable portion of the lid may be located over the at least one growth chamber. In some embodiments, the gas permeable portion of the lid may be located over the flow region. In some embodiments, the microfluidic device may further include a deformable lid region above the at least one growth chamber or the isolation region thereof, whereby depressing the deformable lid region exerts a force sufficient to export the biological cell from the isolation region to the flow region.

In various embodiments of the microfluidic device, the conditioned surface may include a cleavable moiety. The cleavable moiety may be configured to permit disruption of the conditioned surface thereby promoting portability of the one or more biological cells after culturing.

In various embodiments of the microfluidic device, the at least one growth chamber may include a plurality of growth chambers.

In various embodiments of the microfluidic device, the one or more biological cells may include a plurality of biological cells. In some embodiments, the one or more biological cells may include one or more mammalian cells. In some embodiments, the one or more biological cells may include one or more hybridoma cells. In some embodiments, the one or more biological cells may include one or more lymphocyte or leukocyte cells. In other embodiments, the one or more biological cells may include a B cell, a T cell, NK cell, a macrophage, or a combination thereof. In various embodiments, the one or more biological cells may include one or more adherent cells. In some embodiments, the one or more biological cells in the growth chamber may be a single cell and the colony may be a clonal colony of biological cells.

pH Sensor.

Figure 6:
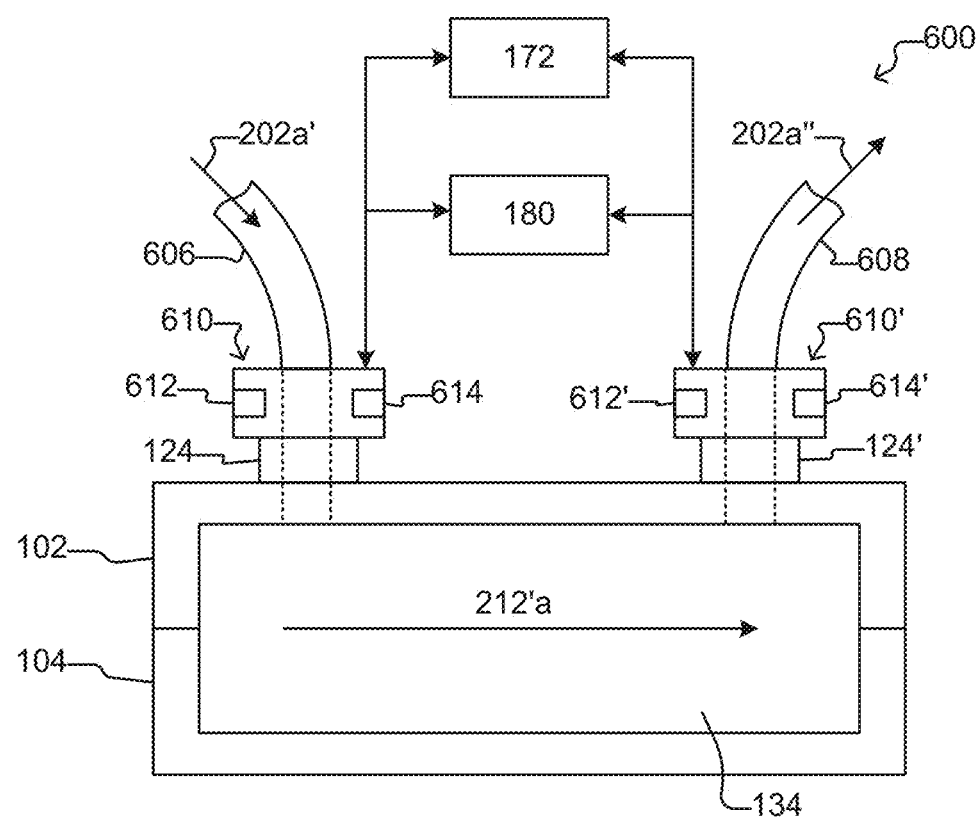
FIG. 6 is a representation of a microfluidic device having one or more sensors capable of detecting the pH of media entering and/or leaving the microfluidic device.

The system may further include at least one sensor connected to the at least one inlet port 124 and/or the at least one outlet port 124' of the microfluidic device 600 as shown in FIG. 6. Device 600 may alternatively be any one of devices 100, 200, 240, 290, 400, or 500A-E. The sensor may be configured to detect a pH of the first fluidic medium as it enters the microfluidic device 600. Alternatively, the sensor can be configured to detect a pH of the first fluidic medium as it exits the microfluidic device 600. The sensor may be incorporated into the microfluidic device or it may be a separate component capable of being attached to or in-line with an inlet port 124 and/or outlet port 124' of the microfluidic device.

In some embodiments, the pH sensor is an optical sensor. An optical sensor may provide an advantage over electrode-based benchtop apparatuses, as the electrode-based apparatus may include bulky probes, making the measurement of the pH of small (microliter) quantities of fluids difficult or impossible. Similarly, in-line flow-through solutions may have very long settling time (5 to 15 minutes) due to the nature of the microelectrodes, and may require extensive calibration procedures before each use. Furthermore, electrodes can deteriorate quickly, thus requiring more maintenance.

The optical sensor may be an integrated, electrode-less device including an LED for illumination and an integrated colorimeter sensor for visible color detection. The colorimeter sensor may be a color-sensitive phototransistor. The colorimeter sensor may detect in the visible light wavelength region, e.g., about 390 nm to about 700 nm Media stained with a pH dependent dye such as, but not limited to, Phenol Red, can provide instant and contactless optical signals. An optical electrode-less method of measurement using such an optical sensor requires neither contact with the medium nor calibration on the part of the user. Optical measurement can be calibrated to remove temperature dependence. Additionally, the use of an optical sensor minimizes the risk of fouling the sensor, thus reducing maintenance or replacement. The miniaturization of the light source (LED) and color sensor, also makes this amenable to test very small volumes of liquid (<1 microliter) and integration into portable or hand-held instruments. The system may include driving electronics by the control/monitoring equipment 180 for the LED and photo-transistor sensor, and may further provide an alarm component by the control module 172 if detection of the pH determines that the pH is outside the desired range. Additionally, since the settling time of the color detection is fast (sub second), it may be possible to insert this sensor in a feedback loop to regulate the pH of the media via modulation of the carbon dioxide content in a gaseous environment around the media. Alternatively, the control module 172 or control/monitoring equipment 180 may further provide components to modulate the pH of the incoming fluidic medium to correct the pH back to the desired range, by addition of buffers, and/or acidic or basic media components.

In some embodiments, the sensor 610 is connected to the fluidic medium inlet tubing 606, proximal to the at least one inlet 124 of the microfluidic device. Tubing 606 may be transparent, substantially transparent or translucent. LED 614 illuminates the tubing 606 and the stained fluidic medium 202a' within the tubing 606. The integrated colorimeter sensor 612 may monitor the pH of the incoming fluidic medium; ascertain that the pH has a value in a desired range for a particular culturing experiment; and alarm if the pH is out of the desired range.

In some embodiments, the sensor 610' is connected to the fluidic medium outlet tubing 608, proximal to the at least one outlet 124' of the microfluidic device. Tubing 608 may be transparent, substantially transparent or translucent. LED 614' illuminates the tubing 608 and the stained outflow fluidic medium 202a" within the tubing 608. The integrated colorimeter sensor 612' may monitor the pH of the incoming fluidic medium; ascertain that the pH has a value in a desired range for a particular culturing experiment; and alarm if the pH is out of the desired range.

Cells.

A cell capable of use in the system and methods of the invention may be any type of cell. For example, the cell may be an embryo, oocyte, or sperm, stem cell, progenitor cell, or a cell dissociated from a tissue, a blood cell, a hybridoma, a cultured cell, a cell from a cell line, a cancer cell, an infected cell, a transfected and/or transformed cell (line (including, but not limited to Chinese hamster ovarian (CHO) cells), a reporter cell, or the like. The cell may be a mammalian cell or the cell may be non-mammalian. The cell may include a bacterium, a fungus, a protozoa, or a mammalian cell infected with a parasitic species (e.g., *Leishmania* or *Plasmodium falciparum*). In some embodiments, the mammalian cell may be human, murine, porcine, or any other mammal of interest.

In some embodiments, the cell may be from a population of cells actively growing in culture or obtained from a fresh tissue sample (e.g., by dissociation of a solid tissue sample, such as a biopsy or fine needle aspirate), blood, saliva, urine, or other bodily fluid. Alternatively, the one or more biological cells can be from a culture of other sample that was previously frozen.

In some embodiments, the one or more biological cells may include one or more hybridoma cells. In other embodiments, the one or more biological cells may include one or more lymphocytes or leukocyte cells. In some embodiments, the cell is a B cell, a T cell, a NK cell, a dendritic cell, a macrophage, or other immunological cell type, or a precursor thereof, such as a progenitor cell or a hematopoietic stem cell.

In various embodiments, the one or more biological cells is one or more adherent cells. When one or more adherent cells are introduced to the microfluidic device, additional conditioning treatments may be provided to provide adherent cells with the appropriate soluble or nonsoluble environmental factors (e.g., one or more extracellular matrix components) permitting continued viability and/or cell multiplication.

Depending on the particular goal of the experiment, only one cell or a plurality of cells may be introduced into the microfluidic device for culturing and/or cloning. When only one cell is introduced into a growth chamber of the system and incubated according to the methods described herein, the resulting expanded population is a clonal colony of the cell originally introduced into the growth chamber.

Methods.

A method is provided for culturing at least one biological cell in a system including a microfluidic device having at least one growth chamber and a flow region. Culturing a cell (or cells) in a growth chamber of a microfluidic device also having a flow region can allow specific introduction of nutrients, growth factors or other cell signaling species at selected periods of time to achieve control of cell growth, viability, or portability parameters. The at least one biological cell is introduced into the at least one growth chamber having at least one conditioned surface where the conditioned surface supports cell growth, viability, portability, or any combination thereof. In some embodiments, the conditioned surface supports cell portability within the microfluidic device. In some embodiments, portability includes preventing adhesion of cells to the microfluidic device. In other embodiments, portability includes providing adherent cells with a conditioned surface that will support cell growth, viability, portability, or any combination thereof, while also allowing the cells to be moved after a period of culture within the microfluidic device. The at least one conditioned surface may be any conditioned surface as described herein. The introduction of the at least one biological cell may be accomplished using a number of different motive forces, as described herein, some of which may permit precise control in placing a specific biological cell into a specific location on the microfluidic device, for example, into a preselected growth chamber. The precise control of cell placement/removal and of nutrient/signaling/ environmental stimuli made possible by the methods described herein is difficult or impossible to achieve with macroscale culturing or other microfluidic culturing methods.

After placement, the at least one biological cell is then incubated for a period of time at least long enough to expand the at least one biological cell to produce a colony of biological cells. When biological cells are introduced into separate growth chambers, the resulting expanded colonies can be precisely identified for further use as separable groups of biological cells. When only one biological cell is introduced to a growth chamber and allowed to expand, the resulting colony is a clonal population of biological cells. Any appropriate cell may be used in the methods, including but not limited to the cells as described above.

The microfluidic device may be any of microfluidic devices 100, 300, 400, 500A-E, or 600 as described herein, and the microfluidic device may be part of a system having any of the components as described herein. The at least one growth chamber may include a plurality of growth chambers, and any suitable number of growth chambers as discussed herein may be used. In some embodiments of the methods, the microfluidic device may have about 500 to about 1500 growth chambers, about 1000 to about 2000 growth chambers, about 1000 to about 3500 growth chambers, about 2000 to about 5000 growth chambers, about 3000 to about 7000 growth chambers, about 5000 to about 10000 growth chambers, about 7500 to about 15000 growth chambers, about 10000 to about 17500 growth chambers, or about 12500 to about 20000 growth chambers.

In the methods of culturing one or more biological cells, the at least one conditioned surface may be any conditioned surface as described herein. The conditioned surface may be covalently linked to the microfluidic device. In some embodiments, the conditioned surface may include a linking group covalently linked to the surface, and the linking group may also be linked to a moiety configured to support cell growth, viability, portability, or any combination thereof, of the one or more biological cells within the microfluidic device. In some embodiments, a microfluidic device having a conditioned surface may be provided prior to importation of the one or more biological cells.

Introducing at Least One Biological Cell.

In some embodiments, introducing the at least one biological cell into the at least one growth chamber may include using a dielectrophoresis (DEP) force having sufficient strength to move the at least one biological cell. The DEP force may be produced using electronic tweezers, such as optoelectronic tweezers (OET). In some other embodiments, introducing one or more biological cells into the at least one growth chamber may include using fluid flow and/or gravity (e.g., by tilting the microfluidic device such that the cell(s) drop into a growth chamber located beneath the cell(s)).

In some embodiments, the at least one biological cell is introduced into the microfluidic device through an inlet port 124 into a flow region (e.g., flow channel) of the microfluidic device. The flow of medium in the flow channel can carry the cell to a location proximal to an opening to a growth chamber. After being position proximal to an opening to a growth chamber, the biological cell may then be moved in to the growth chamber using any of the motive forces described herein, including dielectrophoresis or gravity. Dielectrophoresis forces can include electrically actuated or optically actuated forces, and the DEP forces may further be provided by optoelectronic tweezers (OET). The at least one biological cell may be moved through the flow channel to the proximal opening of a connection region of at least one growth chamber, where the connection region opens directly to and is fluidically connected to the flow channel/region. The connection region of the at least one growth chamber is also fluidically connected to an isolation region of the at least one growth chamber. The at least one biological cell may further be moved through the connection region and into the isolation region of the at least one growth chamber. The isolation region of the at least one growth chamber may have dimensions sufficient to support cell expansion. Typically, however the dimensions of the growth chamber will limit such expansion to no more than about $1 \times 10^3$, $5 \times 10^2$, $4 \times 10^2$, $3 \times 10^2$, $2 \times 10^2$, $1 \times 10^2$, 50, 25, 15, or even as few as 10 cells in culture. In some embodiments, the isolation region may have dimensions sufficient to support cell expansion to no more than about $1 \times 10^2$, 50, 25, 15, or 10 cells in culture. It has been surprisingly found that cell incubation and/or expansion up to about $1 \times 10^2$ cells may be successfully performed in an isolation region having a volume of no more than about $1.0 \times 10^7$ cubic microns, $6 \times 10^6$ cubic microns, $2 \times 10^6$ cubicmicrons, $1.5 \times 10^6$ cubic microns, or $1.0 \times 10^6$ cubic microns. In some other embodiments, cell incubation and/or expansion up to about $1 \times 10^2$ cells may be successfully performed in an isolation region having a volume of no more than about $4 \times 10^5$ cubic microns. Depending on the cell type, the size of the biological cell may vary greatly, from bacteria having a diameter of about 1 micron and a volume of about 1 cubic microns$^3$, a small human cell such as a red blood cell having a diameter of about 7-8 microns and a volume of about 100 cubic microns, an immortalized cell line such as HeLa having a diameter of about 40 microns (non-confluent) and a volume of about 2000 cubic microns a megakaryocyte cell having a diameter of about 25 microns up to about 60 micron and a volume of about 4700 cubic microns to about 100,000 cubic microns, or a human oocyte having a diameter of about 120 microns and a volume of about 900,000 cubic microns. Accordingly, a growth chamber having a volume of about $4 \times 10^5$ cubic microns may permit expansion of very few megakaryocyte cells of the larger variety (volume of about $1 \times 10^5$ cubic microns), e.g., up to less than 5 cells total. Alternatively, the same small growth chamber (volume of about $4 \times 10^5$ cubic microns) may permit expansion of bacterial cells (volume of about 1 cubic microns) up to about 400,000 bacterial cells.

The method may further include introducing a first fluidic medium into a microfluidic channel of the flow region of the microfluidic device. In some embodiments, introduction of the first fluidic medium is performed prior to introducing the at least one biological cell. When the first fluidic medium is introduced before introducing the at least one biological cell, a flow rate may be selected such that the first fluidic medium is flowed into the growth chamber from the flow channel of the microfluidic device, e.g. at any suitable rate. Alternatively, if the microfluidic device has been primed with a medium containing an excess of one or more conditioning reagents, the first fluidic medium is flowed into the microfluidic channel at a rate such that the first fluidic medium replaces any remaining medium containing excess conditioning reagent(s) in the flow region.

When the flow of the first fluidic medium is introduced after introduction of the at least one biological cell to the growth chamber, the flow rate of the first fluidic medium may be selected to not sweep the isolation region which will not displace the at least one biological cell from the isolation region. The fluidic medium surrounding the at least one biological cell in the isolation region of the at least one growth chamber is the second fluidic medium, which may be the same or different from the first fluidic medium. In some embodiments, the second fluidic medium may be the same as the first fluidic medium, but during the incubating step, cellular waste products and depleted medium components may render the second fluidic medium different from the first fluidic medium.

Incubating the Cell.

In the methods described herein, the at least one biological cell is incubated for a period of time at least long enough to expand the cell to produce a colony of biological cells. That period of time may be selected to be from about 1 day to about 10 days. In other embodiments, the incubation period may be extended beyond 10 days and may continue for any desired period. Since the cells in the isolation region of the growth chamber are provided with nutrients and have waste removed by perfusion of fluidic medium, cells may be grown indefinitely. As the isolation region fills with the expanded cell population, any additional expansion will result in expanded biological cells inhabiting the connection region of the growth chamber, which is a swept region of the growth chamber. The perfused medium may sweep expanded biological cells out of the connection region of the growth chamber and subsequently out of the microfluidic device. Accordingly, the number of cells present in the isolation region of the growth chamber may be stabilized at a maximum number dependent on the size of the biological cell and size of the isolation region of the growth chamber. The ability to stabilize the maximal number of cells in an isolated population of cells provides an advantage over other currently available methods for cell culturing, as tedious cell population splitting can be eliminated.

In some embodiments, incubating may be carried out for about 1, 2, 3, 4, 5, 6, 7, 8, 9, 10 days, or more. Incubating periods may range from about 1 day to about 6 days, from about 1 day to about 5 days, from about 1 day to about 4 days, from about 1 day to about 3 days, or from about 1 day to about 2 days. In other embodiments incubating may be carried out for less than about 5 days, less than about 4 days, less than about 3 days, or less than about 2 days. In some embodiments, incubating may be carried out for less than about 3 days or less than about 2 days. In other embodiments, incubating may be carried out for about 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, or about 23 h.

During the culturing step, an image of the at least one growth chamber and any cells contained therein may be monitored at one or more time points throughout the culturing step. The image may be stored in the memory of a processing component of the system.

Perfusing the Cell.

During the incubating step, the second fluidic medium, present within the isolation region of the growth chamber may become depleted of nutrients, growth factors or other growth stimulants. The second fluidic medium may accumulate cellular waste products. Additionally, as the at least one biological cell continues to grow during the period of incubation, it may be desirable to alter the nutrients, growth factors or other growth stimulants to be different from those of the first or second media at the start of the incubation. Culturing in a growth chamber of a microfluidic device as described here may afford the specific and selective ability to introduce and alter chemical gradients sensed by the at least one biological cell, which may much more closely approximate in-vivo conditions. Alternatively, altering the chemical gradients sensed by the at least one biological cell to purposely non-optimized set of conditions may permit cell expansion under conditions designed to explore disease or treatment pathways. The method may therefore include perfusing the first fluidic medium during the incubating step, wherein the first fluidic medium is introduced via at least one inlet 124 of the microfluidic device and wherein the first fluidic medium, optionally comprising components from the second fluidic medium is exported via at least one outlet of the microfluidic device.

Exchange of components of the first fluidic medium, thereby providing fresh nutrients, soluble growth factors, and the like, and/or exchange of waste components of the medium surrounding the cell(s) within the isolation region occurs at the interface of the swept and unswept regions of the growth chamber substantially under conditions of diffusion. Effective exchange has been surprisingly found to result under substantially no flow conditions. Accordingly, it has been surprisingly found that successful incubation does not require constant perfusion. As result, perfusing may be non-continuous. In some embodiments, perfusing is periodic, and in some embodiments, perfusing is irregular. Breaks between periods of perfusion may be of sufficient duration to permit components of the second fluidic medium in the isolation region to diffuse into the first fluidic medium in the flow channel/region and/or components of the first fluidic medium to diffuse into the second fluidic medium, all without substantial flow of the first medium into the isolation region.

In another embodiment, low perfusion rates may also be employed to obtain effective exchange of the components of fluidic media within and outside of the unswept region of the growth chamber.

Accordingly, one method of perfusing at least one biological cell in at least one growth chamber of a microfluidic device is shown in FIG. 7 and includes a perfusing step 7002 where the first fluidic medium is flowed into a flow region fluidic ally connected to the growth chamber at a first perfusion rate $R_1$ for a first perfusion time $D_1$ through a flow region of the microfluidic device. $R_1$ may be selected to be a non-sweeping rate of flow, as described herein. Method 700 further includes the step 7004 of stopping the flow of the fluidic medium for a first perfusion stop time $S_1$. Steps 7002 and 7004 are repeated for W repetitions, where W may be an integer selected from 1 to about 1000, whereupon the perfusion process 700 is complete. In some embodiments, W may be an integer of 2 to about 1000.

Another method 800, of perfusing at least one biological cell in at least one growth chamber of a microfluidic device is shown in FIG. 8, which includes a first perfusion cycle that includes the step 8002 of flowing the fluidic medium into a flow region fluidically connected to the growth chamber at a first perfusion rate $R_1$ for a first perfusion time $D_1$ through a flow region of the microfluidic device. $R_1$ may be selected to be a non-sweeping rate of flow, as described herein. The first perfusion cycle includes the step 8004 of stopping the flow of the fluidic medium for a first perfusion stop time $S_1$. The first perfusion cycle may be repeated for W repetitions, wherein W is an integer selected from 1 to about 1000. After the Wth repeat of the first perfusion cycle is completed, method 800 further includes a second perfusion cycle, which includes the step 8006 of flowing the first fluidic medium at a second perfusion rate $R_2$ for a second perfusion time $D_2$, wherein $R_2$ is selected to be a non-sweeping rate of flow. The second perfusion cycle of Method 800 further includes the step 8008 of stopping the flow of the fluidic medium for a second perfusion stop time $S_2$. Thereafter, the method returns to step 8002 and 8004 of the first perfusion cycle and the combined two cycle perfusion process is repeated for V repeats, wherein V is an integer of 1 to about 5000. The combination of W and V may be chosen to meet the desired incubation period endpoint.

In various embodiments of method 700, or 800, perfusing rate $R_1$ may be any non-sweeping rate of flow of fluidic medium as described above for flow controller configurations. In some embodiments, $R_1$ may be about 0.009, 0.010, 0.020, 0.030, 0.040, 0.05, 0.06, 0.07, 0.08, 0.09, 0.10, 0.11, 0.12, 0.13, 0.14, 0.15, 0.16, 0.17, 0.18, 0.19, 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, 2.00. 2.10, 2.20, 2.40, 2.50, 2.60, 2.70, 2.80, 2.90 or 3.00 microliters/sec.

In various embodiments of method 800, the second perfusion rate $R_2$ may be any non-sweeping rate of flow of fluidic medium as described as above for flow controller configurations. In some embodiments, the $R_2$ may be 0.009, 0.010, 0.020, 0.030, 0.040, 0.05, 0.06, 0.07, 0.08, 0.09, 0.10, 0.11, 0.12, 0.13, 0.14, 0.15, 0.16, 0.17, 0.18, 0.19, 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, 2.00. 2.10, 2.20, 2.40, 2.50, 2.60, 2.70, 2.80, 2.90 or 3.00 microliters/sec. The flow rates $R_1$ and/or $R_2$ may be chosen in any combination. Typically, perfusion rate $R_2$ may be greater than perfusion rate $R_1$, and may be about 5×, 10×, 20×, 30×, 40×, 50×, 60×, 70×, 80×, 90×, 100×, or more than R. In some embodiments, $R_2$ is at least ten times faster than $R_1$. In other embodiments, $R_2$ is at least twenty times faster than $R_1$. In yet another embodiment, $R_2$ is at least 100× the rate of $R_1$.

In various embodiments of method 700 or 800, first perfusion time $D_1$ may be any suitable duration of perfusion as described above for flow controller configurations. In various embodiments, $D_1$ may be about 5, 10, 15, 20, 25, 30, 35, 40, 45, 50, 55, 60, 65, 70, 80, 90, 100, 110, 120, 130, 140, 150, 160, 170 or 180 sec. In other embodiments, $D_1$ may be a range of time, e.g., about 10 to about 40 sec, as described above. In some embodiments, $D_1$ may be about 30 sec to about 75 sec. In other embodiments, $D_1$ may be about 100 sec. In other embodiments, $D_1$ may be in a range from about 60 sec to about 150 sec. In yet other embodiments, $D_1$ may be about 20 min, 30 min, 40 min, 50 min, 60 min, 80 min, 90 min, 110 min, 120 min, 140 min, 160 min, 180 min, 200 min, 220 min, 240 min, 250 min, 260 min, 270 min, 290 min or 300 min. In some embodiments, $D_1$ is about 40 min to about 180 min.

In various embodiments of method 700 or 800, second perfusion time $D_2$ may be any suitable duration of perfusion as described above for flow controller configurations. In various embodiments, $D_2$ may be about 5 sec, 10 sec, 15 sec, 20 sec, 25 sec, 30 sec, 35 sec, 40 sec, 45 sec, 50 sec, 55 sec, 60 sec, 65 sec, 70 sec, 80 sec, 90 sec or about 100 sec. In other embodiments, $D_2$ may be a range of time, e.g., about 5 sec to about 20 sec, as described above. In other embodiments, $D_2$ may be about 30 sec to about 70 sec. In other embodiments, $D_2$ may be about 60 sec.

In various embodiments of method 700 or 800, the first perfusion time $D_1$ may be the same or different from the second perfusion time $D_2$. $D_1$ and $D_2$ may be chosen in any combination. In some embodiments, the duration of perfusing $D_1$ and/or $D_2$ may be selected to be shorter than the stopping periods $S_1$ and/or $S_2$.

In various embodiments of method 700 or 800, the first perfusion stop time $S_1$ may be selected to be any suitable period of time as described above for an interval of time between periods of perfusion for flow controller configurations. In some embodiments, $S_1$ may be about 0 min, 5 min, about 10 min, about 15 min, about 20 min, about 25 min, about 30 min, about 35 min, about 40 min, about 45 min, about 60 min, about 65 min, about 80 min, about 90 min, about 100 min, about 120 min, about 150 min, about 180 min, about 210 min, about 240 min, about 270 min, or about 300 min. In various embodiments, $S_1$ may be any appropriate range of time, as described above for flow controller configuration intervals between perfusion, e.g. about 20 to about 60 min. In some embodiments, $S_1$ may be about 10 min to about 30 min. In other embodiments, $S_1$ may be about 15 min. In yet other embodiments, $S_1$ may be about 0 sec, 5 sec, 10 sec, 20 sec, 30 sec, 40 sec, 50 sec, 60 sec, 70 sec, 80 sec, or about 90 sec. In some embodiments, $S_1$ is about 0 sec.

In various embodiments of method 700 or 800, the second perfusion stop time $S_2$ may be selected to be any suitable period of time as described above for an interval of time between periods of perfusion for flow controller configurations. In some embodiments, $S_2$ may be about 0 min, 5 min, about 6 min, about 7 min, about 8 min, about 9 min, about 10 min, about 20 min, about 30 min, about 45 min, about 50 min, about 60 about 90 min, about 120 min, about 180 min, about 240 min, about 270 min, or about 300 min. In various embodiments, $S_2$ may be any appropriate range of time, as described above for flow controller configuration intervals between perfusion, e.g. about 15 to about 45 min. In some embodiments, $S_2$ may be about 10 min to about 30 min. In other embodiments, $S_2$ may be about 8 min or 9 min. In other embodiments, $S_2$ is about 0 min.

In various embodiments of method 700 or 800, the first perfusion stop time $S_1$ and the second perfusion stop time $S_2$ may be selected independently from any suitable value. S may be the same or different from $S_2$.

In various embodiments of method 800, the number of W repetitions may be selected to be the same or different from the number of V repetitions.

In various embodiments of methods 700 or 800, W may be about 1, about 4, about 5, about 6, about 8, about 10, about 12, about 15, about 18, about 20, about 24, about 30, about 36, about 40, about 45, or about 50. In some embodiments, W may be selected to be about 1 to about 20. In some embodiments, W may be 1.

In various embodiments of method 800, V may be about 5, about 10, about 20, about 25, about 30, about 35, about 40, about 50, about 60, about 80, about 100, about 120, about 240, about 300, about 350, about 400, about 450, about 500, about 600, about 750, about 900, or about 1000. In some embodiments, V may be selected to be about 10 to about 120. In other embodiments, V may be about 5 to about 24. In some embodiments, V may be about 30 to about 50 or may be about 400 to about 500.

In various embodiments of method 800, the number of W repetitions may be selected to be the same or different from the number of V repetitions.

In various embodiments of methods 700 or 800 a total time for the first step of perfusing (represented by steps 7002/7004 or 8002/8004) is about 1 h to about 10 h and W is an integer is 1. In various embodiments, the total time for the first step of perfusing is about 9 min to about 15 min.

In various embodiments of method 800, a total time for the second step of a perfusing cycle (represented by step 8006/8008) is about 1 min to about 15 min or about 1 min to about 20 min.

In any of methods 700 or 800, the perfusing method may be continued for the entire incubation period of the biological cell, e.g., for about 1, about 2, about 3, about 4, about 5, about 6, about 7, about 8 about 9, about 10 days or more.

In another non-limiting embodiment of method 800 of FIG. 8, the controller may be configured to perfuse the fluidic medium(s) in the flow region having longer periods of perfusion $D_1$ during the perfusing step 8002. The controller may perfuse the fluidic medium at a first rate for a period of about 45 min, about 60 min, about 75 min, about 90 min, about 105 min, about 120 min, about 2.25 h, about 2.5 h, about 2.45 h, about 3.0 h, about 3.25 h, about 3.5 h, about 3.75 h, about 4.0 h, about 4.25 h, about 4.5 h, about 4.75 h, about 5 h, or about 6 h. At the end of the first perfusion period $D_1$, the flow of the fluidic medium may be stopped for a stopping period of time $S_1$, which may be about 0 sec, 15 sec, 30 sec, about 45 sec, about 1 min, about 1.25 min, about 1.5 min, about 2.0 min, about 3.0 min, about 4 min, about 5 min or about 6 min. In some embodiments, the first flow rate $R_1$ may be selected to be about 0.009, 0.01, 0.02, 0.03, 0.05, 0.1, 0.2, 0.3, 0.4, or about 0.5 microliters/sec. The flow of the fluidic medium may be stopped for a perfusion stopping period $S_1$ of less than about 1 minute or S may be 0 sec. Alternatively, $S_1$ may be about 30 sec, about 1.5 min, about 2.0 min, about 2.5 min, or about 3 min. A second perfusion period $D_2$ may follow, using a different perfusion rate. In some embodiments, the second perfusion rate may be higher than the first perfusion rate. In some embodiments, the second perfusion rate $R_2$ may be selected from about 1.0, 1.1, 1.2, 1.3, 1.4, 1.5, 1.7, 1.9, 2.0, 2.2, 2.4, 2.6, 2.8, 3.0, 3.2, 3.4, 3.6, 3.8, 4.0, 4.2, 4.4, 4.6, 4.8, 5.0, 6.0, 7.0, 8.0 or about 9.0 microliters/sec. The second perfusion period $D_2$ may be about 1 sec, about 2 sec, about 3 sec, about 4 sec, about 5 sec, about 6 sec, about 10 sec, about 15 sec, about 30 sec, about 45 sec, about 60 sec, about 65 sec, about 75 sec, about 80 sec, or about 90 sec. Perfusing may be then stopped for a second perfusion stop period $S_2$, which may be about 0 sec, 10 sec, about 20 sec, about 30 sec, about 40 sec, about 50 sec, about 60 sec, about 1.5 min, about 1.75 min, about 2.0 min, about 2.5 min, about 2.75 min, about 3.0 min or about 4.0 min. In some embodiments, $D_1$ may be about 2 h, about 3 h, or about 4 h. In various embodiments, $D_1$ may be about 4 h. In various embodiments, $S_1$ may be 0 sec or less than about one minute. The second perfusion period $D_2$ may be about 1 sec to about 6 sec. In some embodiments, the second perfusion stop period $S_2$ may be about 40 sec to about 1.5 min.

Accordingly, a method is provided for perfusing at least one biological cell in at least one growth chamber of a microfluidic device including the steps of: perfusing the at least one biological cell using a first perfusion step including: flowing a first fluidic medium at a first perfusion rate $R_1$ for a first perfusion time $D_1$ through a flow region of the microfluidic device, where the flow region is fluidically connected to the growth chamber, wherein $R_1$ is selected to be a non-sweeping rate of flow; stopping the flow of the first fluidic medium for a first perfusion stop time $S_1$; and repeating the first perfusion step for W repetitions, where W is an integer selected from 1 to 1000. The method may further include a step of perfusing the at least one biological cell using a second perfusion step comprising: flowing the first fluidic medium at a second perfusion rate $R_2$ for a second perfusion time $D_2$, where $R_2$ is selected to be a non-sweeping rate of flow; stopping the flow of the first fluidic medium for a second perfusion stop time $S_2$; and repeating the first perfusion step followed by the second perfusion step for V repetitions, wherein V is an integer of 1 to 1000.

The second perfusion rate $R_2$ may be greater than the first perfusion rate $R_1$. The first perfusion time $D_1$ may be the same or different from the second perfusion time $D_2$. The first perfusion stop time $S_1$ may be the same or different from the second perfusion stop time $S_2$. The number of W repetitions may be the same or different from the number of V repetitions, when the second perfusing step is performed. $R_2$ may be at least ten times faster than $R_1$. Alternatively, $R_2$ may be at least twenty times faster than $R_1$. $R_2$ may be at least 100 times as fast as $R_1$. $D_1$ may be about 30 sec to about 75 sec. In other embodiments, $D_1$ may be about 40 min to about 180 min or about 180 min to about 300 min. In some other embodiments, $D_1$ may be about 60 sec to about 150 sec. $S_1$ may be about 10 min to about 30 min. In other embodiments, $S_1$ may be about 5 min to about 10 min. In yet other embodiments, $S_1$ may be zero. In some embodiments, $D_1$ may be about 40 min to about 180 min, and $S_1$ may be zero. In other embodiments, $D_1$ may be about 60 sec to about 150 sec, and $S_1$ may be about 5 min to about 10 min. In yet other embodiments, $D_1$ may be about 180 min to about 300 min, and $S_1$ may be zero. The total time for the first perfusing step may be about 1 h to about 10 h. In other embodiments, the total time for the first perfusing step may be about 2 h to about 4 h. In some embodiments, W may be an integer greater than 2. In some embodiments, W may be about 1 to about 20. In some embodiments, $D_2$ may be about 10 sec to about 25 sec. In other embodiments, $D_2$ may be about 10 sec to about 90 sec. In some embodiments, $S_2$ may be about 10 min to about 30 min. In other embodiments, $S_2$ may be about 15 min. In some embodiments, V may be about 10 to about 120. In some embodiments, V may be about 30 to about 50 or may be about 400 to about 500. In some embodiments, $D_2$ may be about 1 sec to about 6 sec. and $S_2$ may be 0 sec. In some embodiments, $D_2$ may be about 10 sec to about 90 sec and $S_2$ may be about 40 sec to about 1.5 min. In some embodiments, a total time for one repeat of the second perfusing step may be about 1 min to about 15 min.

Conditioning the Medium.

In order to provide a medium (e.g., first or second medium) that sustains and enhances growth and/or viability for the at least one biological cell, the first fluidic medium may contain both liquid and gaseous components (e.g., the gaseous components may be dissolved in the liquid components). In addition, the fluidic medium can include other components, such as biological molecules, vitamins and minerals that are dissolved in the liquid components. Any suitable components may be used in the fluidic media, as is known to one of skill. Some non-limiting examples are discussed above, but many other media compositions may be used without departing from the methods described herein. The media may or may not contain animal source sera. In some embodiments, the fluidic medium may include a chemically defined medium (at least prior to contacting cells or a cell-containing fluid), and may further be a protein-free or peptide-free chemically defined medium. In some embodiments, the fluidic medium may include a reduced serum medium.

The first fluidic medium may be prepared by saturating an initial fluidic medium with dissolved gaseous molecules, prior to introducing the first fluidic medium into the microfluidic device. Additionally, saturating the initial fluidic medium with dissolved gaseous molecules may continue right up to the point in time that the first fluidic medium is introduced into the microfluidic device. Saturating the initial fluidic medium may include contacting the microfluidic device with a gaseous environment capable of saturating the initial fluidic medium with dissolved gaseous molecules. Gaseous molecules that may saturate the initial fluidic medium include but are not limited to oxygen, carbon dioxide and nitrogen.

The first fluidic medium may further include moderating a pH of the first fluidic medium. Moderating the pH of the first fluidic medium can occur, for example, prior to and/or during introduction of dissolved gaseous molecules. Such moderating may be accomplished by the addition of a buffer species. One non-limiting example of a suitable buffering species is HEPES. Other buffering species may be present in the medium and may or may not depend on the presence of carbon dioxide (such as carbonic acid buffer systems), and can be selected by one of skill. Salts, proteins, carbohydrates, lipids, vitamin and other small molecules necessary for cell growth may also form part of the first fluidic medium composition.

In some embodiments, saturating of the first fluidic medium with the gaseous components may be performed in a reservoir prior to introduction via the inlet port. In other embodiments, saturating of the first fluidic medium with the gaseous components may be performed in a gas permeable connecting conduit between the reservoir and the inlet. In yet other embodiments, saturating of the first fluidic medium with the gaseous components may be performed via a gas permeable portion of a lid of the microfluidic device. In some embodiments, the gaseous saturation of the fluidic medium also includes maintaining humidity in the gas exchange environment such that the fluidic medium within the microfluidic device does not change in osmolality during the incubation period.

The composition of the first fluidic medium may also include at least one secreted component from a feeder cell culture. Secreted feeder cell components may include growth factors, hormones, cytokines, small molecules, proteoglycans, and the like. The introduction of the at least one secreted component from the feeder cell culture may be performed in the same reservoir where saturating the first fluidic medium with gaseous components is performed, or introduction of the at least one secreted component from the feeder cell culture to the first fluidic medium may be made prior to the saturating step.

In some other embodiments, the composition of the first medium may also include an additive(s) designed to provide altered fluidic medium to test the response of the cell to the additive(s). Such additive(s) can, for example, increase or decrease cell viability or growth.

In some embodiments, the method may include detecting the pH of the first fluidic medium as it is introduced via the at least one inlet. Detecting the pH may be performed at a location directly proximal to the inlet. In some embodiments, the method may include detecting the pH of the first fluidic medium as the first fluidic medium is exported via an outlet. Detecting the pH may be performed at a location directly proximal to the outlet. Either or both of the detectors used to detect the pH may be an optical sensor. In some embodiments, the detector may be capable of providing an alarm if the pH deviates from an acceptable range. In some other embodiments, when a pH value measured by the detector deviates from an acceptable range, then the composition of the first fluidic medium may be altered.

During the incubating step, an image of the at least one growth chamber and any cells contained therein may be monitored.

Exporting the at Least One Biological Cell.

After the incubating step is complete, the at least one biological cell or colony of cells may be exported out of the growth chamber or the isolation region thereof. Exporting may include using a dielectrophoresis (DEP) force sufficiently strong to move the one or more biological cells/colony of cells. The DEP force may be optically actuated or electronically actuated. For example, the microfluidic device can include a substrate having a DEP configuration, such as an opto-electronic tweezer (OET) configuration. In other embodiments, the at least one biological cell or colony of cells may be exported out of the growth chamber or the isolation region using fluid flow and/or gravity. In yet other embodiments, the at least one biological cell or colony of cells may be exported out of the growth chamber or the isolation region using compressive force on a deformable lid region above the growth chamber or the isolation region thereof, thereby causing a localized flow of fluid out of the growth chamber or isolation region.

After the at least one biological cell or colony of cells is exported out of the growth chamber or the isolation region, then the cells may be exported from the flow region (e.g., channel) out of the microfluidic device. In some embodiments, exporting the cells from the flow region includes using a DEP force sufficiently strong to move the one or more biological cells/colony of cells. The DEP force may be generated as described above. In some other embodiments, exporting the cells from the flow region out of the microfluidic device includes using fluid flow and/or gravity to move the cells.

During the exporting step, an image of the at least one growth chamber and any cells contained therein may be monitored.

Conditioning at Least One Surface.

In some embodiments, the microfluidic device is provided with at least one surface of the at least one growth chamber in a conditioned state. In other embodiments, the surface of the at least one growth chamber is conditioned prior to introducing the at least one biological cell and may be performed as part of the method of culturing the one or more biological cells. Conditioning the surface may include treating the surface with a conditioning reagent, such as a polymer.

In some embodiments, a method is provided for treating at least one surface of at least one growth chamber of a microfluidic device (100, 300, 400, 500A-E, and 600), including the steps of flowing the fluidic medium including an excess of conditioning reagent into the flow channel (FIGS. 1A-1C, 2, 3, 4A-C); incubating the microfluidic device for a selected period of time; and replacing the medium in the channel. In other embodiments, a method for priming a microfluidic device includes the steps of flowing a priming solution containing a conditioning reagent into the flow channel; incubating the device for a selected period of time, thereby conditioning at least one surface of the growth chamber; and replacing the solution in the channel with a fluidic medium. The priming solution may contain any fluidic medium as described herein. The fluidic medium replacing the conditioning solution or the fluidic medium having an excess of conditioning reagent may be any medium as described herein and may additionally contain cells.

In some embodiments, the at least one surface may be treated with a polymeric conditioning reagent including alkylene ether moieties. The polymeric conditioning reagent having alkylene ether moieties may include any suitable alkylene ether containing polymers, including but not limited to any of the alkylene ether containing polymers discussed above. In one embodiment, the surface of the growth chamber may be treated with amphiphilic nonionic block copolymers which include blocks of polyethylene oxide (PEO) and polypropylene oxide (PPO) subunits in differing ratios and locations within the polymer chain (e.g., Pluronic® polymers). Specific Pluronic® polymers useful for yielding a conditioned surface include Pluronic® L44, L64, P85, F68 and F127 (including F127NF).

In other embodiments, the surface may be treated with a polymeric conditioning reagent including carboxylic moieties. Non-limiting examples of suitable carboxylic acid containing polymeric conditioning reagents are discussed above and any appropriate carboxylic acid containing polymeric conditioning reagent may be used to treat the surface.

In other embodiments, the surface may be treated with a polymeric conditioning reagent including saccharide moieties. Non-limiting examples of suitable saccharide containing polymeric conditioning reagents are discussed above and any appropriate saccharide containing polymeric conditioning reagent may be used to treat the surface.

In other embodiments, the surface may be treated with a polymeric conditioning reagent including sulfonic acid moieties. Non-limiting examples of suitable sulfonic acid containing polymeric conditioning reagents are discussed above and any appropriate sulfonic acid containing polymeric conditioning reagent may be used to treat the surface.

In other embodiments, the surface may be treated with a polymeric conditioning reagent including amino acid moieties. Non-limiting examples of suitable amino acid containing polymeric conditioning reagents are discussed above and any appropriate amino acid containing polymeric conditioning reagent may be used to treat the surface. The amino acid containing polymeric conditioning reagent may include a protein. In some embodiments, the surface is treated with a protein, wherein the protein may include a component found in or part of a mammalian serum. In other embodiments, the surface is treated with components of a mammalian serum. In some embodiments, the surface may be treated with a cell culture medium supplement, such as B-27® Supplement ((50×), serum free from ThermoFisher Scientific, Cat #17504044). The mammalian serum may be Fetal Bovine Serum (FBS). Alternatively, the mammalian serum may be Fetal Calf Serum (FCS).

In other embodiments, the surface may be treated with a polymeric conditioning reagent including nucleic acid moieties. Non-limiting examples of suitable nucleic acid containing polymeric conditioning reagents are discussed above and any appropriate nucleic acid containing polymeric conditioning reagent may be used to treat the surface.

In some embodiments, a mixture of more than one polymeric conditioning reagent may be used to treat the surface of the growth chamber.

In some other embodiments, the step of conditioning may include treating at least one surface of the at least one growth chamber with at least one cell adhesion blocking molecule. In some embodiments, the step of treating the at least one surface of the at least one growth chamber with at least one cell adhesion blocking molecule may be performed before exporting the cells from the microfluidic device. In some embodiments, the step of conditioning may include pre-incubating the cells with the at least one cell adhesion blocking molecule. In some embodiments, the at least one cell adhesion blocking molecule may act to disrupt actin filament formation. In some embodiments, the cell adhesion blocking molecule may be Cytochalasin B. In other embodiments, the at least one cell adhesion blocking molecule may block integrin receptors. In some embodiments, the cell adhesion blocking molecule may include a peptide containing an RGD motif. In some other embodiments, the at least one cell adhesion blocking molecule may reduce binding of cells to DNA fouled surfaces. The cell adhesion blocking molecule which may reduce binding of cells to DNA fouled surfaces may include a DNase 1 protein. In other embodiments, the at least one cell adhesion blocking molecule may include a small molecule fibronectin inhibitor. In yet other embodiments, the at least one cell adhesion blocking molecule may be an antibody, e.g., an anti B1 integrin antibody. In some embodiments, the at least one cell adhesion blocking molecule may include a combination of more than one type of cell adhesion blocking molecules.

In other embodiments, conditioning includes heating the surface of the growth chamber to a temperature of about 30° C. In some embodiments, the method includes heating the surface to a temperature of at least about 25° C., 26° C., 27° C., 28° C., 29° C., 30° C., 31° C., 32° C., 33° C., 34° C., 35° C., 36° C., 37° C., 38° C., 39° C., or about 40° C. In some embodiments, the method includes heating the surface to a temperature greater than about 25° C. In other embodiments the method includes heating the surface to a temperature in the range from about 30°-40° C.; about 35° C. to about 40° C.; or about 36° C. to about 38° C. In some embodiments, the method includes heating the surface to a temperature of at least about 30° C. In some embodiments, heating the surface includes at least one surface that is conditioned by treating the surface with a polymer.

Clonal Population.

The methods described here also include methods where only one biological cell is introduced to the at least one growth chamber. A method is provided for cloning a biological cell in a system including a microfluidic device having a flow region configured to contain a flow of a first fluidic medium; and at least one growth chamber including an isolation region and a connection region, the isolation region being fluidically connected with the connection region and the connection region including a proximal opening to the flow region, which includes the steps of introducing the biological cell into the at least one growth chamber, where the at least one growth chamber is configured to have at least one surface conditioned to support cell growth, viability, portability, or any combination thereof; and incubating the biological cell for a period of time at least long enough to expand the biological cell to produce a clonal population of biological cells. In some embodiments, the system may be any system as described herein. The microfluidic device may be any microfluidic device as described herein.

In some embodiments of the method for cloning a biological cell, the at least one conditioned surface may include a linking group covalently linked to the surface, and the linking group may be linked to a moiety configured to support cell growth, viability or portability of the one or more biological cells within the microfluidic device. In some embodiments, the linking group may include a siloxy linking group. In other embodiments, the linking group may include a phosphonate linking group. In some embodiments, the linking group may be indirectly linked to the moiety configured to support cell growth, viability, portability, or any combination thereof. In other embodiments, the linking group may be directly linked to the moiety configured to support cell growth, viability, portability, or any combination thereof. The linking group may be indirectly linked to the moiety configured to support cell growth, viability or movability via connection to a linker. In some embodiments, the linking group may be indirectly linked to the moiety configured to support cell growth, viability or movability via connection to a first end of a linker. In some embodiments, the linker may further include a linear portion wherein a backbone of the linear portion comprises 1 to 200 non-hydrogen atoms selected from any combination of silicon, carbon, nitrogen, oxygen, sulfur and phosphorus atoms. In some embodiments, the backbone of the linear portion may include one or more arylene moieties. In other embodiments, the linker may include a triazolylene moiety. In some embodiments, the triazolylene moiety may interrupt the linear portion of the linker or may be connected at a second end to the linear portion of the linker. In various embodiments, the moiety configured to support cell growth and/or viability and/or portability may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids. In some embodiments, the at least one conditioned surface comprises alkyl or perfluoroalkyl moieties. In other embodiments, the at least one conditioned surface comprises alkylene ether moieties or dextran moieties.

In various embodiments, the method may further include the step of conditioning the at least a surface of the at least one growth chamber. In some embodiments, conditioning includes treating the at least one surface with one or more agents that support cell portability within the microfluidic device. In some embodiments, the conditioning may include treating the at least a surface of the at least one growth chamber with a conditioning reagent including a polymer. In some embodiments, the polymer may include alkylene ether moieties. In some embodiments, the polymer may include carboxylic acid moieties. In some embodiments, the polymer may include saccharide moieties. In other embodiments, the polymer may include sulfonic acid moieties. In yet other embodiments, the polymer may include amino acid moieties. In further embodiments, the polymer may include nucleic acid moieties. In some embodiments, the conditioning may include treating the at least a surface of the at least one growth chamber with one or more components of mammalian serum. In some embodiments, the mammalian serum may be Fetal Bovine Serum (FBS), or Fetal Calf Serum (FCS). In various embodiments, conditioning may include treating at least one surface of the at least one growth chamber with at least one cell adhesion blocking molecule. In some embodiments, the at least one cell adhesion blocking molecule may include a RGD containing peptide. In other embodiments, the at least one cell adhesion blocking molecule may be Cytochalasin B, an antibody to an integrin, an inhibitor of fibronectin, or a DNase 1 protein. In various embodiments, conditioning may include treating at least one surface of the at least one growth chamber with a combination of more than one type of cell adhesion blocking molecules.

In various embodiments, the conditioning may include heating the at least a surface of the at least one growth chamber to a temperature of about 30° C.

In various embodiments, the method may further include a step of introducing a first fluidic medium into a microfluidic channel of the flow region of the microfluidic device. In some embodiments, introducing the first fluidic medium may be performed prior to introducing the biological cell. In some embodiments, introducing the biological cell into the at least one growth chamber may include using a dielectrophoresis (DEP) force having sufficient strength to move the biological cell. In some embodiments, the DEP force may be optically actuated. In some embodiments, the DEP force may be produced by optoelectronic tweezers (OET). In some other embodiments, introducing the biological cell into the at least one growth chamber may include using fluid flow and/or gravity.

In some embodiments, introducing the biological cell into the at least one growth chamber may further include introducing the biological cell into an isolation region of the at least one growth chamber. In some embodiments, the isolation region of the at least one growth chamber may have dimensions sufficient to support cell expansion to no more than $1\times10^2$ cells. In some embodiments, the isolation region may be at least substantially filled with a second fluidic medium. In some embodiments, the flow region may be fluidically connected to a proximal opening of a connection region of the at least one growth chamber, and further wherein the connection region may also be fluidically connected to the isolation region of the growth chamber.

In various embodiments, the method may further include a step of perfusing the first fluidic medium during the incubating step, wherein the first fluidic medium may be introduced via at least one inlet port of the microfluidic device and wherein the first fluidic medium, optionally comprising components from the second fluidic medium may be exported via at least one outlet of the microfluidic device. In some embodiments, perfusing may be non-continuous. In some other embodiments, perfusing may be periodic. In yet other embodiments, perfusing may be irregular. In some embodiments, perfusing of the first fluidic medium may be performed at a rate sufficient to permit components of the second fluidic medium in the isolation region diffuse into the first fluidic medium in the flow region and/or components of the first fluidic medium diffuse into the second fluidic medium in the isolation region; and the first medium may not substantially flow into the isolation region. In some embodiments, perfusing the first fluidic medium may be performed for a duration of about 45 sec to about 90 sec about every 10 min to about every 30 min. In some embodiments, perfusing the first fluidic medium may be performed for a duration of about 2 h to about 4 h. In some embodiments, the period of time that the at least one biological cell is incubated may be from about 1 day to about 10 days.

In some embodiments, a composition of the first fluidic medium may include liquid and gaseous components. In various embodiments, the method may further include a step of saturating the first fluidic medium with dissolved gaseous molecules prior to introducing the first fluidic medium into the microfluidic device. In various embodiments, the method may further include a step of contacting the microfluidic device with a gaseous environment capable of saturating the first fluidic medium or the second fluidic medium with dissolved gaseous molecules. In various embodiments, the method may further include a step of moderating a pH of the first fluidic medium upon introduction of dissolved gaseous molecules. In some embodiments, saturating the first fluidic medium with the gaseous components may be performed in a reservoir prior to introduction via the inlet port, in a gas permeable connector between the reservoir and the inlet port, or via a gas permeable portion of a lid of the microfluidic device. In some embodiments, a composition of the first fluidic medium may include at least one secreted component from a feeder cell culture.

In various embodiments, the method may further include a step of detecting the pH of the first fluidic medium as it is exported via the at least one outlet. In some embodiments, the detecting step may be performed at a location directly proximal to the at the least one outlet. In various embodiments, the method may further include a step of detecting the pH of the first fluidic medium as it is introduced via the at least one inlet port. In some embodiments, the sensor may be an optical sensor. In various embodiments, the method may further include a step of altering a composition of the first fluidic medium.

In various embodiments, the method may further include a step of monitoring an image of the at least one growth chamber and any cells contained therein.

In various embodiments, the biological cell may be a mammalian cell. In some embodiments, the biological cell may be an immunological cell. In some embodiments, the biological cell may be a lymphocyte or a leukocyte. In some embodiments, the biological cell may be a B cell, a T cell, a NK cell, macrophage, or dendritic cell. In some embodiments, the biological cell may be an adherent cell. In some embodiments, the biological cell may be a hybridoma cell.

In some embodiments, the biological cell may be a plurality of biological cells and the at least one growth chamber is a plurality of growth chambers. In various embodiments, the method may further include a step of moving no more than one of the plurality of biological cells into each of the plurality of growth chambers.

In some embodiments of the method of cloning a biological cell, the conditioned surface may further include a cleavable moiety. The method may include a step of cleaving the cleavable moiety before exporting one or more biological cells of the clonal population out of the growth chamber or the isolation region thereof.

In various embodiments, the method may further include a step of exporting one or more biological cells of the clonal population out of the growth chamber or the isolation region thereof. In some embodiments, exporting may include using a dielectrophoresis (DEP) force sufficiently strong to move the one or more biological cells. In some embodiments, the DEP force is optically actuated. In some embodiments, the DEP force may be produced by optoelectronic tweezers (OET). In some embodiments, exporting may include using fluid flow and/or gravity. In some embodiments, exporting may include using compressive force on a deformable lid region above the growth chamber or the isolation region thereof. In various embodiments, the method may further include a step of exporting one or more biological cells of the clonal population from the flow region out of the microfluidic device. In some embodiments, exporting may include using a DEP force sufficiently strong to move the one or more biological cells. In some embodiments, the DEP force is optically actuated. In some embodiments, the DEP force may be produced by optoelectronic tweezers (OET). In some embodiments, exporting may include using fluid flow and/or gravity.

Kits.

Kits may be provided for culturing a biological cell, where the kit includes: a microfluidic device having a flow region configured to contain a flow of a first fluidic medium and at least one growth chamber, and a surface conditioning reagent. In this embodiment, the at least one growth chamber has not been pre-treated to condition the at least one surface of the at least one growth chamber, and the conditioned surface is created by treating with the surface conditioning reagent before cell(s) are introduced. Other kits for culturing a biological cell are also provided, where the kit includes a microfluidic device having a flow region configured to contain a flow of a first fluidic medium; and at least one growth chamber comprising an isolation region and a connection region, wherein the isolation region is fluidically connected with the connection region and the connection region comprises a proximal opening to the flow region; and further wherein the at least one growth chamber comprises at least one surface conditioned to support cell growth, viability, portability, or any combination thereof. Yet other kits are provided for culturing a biological cell, including a microfluidic device including a flow region configured to contain a flow of a first fluidic medium; and at least one growth chamber including an isolation region and a connection region, wherein the isolation region is fluidically connected with the connection region and the connection region has a proximal opening to the flow region; where the at least one growth chamber has at least one surface having a surface modifying ligand. Alternatively, kits may be provided for culturing a biological cell, where the kit includes: a microfluidic device having a flow region configured to contain a flow of a first fluidic medium; and at least one growth chamber having at least one conditioned surface which can support cell growth, viability, portability, or any combination thereof; and a surface conditioning reagent. The microfluidic device of any of the kits may be any one of microfluidic devices 100, 200, 240, 290, 400, 500A-E, or 600 and have any of the features described above.

The microfluidic device of any of the kits may further include a microfluidic channel including at least a portion of the flow region, and the device may further include a growth chamber having a connection region that opens directly into the microfluidic channel. The growth chamber may further include an isolation region. The isolation region may be fluidically connected to the connection region and may be configured to contain a second fluidic medium, where when the flow region and the at least one growth chamber are substantially filled with a first and second fluidic media respectively, then components of the second fluidic medium diffuse into the first fluidic medium and/or components of the first fluidic medium diffuse into the second fluidic medium; and the first medium does not substantially flow into the isolation region.

In various embodiments of any of the kits, growth chambers may be configured like growth chambers 124, 126, 128, 130, 244, 246, 248, or 436 of FIGS. 1A-1C, 2, 3 and 4A-4C where the isolation region of the growth chamber may have a volume configured to support no more than about $1\times10^3$, $5\times10^2$, $4\times10^2$, $3\times10^2$, $2\times10^2$, $1\times10^2$, 50, 25, 15, or 10 cells in culture. In other embodiments, the isolation region of the growth chamber has a volume that can support up to about 10, 50 or $1\times10^2$ cells. Any configuration of the growth chambers as discussed above may be used in the growth chambers of the microfluidic devices of the kits.

In various embodiments of any of the kits, the size of the growth chambers may be configured to maintain no more than $1\times10^2$ biological cells, where the volume of the growth chambers may be no more than $1\times10^7$ cubic microns. In other embodiments, wherein no more than $1\times10^2$ biological cells may be maintained, the volume of the growth chambers may be no more than $5\times10^6$ cubic microns. In yet other embodiments, no more than 50 biological cells may be maintained, and the volume of the growth chambers may be no more than $1\times10^6$ cubic microns, or no more than $5\times10^5$ cubic microns. In the kits, the microfluidic devices may have any number of growth chambers as discussed above.

The microfluidic device of any of the kits may further include at least one inlet port configured to input the fluidic medium (e.g., first or second fluidic medium) into the flow region and at least one outlet configured to receive the fluidic medium (e.g., spent first fluidic medium), as it exits from the flow region.

The microfluidic device of any of the kits may further include a substrate having a plurality of DEP electrodes, where a surface of the substrate forms a surface of the growth chamber and the flow region. The plurality of DEP electrodes may be configured to generate a dielectrophoresis (DEP) force sufficiently strong to move one or more biological cells (e.g., a clonal population) into or to move one or more cells of a biological cell culture out of a growth chamber or the isolation region thereof. The DEP electrodes, and thus the DEP force may be optically actuated. Such optically actuated DEP electrodes may be virtual electrodes (e.g., regions of an amorphous silicon substrate having increased conductivity due to incident light), phototransistors, or electrodes switched on or off by a corresponding phototransistor. Alternatively, the DEP electrode and thus the DEP force, may be electrically actuated. In some other embodiments, the microfluidic device may further include a substrate having a plurality of transistors, wherein a surface of the substrate forms a surface of the growth chamber and the flow region. The plurality of transistors may be capable of generating a dielectrophoresis (DEP) force sufficiently strong to introduce the biological cell or to move one or more cells of a biological cell culture out of the growth chamber or the isolation region thereof. Each of the plurality of transistors may be optically actuated, and the DEP force may be produced by optoelectronic tweezers.

The microfluidic device of any of the kits may further include a deformable lid region above the at least one growth chamber or isolation region thereof, whereby depressing the deformable lid region exerts a force to export one or more biological cells (e.g., a clonal population) from the growth region to the flow region.

The microfluidic device of any of the kits may be configured to have a lid which is substantially impermeable to gas. Alternatively, all of a portion of the lid may be configured to be gas permeable. The permeable portion of the lid may be permeable to at least one of carbon dioxide, oxygen, and nitrogen. In some embodiments, the lid (or a portion thereof) may be permeable to a combination of more than one of carbon dioxide, oxygen, or nitrogen.

Any of the kits may further include a reservoir configured to contain a fluidic medium. The reservoir may be fluidically connected to any of the microfluidic devices described herein. The reservoir may be configured such that the fluidic medium present in the reservoir may be contacted by a gaseous environment capable of saturating the fluidic medium with dissolved gaseous molecules. The reservoir may further be configured to contain a population of feeder cells in fluidic contact with the fluidic medium.

Any of the kits may include at least one connecting conduit configured to be connected to an inlet port and/or outlet port of the microfluidic device. The connecting conduit may also be configured to connect to a reservoir or a flow controller, such as a pump component. The connecting conduit may be gas permeable. The gas permeable connecting conduit may be permeable to at least one of carbon dioxide, oxygen, and nitrogen. In some embodiments, the gas permeable conduit may be permeable to a combination of more than one of carbon dioxide, oxygen, or nitrogen.

Any of the kits may further include a sensor configured to detect a pH of a first fluidic medium. The sensor may be connected to (or connectable to) an inlet port of the microfluidic device or a connecting conduit attached thereto. Alternatively, the sensor may be integral to the microfluidic device. The sensor may be connected proximal to the point at which fluidic medium enters the microfluidic device. The kit may include a sensor configured to detect a pH of fluidic medium at the outlet of the microfluidic device. The sensor may be connected to (or connectable to) an outlet port of the microfluidic device or a connecting conduit attached thereto. Alternatively, the sensor may be integral to the microfluidic device. The sensor may be connected proximal to the point at which fluidic medium exits the microfluidic device. The sensor, whether attached to the inlet and/or the outlet of the microfluidic device, may be an optical sensor. An optical sensor may include a LED and an integrated colorimetric sensor, which may optionally be a color-sensitive phototransistor. The kit may further include driving electronic components to control the pH sensor and to receive output therefrom. The kit may further include a pH detection reagent. The pH detection reagent may be a pH-sensitive dye that may be detected under visible light.

Any of the kits may also include a culture medium having components capable of enhancing biological cell viability on the microfluidic device. These components may be any suitable culture medium components as is known in the art, including any of the components discussed above for fluidic media components.

Any of the kits may further include at least one reagent to detect a status of a biological cell or a population of cells. Reagents configured to detect the status of the cell are well known in the art, and may be used, for example, to detect whether a cell is alive or dead; is secreting a substance of interest such as antibodies, cytokines, or grow factors; or has cell surface markers of interest. Such reagents may be used without limitation in the kits and methods described herein.

For any of the kits provided herein, the components of the kits may be in separate containers. For any of the components of the kits provided in solution, the components may be present in a concentration that is about 1×, 5×, 10×, 100×, or about 1000× the concentration as used in the methods of the invention.

For the kits where the at least one growth chamber of the microfluidic device has not been pre-treated to condition the at least one surface of the at least one growth chamber, and where the conditioned surface is created by treating with the surface conditioning reagent or for kits including a microfluidic device having a flow region configured to contain a flow of a first fluidic medium; and at least one growth chamber having at least one conditioned surface which can support cell growth, viability, portability, or any combination thereof; and a surface conditioning reagent, the surface of the growth chamber may be pre-conditioned with a surface conditioning reagent. The surface conditioning reagent may include a polymer, which may be any one or more of the polymers described above for use as a surface conditioning reagent. In some embodiments, the surface conditioning reagent may include a polymer having alkylene ether moieties, carboxylic acid moieties, sulfonic acid moieties, amino acid moieties, nucleic acid moieties, saccharide moieties, or any combination thereof. The surface conditioning reagent may include a PEO-PPO block co-polymer, such as a Pluronic® polymer (e.g., L44, L64, P85 or F127. In some embodiments, the surface conditioning reagent may include one or more components of mammalian serum. The mammalian serum may be Fetal Bovine Serum (FBS), or Fetal Calf Serum (FCS).

Alternatively, the surface conditioning reagent used to condition the surface of the growth chamber may be included in the kit, separate from the microfluidic device. In other embodiments of the kit, a pre-conditioned microfluidic device is included along with a surface conditioning reagent different from that used to condition the surface of the growth chamber. The different surface conditioning reagent may be any of the surface conditioning reagents discussed above. In some embodiments, more than one surface conditioning reagent is included in the kit.

In various embodiments of the kits having a microfluidic device where the at least one growth chamber of the microfluidic device has not been pre-treated to condition the at least one surface, the kit may also include a culture medium suitable for culturing the one or more biological cells. In some embodiments, the kit may also include a culture medium additive comprising a reagent capable of replenishing the conditioning of a surface of the growth chamber. The culture medium additive may include a conditioning reagent as discussed above or another chemical species enhancing the ability of the at least one surface of the at least one growth chamber to support cell growth, viability, portability, or any combination thereof. This can include growth factors, hormones, antioxidants or vitamins, and the like.

The kit may also include a flow controller configured to perfuse at least the first fluidic medium, which may be a separate component of the microfluidic device or may be incorporated as part of the microfluidic device. The controller may be configured to perfuse the fluidic medium non-continuously. Thus, the controller may be configured to perfuse the fluidic medium in a periodic manner or in an irregular manner.

In another aspect, a kit is provided for culturing a biological cell, including a microfluidic device having a flow region configured to contain a flow of a first fluidic medium; and at least one growth chamber comprising an isolation region and a connection region, wherein the isolation region is fluidically connected with the connection region and the connection region comprises a proximal opening to the flow region; and further wherein the at least one growth chamber comprises at least one surface conditioned to support cell growth, viability, portability, or any combination thereof. The microfluidic device may be any microfluidic device as described herein, and may have any of the growth chambers as described herein. The microfluidic device may have a substrate having a DEP configuration of any kind described herein. The DEP configuration may be optically actuated. The substrate of the microfluidic device may have a surface including the substrate compositions as described herein of Formula 1 or Formula 2, and have all the features as described above.

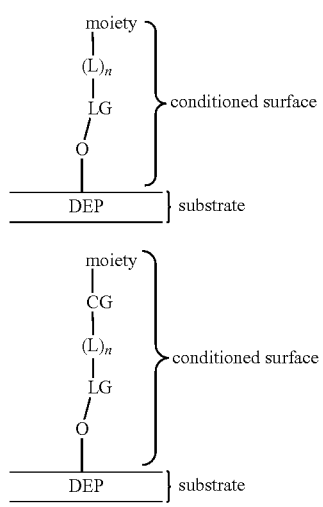

Formula 1

Formula 2

The at least one conditioned surface of the microfluidic device of the kit may include saccharide moieties, alkylene ether moieties, amino acid moieties, alkyl moieties, fluoroalkyl moieties (which may include perfluoroalkyl moieties), anionic moieties, cationic moieties, and/or zwitterionic moieties. In some embodiments, the conditioned surface of the microfluidic device may include saccharide moieties, alkylene ether moieties, alkyl moieties, fluoroalkyl moieties, or amino acid moieties. The alkyl or perfluoroalkyl moieties may have a backbone chain length of greater than 10 carbons. In some embodiments, the conditioned surface to support cell growth, viability, portability, or any combination thereof may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaine; sulfamic acid; or amino acids.

In some embodiments of the kit, the conditioned surface may include a linking group covalently linked to a surface of the microfluidic device, and the linking group may be linked to the moiety configured to support cell growth, viability, portability, or any combination thereof, of the one or more biological cells within the microfluidic device. The linking group may be a siloxy linking group. Alternatively, the linking group may be a phosphonate ester linking group. In some embodiments of the kit, the linking group of the conditioned surface may be directly linked to the moiety configured to support cell growth, viability, portability or any combination thereof.

In other embodiments, the linking group may be indirectly linked to the moiety configured to support cell growth, viability, portability or any combination thereof via a linker. The linking group may be indirectly linked to the moiety configured to support cell growth, viability, portability, or any combination thereof, via connection to a first end of a linker. The linker may further include a linear portion wherein a backbone of the linear portion comprises 1 to 200 non-hydrogen atoms selected from any combination of silicon, carbon, nitrogen, oxygen, sulfur and phosphorus atoms. In some embodiments of the kit, the linker of the conditioned surface may further include a triazolylene moiety. The cleavable moiety is configured to permit disruption of the conditioned surface thereby promoting portability of the biological cell. The kit may further include a reagent configured to cleave the cleavable moiety of the conditioned surface.

In various embodiments of the kit, the kit may further include a surface conditioning reagent. In some embodiments, the surface conditioning reagent may include a polymer comprising at least one of alkylene ether moieties, carboxylic acid moieties, sulfonic acid moieties, phosphonic acid moieties, amino acid moieties, nucleic acid moieties or saccharide moieties. In some other embodiments, the surface conditioning reagent comprises a polymer comprising at least one of alkylene ether moieties, amino acid moieties, or saccharide moieties. In some other embodiments, the conditioned surface may include a cleavable moiety.

In other embodiments of the kit, the surface conditioning reagent comprises at least one cell adhesion blocking molecule. In some embodiments, the at least one cell adhesion blocking molecule may disrupt actin filament formation, block integrin receptors, or reduce binding of cells to DNA fouled surfaces. In some embodiments, the at least one cell adhesion blocking molecule may be Cytochalasin B, an RGD containing peptide, a DNase 1 protein, a fibronectin inhibitor, or an antibody to an integrin. In some embodiments, the at least one cell adhesion blocking molecule may include a combination of more than one type of cell adhesion blocking molecules.

In various embodiments of the kit, the surface conditioning reagent may include one or more components of mammalian serum. The mammalian serum may be Fetal Bovine Serum (FBS), or Fetal Calf Serum (FCS). In various embodiments of the kit, the kit may further include a culture medium suitable for culturing the one or more biological cells. In some embodiments, the kit may include a culture medium additive including a reagent configured to replenish the conditioning of the at least one surface of growth chamber. The culture medium additive may include a conditioning reagent as discussed above or another chemical species enhancing the ability of the at least one surface of the at least one growth chamber to support cell growth, viability, portability, or any combination thereof. This can include growth factors, hormones, antioxidants or vitamins, and the like.

In various embodiments of the kit, the kit may include at least one reagent to detect a status of the one or more biological cells.

In yet another aspect, a kit for culturing a biological cell, including a microfluidic device for culturing one or more biological cells including a flow region configured to contain a flow of a first fluidic medium; and at least one growth chamber including an isolation region and a connection region, wherein the isolation region is fluidically connected with the connection region and the connection region has a proximal opening to the flow region; and the at least one growth chamber has at least one surface having a surface modifying ligand. The microfluidic device may be any microfluidic device as described herein. The surface may include a substrate having a dielectrophoresis (DEP) configuration. The DEP configuration may be any DEP configuration described herein. The DEP configuration may be optically actuated. The substrate is any substrate having a surface modifying ligand as described herein, and may have a structure of Formula 3, and may include all the features as described above:

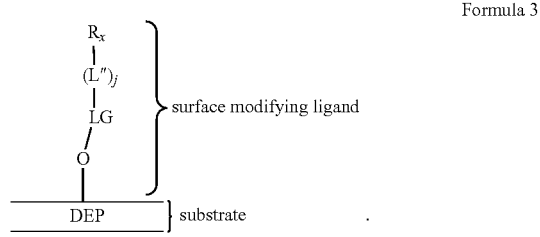

Formula 3

In various embodiments of the kit having a microfluidic device having at least one surface including a surface modifying ligand, the surface modifying ligand may be covalently linked to oxide moieties of the surface of the substrate. The surface modifying ligand may include a reactive moiety. The reactive moiety of the surface modifying ligand may be azido, amino, bromo, a thiol, an activated ester, a succinimidyl or alkynyl moiety. The surface modifying ligand may be covalently linked to the oxide moieties via a linking group. In some embodiments, the linking group may be a siloxy moiety. In other embodiments, the linking group may be a phosphonate ester moiety. The linking group may be connected indirectly via a linker to the reactive moiety of the surface modifying ligand. The linker may include a linear portion wherein a backbone of the linear portion comprises 1 to 100 non-hydrogen atoms selected from any combination of silicon, carbon, nitrogen, oxygen, sulfur and phosphorus atoms. In some embodiments, the surface modifying ligand may include one or more cleavable moieties. The one or more cleavable moieties may be configured to permit disruption of a conditioned surface of a microfluidic device once formed, thereby promoting portability of the one or more biological cells after culturing.

In some embodiments of the kit having a microfluidic device having at least one surface including a surface modifying ligand, the kit may further include a conditioning modification reagent including a first moiety configured to support cell growth, viability, portability, or any combination thereof, and a second moiety configured to react with the reactive moiety of the surface modifying ligand, which may have a structure of Formula 5, and have any of the features as described herein:

$$\text{moiety-}(L')_m\text{-}R_{px}. \quad \text{Formula 5}$$

The second moiety may be configured to convert the surface modifying ligand into a conditioned surface configured to support cell growth, viability, portability, or any combination thereof, of one or more biological cells within the growth chamber upon reaction with the reactive moiety of the surface modifying ligand of the microfluidic device of the kit. The first moiety may include an alkylene oxide moiety, a saccharide moiety; an alkyl moiety, a perfluoroalkyl moiety, an amino acid moiety, an anionic moiety, a cationic moiety or a zwitterionic moiety. In some embodiments, the first moiety may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaine; sulfamic acid; or amino acids. The second moiety may be an amino, carboxylic acid, alkyne, azide, aldehyde, bromo, or thiol moiety. In some embodiments, the first moiety or a linker L' (as described above for Formula 5) of the conditioning modification reagent may include a cleavable moiety. The cleavable moiety may be configured to permit disruption of the conditioned surface thereby promoting portability of the biological cell. In some embodiments, the kit may further include a reagent configured to cleave the cleavable moiety of the conditioned surface.

In some embodiments of the kit having a microfluidic device having at least one surface including a surface modifying ligand, the kit may further include a surface conditioning reagent.

In some embodiments of the kit having a microfluidic device having at least one surface including a surface modifying ligand, the surface conditioning reagent may include a polymer comprising at least one of alkylene ether moieties, carboxylic acid moieties, sulfonic acid moieties, phosphonic acid moieties, amino acid moieties, nucleic acid moieties or saccharide moieties. In some other embodiments, the surface conditioning reagent comprises a polymer comprising at least one of alkylene ether moieties, amino acid moieties, or saccharide moieties. In some other embodiments, the conditioned surface may include a cleavable moiety.

In some embodiments of the kit having a microfluidic device having at least one surface including a surface modifying ligand, the surface conditioning reagent comprises at least one cell adhesion blocking molecule. In some embodiments, the at least one cell adhesion blocking molecule may disrupt actin filament formation, block integrin receptors, or reduce binding of cells to DNA fouled surfaces. In some embodiments, the at least one cell adhesion blocking molecule may be Cytochalasin B, an RGD containing peptide, a DNase 1 protein, a fibronectin inhibitor, or an antibody to an integrin. In some embodiments, the at least one cell adhesion blocking molecule may include a combination of more than one type of cell adhesion blocking molecules.

In some embodiments of the kit having a microfluidic device having at least one surface including a surface modifying ligand, the surface conditioning reagent may include one or more components of mammalian serum. The mammalian serum may be Fetal Bovine Serum (FBS), or Fetal Calf Serum (FCS).

In some embodiments of the kit having a microfluidic device having at least one surface including a surface modifying ligand, the kit may further include a culture medium suitable for culturing the one or more biological cells. In some embodiments, the kit may further include a culture medium additive including a reagent configured to replenish the conditioning of the at least one surface of growth chamber. The culture medium additive may include a conditioning reagent as discussed above or another chemical species enhancing the ability of the at least one surface of the at least one growth chamber to support cell growth, viability, portability, or any combination thereof. This can include growth factors, hormones, antioxidants or vitamins, and the like.

In some embodiments of the kit having a microfluidic device having at least one surface including a surface modifying ligand, the kit may further include at least one reagent to detect a status of the one or more biological cells.

EXAMPLES

Example 1

Culturing and Growth of a K562 Erythroleukemic Cell

Materials:
K562 cells, a human immortalized myelogenous leukemia cell line, were obtained from the American Type Culture Collection (ATCC) (catalog ATCC® CC1-243™) and were provided as a suspension cell line. Cultures were maintained by seeding $1 \times 10^3$ viable cells/mL and incubating at 37° C., using 5% carbon dioxide gaseous environment. Cells were split at $1 \times 10^6$ cells/mL or every 2-3 days. Cells were frozen in 5% dimethyl sulfoxide (DMSO)/95% complete growth medium.

Culture Medium:
Iscove's Modified Dulbecco's Medium (ATCC® Catalog No. 30-2005) plus 10% Fetal Bovine Serum (Hyclone Cat # SH30071.2) were combined to make the complete growth medium. When perfusing during incubation period, the complete growth medium was conditioned continuously with 5% carbon dioxide in air before introduction into the microfluidic device.

Priming Solution:
Complete growth medium containing 0.1% Pluronic® F127 (Life Technologies® Cat # P6866).

System and Microfluidic Device:
Manufactured by Berkeley Lights, Inc. The system included at least a flow controller, temperature controller, fluidic medium conditioning and pump component, light source for light activated DEP configurations, microfluidic device, mounting stage, and a camera. The growth chamber of the microfluidic device used in this experiment had a volume of approximately $1.4 \times 10^5$ cubic microns. The cross sectional area of the flow channel was about $4 \times 10^3$ square microns. The microfluidic device had 8 channels.

Preparation for culturing: The microfluidic device was loaded onto the system and purged with 100% carbon dioxide at 15 psi for 5 min. Immediately following the carbon dioxide purge, the priming solution was perfused through the microfluidic device at 5 microliters/sec for 8 min. The complete growth medium was then flowed through the microfluidic device at 5 microliters/sec for 5 min.

Culturing Conditions:
The temperature of the microfluidic device was maintained at 37° C. Culture medium was perfused throughout the entire period of the culturing experiment at a constant rate of 0.001 microliters/sec.

Figure 10C:
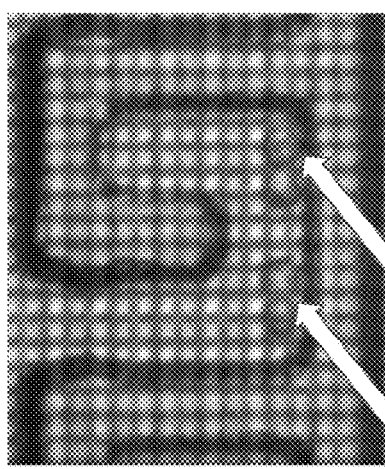
FIGS. 10A-10E are photographic representations of one embodiment of a culturing experiment according to the methods described herein.

A single K562 cell was loaded into one growth chamber of the microfluidic device, using gravity. A photograph is shown of the growth chamber at t=0 h after loading the cell (see FIG. 10A). The arrow 1002 points to the location of the single cell in the growth chamber.

Figure 10B:
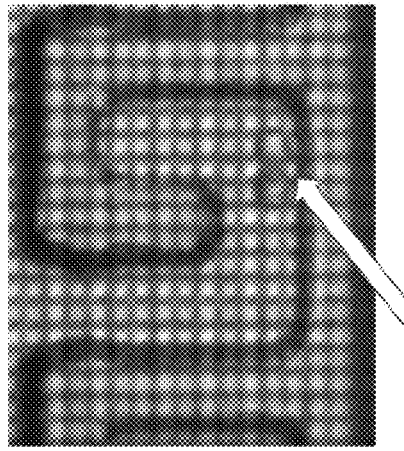
Figure 10A:
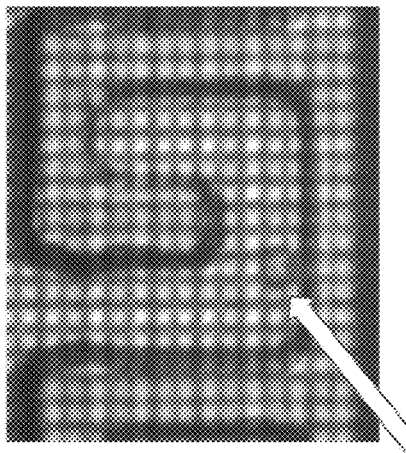

After 16 h of culturing was completed, the cell expanded to a population of 2 cells, as shown in a photograph taken at that time point (See FIG. 10B). Arrow 1004 points to the location of the two cells in the growth chamber.

After 34 hours of culturing was completed the population of cells increased to a total of four cells, as shown in the photograph of FIG. 10C. Arrows 1006 and 1008 point to each of the two groups of two cells located within the growth chamber.

Figure 10E:
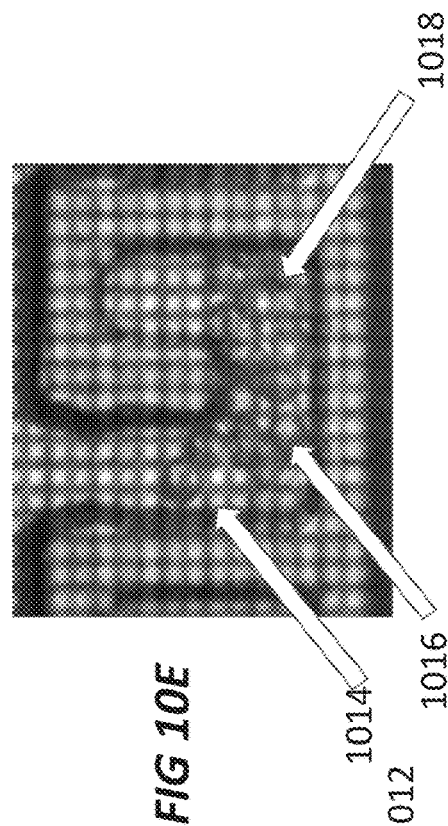
Figure 10D:
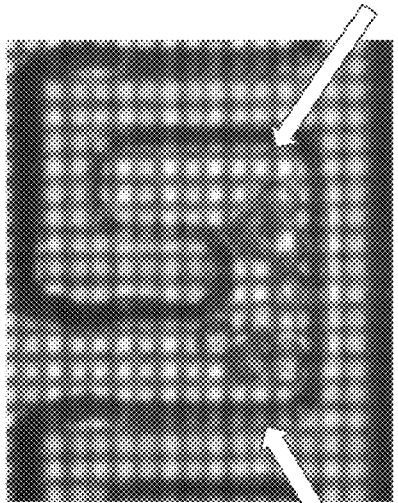

After 54 hours of culturing was completed, the population of K562 cells increased to a total of 8 cells, as shown in the photograph of FIG. 10D. Arrows 1010 and 1012 point to cells at either side of the group of cells within the growth chamber.

After 70 hours of culturing was completed, the population of K562 cells increased to a total of 16 cells, as shown in the photograph of FIG. 10E. Arrows 1014, 1016, and 1018 point to cells of that group. A clonal expanded population of K562 was provided in the growth chamber of the microfluidic device.

Example 2

Culturing and Growth of an OKT3 Hybridoma Cell

Materials:
OKT3 cells, a murine myeloma hybridoma cell line, were obtained from the ATCC (ATCC® Cat. # CRL-8001™). The cells were provided as a suspension cell line. Cultures were maintained by seeding about $1 \times 10^5$ to about $2 \times 10^5$ viable cells/mL and incubating at 37° C., using 5% carbon dioxide in air as the gaseous environment. Cells were split every 2-3 days. OKT3 cell number and viability were counted and cell density is adjusted to $5 \times 10^5$/ml for loading to the microfluidic device.

Culture medium: 500 ml Iscove's Modified Dulbecco's Medium (ATCC® Catalog No. 30-2005), 200 ml Fetal Bovine Serum (ATCC® Cat. #30-2020) and 1 ml penicillin-streptomycin (Life Technologies® Cat. #15140-122) were combined to make the culture medium. The complete medium was filtered through a 0.22 µm filter and stored away from light at 4° C. until use.

When perfusing during incubation period, the culture medium was conditioned continuously with 5% carbon dioxide in air before introduction into the microfluidic device.

Priming Solution:

The culture medium containing 0.1% Pluronic® F127 (Life Technologies® Cat # P6866).

System and Microfluidic Device:

Manufactured by Berkeley Lights, Inc. The system included at least a flow controller, temperature controller, fluidic medium conditioning and pump component, light source and projector for light activated DEP configurations, microfluidic device, mounting stage, and a camera. The growth chamber of the microfluidic device used in this experiment had a volume of approximately $1.5 \times 10^6$ cubic microns. The cross sectional area of a flow channel was $8 \times 10^3$ square microns, and a total of six channels were present on the microfluidic device.

Preparation for Culturing:

The microfluidic device was loaded onto the system and purged with 100% carbon dioxide at 15 psi for 5 min Immediately following the carbon dioxide purge, the priming solution was perfused through the microfluidic device at 8 microliters/sec until a total volume of 2.5 ml was perfused through the microfluidic device. The culture medium was then flowed through the microfluidic device at 8 microliters/sec until a total of 1 ml of culture medium was perfused through the microfluidic device. The prepared microfluidic device is shown, prior to introduction of cells in the photograph of FIG. 11A. A row of four growth chambers extends along the bottom of the photograph.

Culturing Conditions:

The temperature of the microfluidic device was maintained at 37° C. Culture medium was perfused throughout the entire period of the culturing experiment using a variable perfusion method which included an initial 4 h period of perfusion at 0.01 microliters/sec, followed by a short high velocity perfusion at 8 microliters/sec for about 3 sec, followed by a short perfusion stop period of approximately less than a minute. This cycle including alternating perfusion rates and a stop were continued through the culturing experiment.

A single OKT3 cell was introduced into the growth chamber by gravity. A photograph of the growth chamber having one cell at time t=0 is shown in FIG. 11B, where arrow 1102 points to the second chamber from the left, and particularly at the single cell within the chamber, where the region in which the cell is residing is further encompassed by the circle.

FIGS. 12A-12C show photographs of the microfluidic device at later time points in the culturing experiment, and demonstrate cell expansion forming a clonal population. The photograph of FIG. 12A was taken when one day of culturing was completed and arrow 1202 points to a group of about four cells in the second chamber from the left, the site of introduction of the single OKT3 cell. FIG. 12B is a photograph taken after 2 days of culturing was completed and arrow 1204 points to a further multiplied population of cells in the second chamber from the left. FIG. 12C is a photograph taken after 3 days of culturing was completed, and arrow 1206 shows a multitude of expanded OKT3 cells arising from culturing the single OKT 3 cell.

FIGS. 13A-13C show photographs of the microfluidic device after completion of three days of culturing (i.e., after the time point of FIG. 12C), and demonstrate exportation of a selection of the expanded OKT 3 cells, using a dielectrophoresis force produced by optoelectronic tweezers. In FIG. 13A, the pattern of light (i.e., a light trap, to which arrow 1302 points) which initiates the dielectrophoresis force is shown as a white box around the cells. The cells were moved from the bottom of the growth chamber towards the flow channel, by the optically actuated dielectrophoresis forces. The photograph of FIG. 13B show further movement of the expanded OKT 3 cells into the flow region. The cells were still trapped in the light trap and were forced to move with the light trap (arrow 1304). The photograph of FIG. 13C shows release of the expanded cells, once they were moved completely into the flow region (arrow 1306). These cells were exported out of the microfluidic device for further study or expansion by use of optically actuated DEP forces, gravity or fluid flow.

This experiment demonstrates the selectivity, precision and flexibility provided by use of the devices and methods described herein.

Example 3

Removal of Adherent Cells Using a Serum Free Medium to Condition Surfaces of a Microfluidic Device System and Microfluidic Device.

As in Example 1, with growth chambers having a volume of about $7 \times 10^5$ cubic microns.

Priming Regime.

250 microliters of 100% carbon dioxide was flowed in at a rate of 12 microliters/sec. This was followed by 250 microliters of PBS containing 0.1% Pluronic® F27 (Life Technologies® Cat # P6866), flowed in at 12 microliters/sec. The final step of priming included 250 microliters of PBS, flowed in at 12 microliters/sec. Introduction of the culture medium follows.

Perfusion Regime.

The perfusion method was either of the following two methods:

1. Perfuse at 0.01 microliters/sec for 2 h; perfuse at 2 microliters/sec for 64 sec; and repeat.

2. Perfuse at 0.02 microliters/sec for 100 sec; stop flow 500 sec; perfuse at 2 microliters/sec for 64 sec; and repeat.

Culture Medium.

Serum free medium (ThermoFisher Scientific, Cat. No. 12045-096).

System and Microfluidic Device.

The ability to remove adherent cells from the flow channel of a microfluidic device after culturing is demonstrated by pre-incubating adherent cells (which may be, for example, JIMT1 cells, which are commercially available from AddexBio, Cat. No. C000605) in a serum free culture medium with a conditioning culture medium additive, B-27® Supplement (2% v/v) for 30 min at 36° C. After pre-incubation, the adherent cells are introduced to the flow channel, flow is stopped, and the adherent cells are cultured for a period of 2 h to about 24 h. After the conclusion of the assay, flow of the serum-free culture medium is introduced at a rate of 5 microliters/sec. About 750 microliters of flow passes through the microfluidic device representing about 150× microfluidic device volumes, all of the adherent JIMT1 cells are exported out of the flow channel and out of the microfluidic device. This experiment shows that the serum free medium which may contain supplemental components such as the commercially available B27, can prevent adhesion during the course of an assay incorporating adherent reporter cells, and permit export of adherent cells from the microfluidic device.

Example 4

Removal of Adherent Cells Using a Conditioning Cocktail to Condition Surfaces of a Microfluidic Device Adherent Cells:
as above for Example 3.
Culture Medium.
A serum free culture medium (ThermoFisher Scientific, Cat. No. 12045-076) with added components including but not limited to FBS (commercially available from ThermoFisher Scientific, Cat No. 16000-036) and penicillin-streptomycin (ThermoFisher Scientific Cat. No. 15140-163).
Conditioning Cocktail:
CytochalasinB (Sigma Aldrich, Catalog No. C2743-200UL); DNaseI (New England Biosciences Cat No: M0303S); and RGD tripeptide (Santa Cruz Biotechnology Cat No: sc-201176).
Adherent Cell Preparation:
The culture medium is modified with the conditioning cocktail to have a final concentration of 4 micromolar CytochalasinB; 0.1 Unit/microliter DNaseI; and 1 millimolar RGD tripeptide. The adherent cells are incubated for 30 min at 36° C. prior to importation into the microfluidic device.
System and Microfluidic Device.
As above, with growth chambers having a volume of about $7 \times 10^5$ cubic microns.
The ability to remove adherent cells (e.g. JIMT1 cells) from the flow channel of a microfluidic device after culturing is demonstrated by pre-incubating the adherent cell population pre-incubated with a conditioning cocktail. Notably, the use of the conditioning cocktail permits use of serum containing media, such as the medium used in this example, within the microfluidic environment while still affording removal of adherent cells.
The pre-incubated adherent cells are introduced into the flow channel of the microfluidic device, and the adherent cells are incubated for a period of 2 h to about 24 h. After the conclusion of the assay, flow of culture medium is introduced at a rate of 5 microliters/sec. About 750 microliters of flow passes through the microfluidic device representing about 150× microfluidic device volumes, all of the adherent cells are exported out of the flow channel and out of the microfluidic device. This experiment shows that the conditioning cocktail can prevent adhesion and permit export of adhesive cells.

Example 5

Preparation of Microfluidic Devices Having Conditioned Surfaces

For all Preparations:
Microfluidic device: As above for example 1, manufactured by Berkeley Lights, Inc., and used as received. In all cases, silicon substrates and ITO/glass substrates with patterned silicone (PPS) were oxygen plasma cleaned in a Nordson Asymtek plasma cleaner (100 W power, 50 s) prior to synthesis of conditioned surfaces.

A. Perfluoroalkyl Siloxy Conditioned Surface.
Materials:
Heptadecafluoro-1,1,2,2-tetrahydrodecyltrimethoxysilane was obtained from Gelest (Cat. No. SIH5841.5) and used as received. $MgSO_4$ $7H_2O$ (Acros) was used as received.
Method of Preparation.
Assembled microfluidic devices were chemically modified by exposing them to heptadecafluoro-1,1,2,2-tetrahydrodecyltrimethoxysilane and water vapor at elevated temperature under reduced pressure. 300 microliters of heptadecafluoro-1,1,2,2-tetrahydrodecyltrimethoxysilane and 0.5 g $MgSO_4$ $7H_2O$ (water source) were added to separate aluminum boats in the bottom of a clean, dry 6" glass vacuum desiccator. The microfluidic devices were supported on a perforated plate above the silane reagent and hydrate salt (water source). The desiccator was pumped to 750 mTorr at room temperature and sealed. The desiccator was then placed into a 110° C. oven for 24 h. The microfluidic devices having a perfluoroalkyl conditioned surface were then removed from the desiccator and used.
In some experiments, the microfluidic devices were chemically modified before being mounted to printed circuit boards.
B. Dextran Conditioned Surface.
Materials.
11-azidoundecyltrimethoxysilane was synthesized from 11-bromoundecyltrimethoxysilane (Gelest) by displacing the bromide moiety with sodium azide. In a typical reaction, 4.00 g of 11-bromoundecyltrimethoxysilane (Gelest) was added to a solution containing 2.00 g of sodium azide (Sigma-Aldrich) in 60 mL of dry dimethylformamide (DMF) (Acros). The solution was stirred for 24 h at room temperature under nitrogen. Next, the solution was filtered, and the filtrate was extracted with dry pentane (Acros). The crude 11-azidoundecyltrimethoxysilane product was concentrated by rotary evaporation and was purified by two successive vacuum distillations.
Dibenzocyclooctyne (DBCO)-modified dextran (MW~3000 Da) was purchased from Nanocs and used as received.
Method of Preparation. Introduction of a Surface Modifying Ligand.
Surfaces of assembled microfluidic devices were chemically modified by exposing them to 11-azidoundecyltrimethoxysilane and water vapor at elevated temperature under reduced pressure. 300 microliters of 11-azidoundecyltrimethoxysilane and 0.5 g $MgSO_4$ $7H_2O$ (water source) were added to separate aluminum boats in the bottom of a clean, dry 6" glass vacuum desiccator. Microfluidic devices were supported on a perforated plate above the silane and hydrate salt (water source). The desiccator was pumped to 750 mTorr at room temperature and sealed. The desiccator was then placed into a 110 C oven for 24 h. The microfluidic chips having the surface modifying ligand, a 11-azidoundecylsiloxy moiety, were then removed from the desiccator. In some experiments, the microfluidic devices were chemically modified before being mounted to printed circuit boards.
Introduction of the Dextran Conditioned Surface.
Azide-terminated microfluidic device surfaces were reacted with DBCO-dextran by flowing at least 250 microliters of an aqueous solution containing 166 micromolar DBCO-dextran through the microfluidic devices having surface modifying azide ligands after vapor deposition. The reaction was allowed to proceed at room temperature for at least 1 h. The chips were then rinsed by flowing at least 250 microliters of DI water through the chips.

C. Polyethylene Glycol (PEG) Conditioned Surface.

Materials.

11-azidoundecyltrimethoxysilane was synthesized as above. Alkyne-modified PEG (MW~5000 Da) was purchased from JenKem and used as received. Sodium ascorbate and copper sulfate pentahydrate were purchased from Sigma-Aldrich and used as received. (tris(3-hydroxypropyltriazolylmethyl)amine) THPTA copper catalyzed click reagent (Glen Research).

Methods of Preparation. Introduction of a Surface Modifying Ligand.

Microfluidic chips having a 11-azidoundecylsiloxy surface modifying ligand were prepared as above.

Introduction of the PEG Conditioned Surface.

Azide-terminated surfaces of the microfluidic devices were reacted with alkyne-modified PEG by flowing at least 250 microliters of an aqueous solution containing 333 micromolar alkyne-modified PEG, 500 micromolar copper sulfate, 500 micromolar THPTA ligand and 5 millimolar sodium ascorbate through the microfluidic devices having the 11-azidoundecylsiloxy surface modifying ligand. The reaction was allowed to proceed at room temperature for at least 1 hour. The microfluidic devices with a PEG conditioned surface were then rinsed by flowing at least 250 microliters of deionized water through the devices.

D. Alkyl Modified Surface Having a Phosphonate Ester Linking Group to the Surface.

Materials.

Octadecylphosphonic acid is purchased from Sigma Aldrich and used as received. Acetone and ethanol is purchased from Sigma Aldrich.

Methods of Preparation.

The surfaces of the microfluidic devices are exposed to a 10 millimolar solution of octadecylphosphonic acid in dry ethanol at 35° C. for 48 hours. The resulting microfluidic devices having alkyl conditioned surfaces attached via a phosphonate ester linking group are rinsed copiously with ethanol and DI water after deposition.

Example 6

Culturing and Export of T Lymphocytes on a Conditioned Microfluidic Surface

Materials.

CD3+ cells from AllCells Inc. and mixed with anti-CD3/ anti-CD28 magnetic beads (Dynabeads®, Thermofisher Scientific, Cat. No. 11453D) at a ratio of 1 bead/1 cell. The mixture was incubated in the same medium as the culturing experiment itself, for 5 hours in a 5% $CO_2$ incubator at 37° C. Following the incubation, the T cell/bead mixture was resuspended for use.

Culture Medium.

RPMI-1640 (GIBCO®, ThermoFisher Scientific, Cat. No. 11875-127), 10% FBS, 2% Human AB serum (50 U/ml IL2; R&D Systems).

Priming Procedure:

As above, for Example 3.

Perfusion Regime:

As above, for Example 3.

System and Microfluidic Device:

As above for Example 3. The growth chambers have a volume of about $7 \times 10^5$ cubic microns.

Conditioned Surface.

The microfluidic device had a covalently linked dextran conditioned surface, prepared as described above.

The T cell plus bead) suspension was introduced into the microfluidic device by flowing the resuspension through a fluidic inlet and into the microfluidic channel. The flow was stopped and T cells/beads were randomly loaded into growth chambers by tilting the chip and allowing gravity to pull the T cells/beads into the growth chambers.

Figure 14A:
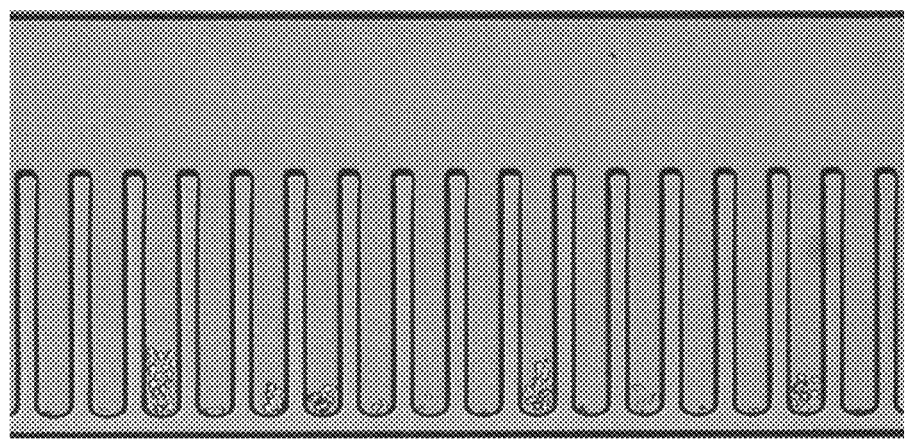
FIGS. 14A and 14B are photographic representations of an embodiment of another culturing experiment in a microfluidic device having at least one conditioned surface.

After loading the T cells/beads into the growth chambers, the culture medium was perfused through the microfluidic channel of the nanofluidic chip for a period of 4 days. FIG. 14A showed the growth of T cells on the dextran conditioned surface of the growth chambers of the microfluidic device. The growth of T cell on the dextran conditioned surface was improved relative to a non-conditioned surface of a similar microfluidic device (data not shown).

Figure 14B:
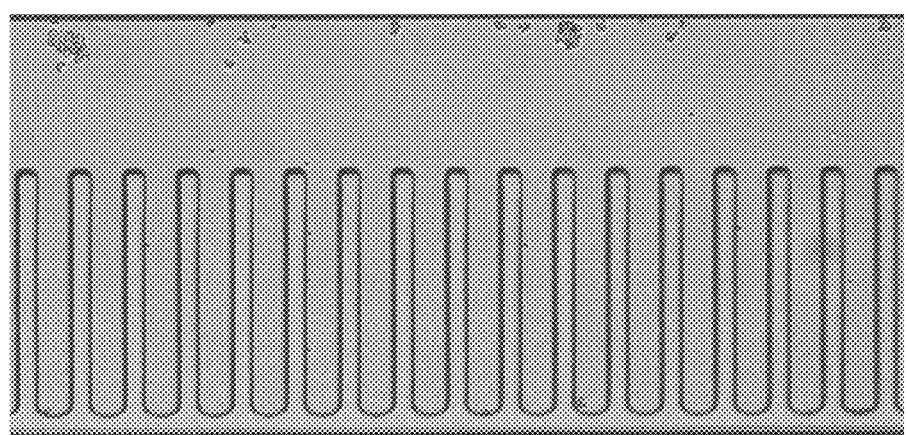

The T cells were then removed from the growth chambers by gravity (e.g., tilting the microfluidic device). FIG. 14B showed the extent of removal from the growth chamber at the end of a twenty minute period, demonstrating excellent ability to export the expanded T cells into the flow channel, which was improved over that of removal of T cells from a non-conditioned surface of a similar microfluidic device. The T cells were then exported from the microfluidic device (not shown).

The examples shown here are exemplary and in no way limit the scope of the methods and apparatuses described throughout the entire description.

What is claimed:

1. A microfluidic device for culturing one or more mammalian cells comprising:
   an enclosure having a single inlet port, a single outlet port and a flow region connecting the single inlet and outlet ports and configured to contain a flow of a first fluidic medium; and
   at least one growth chamber comprising an isolation region having a single opening and a connection region, the connection region comprising a proximal opening to the flow region and a distal opening to the isolation region, wherein a width $W_{con}$ of the connection region at the proximal opening is about 20 microns to about 100 microns and a length $L_{con}$ of the connection region from the proximal opening to the distal opening is at least 1.0 times the width $W_{con}$ of the connection region at the proximal opening, and wherein when the first fluidic medium flows within the flow region, the connection region is configured to allow diffusion of the first fluidic medium into the isolation region while allowing substantially no fluid flux into the isolation region;
   wherein the at least one growth chamber further comprises at least one surface conditioned to support cell growth, viability, portability, or any combination thereof of said mammalian cells within the microfluidic device.

2. The microfluidic device of claim 1, wherein the at least one conditioned surface is conditioned with a polymer comprising alkylene ether moieties.

3. The microfluidic device of claim 1, wherein the at least one conditioned surface is conditioned with a polymer comprising saccharide moieties.

4. The microfluidic device of claim 1, wherein the at least one conditioned surface comprises covalently bound molecules, each having a linking group covalently linked to the at least one surface, a linker, and a moiety configured to support cell growth, viability, portability, or any combination thereof within the microfluidic device.

5. The microfluidic device of claim 4, wherein the linking group is a siloxy linking group.

6. The microfluidic device of claim 4, wherein the covalently bound molecules comprise alkyl or fluoroalkyl linkers.

7. The microfluidic device of claim 6, wherein the alkyl or fluoroalkyl linkers have a backbone chain length of greater than 10 carbons.

8. The microfluidic device of claim 4, wherein the covalently bound molecules further comprise a coupling group.

9. The microfluidic device of claim 4, wherein the covalently bound molecules comprise saccharide moieties.

10. The microfluidic device of claim 4, where the covalently bound molecules comprise alkylene ether moieties.

11. The microfluidic device of claim 1, wherein the microfluidic device further comprises a substrate having a dielectrophoresis (DEP) configuration configured to introduce at least one of the mammalian cells into the isolation region using a DEP force.

12. The microfluidic device of claim 11, wherein the DEP configuration is optically actuated.

13. The device of claim 1, wherein the length $L_{on}$ of the connection region is at least 2.0 times the width $W_{con}$ at the proximal opening of the connection region.

14. The device of claim 1, wherein the length $L_{con}$ of the connection region is between about 20 microns and about 500 microns.

15. The device of claim 1, wherein a width of the microfluidic channel at the proximal opening of the connection region is between about 50 microns and about 500 microns.

16. The device of claim 1, wherein a height of the microfluidic channel at the proximal opening of the connection region is between 20 microns and 100 microns.

17. The device of claim 1, wherein the volume of the isolation region ranges from about $2 \times 10^4$ to about $2 \times 10^6$ cubic microns.

18. The microfluidic device of claim 8, wherein the linker comprises a triazolylene group.

19. The microfluidic device of claim 4, wherein the linker comprises a linear portion having a backbone comprising 1 to 200 non-hydrogen atoms comprising one or more of silicon, carbon, nitrogen, oxygen, sulfur and phosphorus atoms, wherein the linker comprises a triazolylene interrupting the linear portion of the linker or connected to the linear portion of the linker.

20. The microfluidic device of claim 4, wherein the linker comprises a linear portion having a backbone comprising 1 to 200 non-hydrogen atoms comprising one or more of silicon, carbon, nitrogen, oxygen, sulfur and phosphorus atoms, wherein the linear portion is interrupted by one or more of ether, amino, carbonyl, amido, or phosphonate groups.

21. The microfluidic device of claim 4, wherein the linker comprises a linear portion having a backbone comprising 1 to 200 non-hydrogen atoms comprising one or more of silicon, carbon, nitrogen, oxygen, sulfur and phosphorus atoms, wherein one or more arylene, heteroarylene, or heterocyclic groups interrupts the backbone of the linker.

22. The microfluidic device of claim 4, wherein the linker comprises a linear portion having a backbone comprising 1 to 200 non-hydrogen atoms comprising one or more of silicon, carbon, nitrogen, oxygen, sulfur and phosphorus atoms, wherein the backbone of the linear portion comprises 5 to 100 carbon atoms.

23. The microfluidic device of claim 1, wherein the conditioned surface comprises covalently bound molecules and has a thickness of less than 10 nm.

24. The microfluidic device of claim 23, wherein the conditioned surface comprises a monolayer of covalently bound molecules.

25. A method of culturing at least one biological cell in a microfluidic device comprising an enclosure having a single inlet port, a single outlet port and a flow region connecting the single inlet and outlet ports and configured to contain a flow of a first fluidic medium, and at least one growth chamber comprising an isolation region having a single opening and a connection region, the connection region comprising a proximal opening to the flow region and a distal opening to the isolation region, wherein a width $W_{con}$ of the connection region at the proximal opening is about 20 microns to about 100 microns and a length $L_{con}$ of the connection region from the proximal opening to the distal opening is at least 1.0 times the width $W_{con}$ of the connection region at the proximal opening, the method comprising the steps:

causing the first fluidic medium to flow within the flow region, wherein the connection region is configured to allow diffusion of the first fluidic medium into the isolation region while allowing substantially no fluid flux within the isolation region;

introducing the at least one biological cell into the at least one growth chamber, wherein the at least one growth chamber is configured to have at least one surface conditioned to support cell growth, viability, portability, or any combination thereof; and incubating the at least one biological cell for a period of time at least long enough to expand the at least one biological cell to produce a colony of biological cells.

26. The method of claim 25, further comprising perfusing the first fluidic medium during the incubating step, wherein the first fluidic medium is introduced via at least one inlet port of the microfluidic device and exported via at least one outlet port of the microfluidic device, wherein, upon export, the first fluidic medium comprises components from the second fluidic medium.

27. The method of claim 25, wherein the at least one conditioned surface comprises covalently bound molecules, each having a linking group covalently linked to the at least one surface, a linker, and a moiety configured to support cell growth, viability, portability, or any combination thereof within the microfluidic device.

28. The method of claim 27, wherein the covalently bound molecules further comprise a coupling group.

29. The method of claim 25, further comprising conditioning a surface of the at least one growth chamber.

30. The method of claim 29, wherein the conditioning comprises treating the surface of the at least one growth chamber with a conditioning reagent comprising a polymer.

31. The method of claim 25, wherein introducing the at least one biological cell into the at least one growth chamber comprises using a dielectrophoresis (DEP) force having sufficient strength to move the at least one biological cell.

32. The method of claim 25, further comprising exporting one or more biological cells out of the growth chamber or the isolation region thereof into the flow region.

33. The method of claim 25, wherein the at least one biological cell is an immunological cell.

34. The method of claim 25, wherein the at least one biological cell is an adherent cell.

35. The method of claim 25, wherein introducing the at least one biological cell into the at least one growth chamber comprises introducing a single cell into the growth chamber, and wherein the colony of biological cells produced by the incubating step is a clonal colony.

36. The method of claim 33, wherein the immunological cell is a T cell or a B cell.

37. The method of claim 25, wherein the at least one biological cell is a plant cell.

38. The method of claim 25, further comprising forming the at least one conditioned surface by exposing an intermediate modified surface having a reactive moiety with a conditioning modification reagent comprising a reactive pairing moiety comprising one or more of an alkyne, azide, active ester, and aldehyde, wherein the reactive pairing moiety reacts with the reactive moiety.

39. The method of claim 27, wherein the wherein the linker comprises a linear portion having a backbone comprising 1 to 200 non-hydrogen atoms comprising one or more of silicon, carbon, nitrogen, oxygen, sulfur and phosphorus atoms, wherein the linear portion is interrupted by one or more of triazolylene, ether, amino, carbonyl, amido, or phosphonate groups.

40. The method of claim 25, where the covalently bound molecules comprise alkylene ether moieties or saccharide moieties.

41. The method of claim 25, where the covalently bound molecules comprise alkyl or fluoroalkyl linkers.

42. The method of claim 41, wherein the alkyl or fluoroalkyl linkers have a backbone chain length of greater than 10 carbons.

\* \* \* \* \*

UNITED STATES PATENT AND TRADEMARK OFFICE
CERTIFICATE OF CORRECTION

Page 1 of 2

PATENT NO. : 10,723,988 B2
APPLICATION NO. : 15/135707
DATED : July 28, 2020
INVENTOR(S) : Randall D. Lowe, Jr. et al.

It is certified that error appears in the above-identified patent and that said Letters Patent is hereby corrected as shown below:

In the Claims

Claim 1, Column 102, Line 54: after "thereof of said" and before "mammalian cells", insert --one or more--.
Claim 11, Column 103, Line 19: after "at least one of the" and before "mammalian cells", insert --one or more--.
Claim 15, Column 103, Line 30: after "wherein a width of the" and before "at the proximal opening", insert --flow region-- and delete "microfluidic channel".
Claim 16, Column 103, Line 34: after "wherein a height of the" and before "at the proximal opening", insert --flow region-- and delete "microfluidic channel".
Claim 17, Column 103, Line 36: after "wherein" and before "volume of the isolation", delete "the" and insert --a--.
Claim 26, Column 104, Line 37: after "introduced via" and before "inlet port of the", delete "at least one" and insert --the single--.
Claim 26, Column 104, Line 38: after "device and exported via" and before "outlet port of", delete "at least one" and insert --the single--.
Claim 26, Column 104, Line 40: after "components from" and before "second fluidic medium", delete "the" and insert --a--.
Claim 29, Column 104, Line 50: after "further comprising conditioning" and before "surface of the", delete "a" and insert --the at least one--.
Claim 30, Column 104, Line 53: after "comprises treating the" and before "surface of the", insert --at least one--.
Claim 32, Column 104, Line 60: after "biological cells out of the" and before "growth chamber", insert --at least one--.
Claim 35, Column 105, Line 1: after "introducing a single cell into the" and before "growth chamber", insert --at least one--.
Claim 39, Column 105, Line 15: after "39. The method of claim 27," and before the "wherein the", delete "wherein the".
Claim 40, Column 105, Line 22: after "The method of claim" and before "where the covalently", delete "25" and insert --27--.

Signed and Sealed this
Twenty-seventh Day of September, 2022

Katherine Kelly Vidal
*Director of the United States Patent and Trademark Office*

Claim 41, Column 105, Line 25: after "The method of claim" and before "where the covalently", delete "25" and insert --27--.